United States Patent
Bergmann et al.

(10) Patent No.: US 10,067,063 B2
(45) Date of Patent: Sep. 4, 2018

(54) PROGNOSIS AND RISK ASSESSMENT IN STROKE PATIENTS BY DETERMINING THE LEVEL OF MARKER PEPTIDES

(71) Applicant: B.R.A.H.M.S. GMBH, Hennigsdorf (DE)

(72) Inventors: Andreas Bergmann, Berlin (DE); Nils Morgenthaler, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 143 days.

(21) Appl. No.: 13/868,351

(22) Filed: Apr. 23, 2013

(65) Prior Publication Data

US 2014/0017808 A1    Jan. 16, 2014

Related U.S. Application Data

(62) Division of application No. 13/125,911, filed as application No. PCT/EP2009/007738 on Oct. 22, 2009, now abandoned.

(30) Foreign Application Priority Data

Oct. 24, 2008 (EP) .................... 08167512
Nov. 7, 2008 (EP) .................... 08168671

(51) Int. Cl.
| | |
|---|---|
| G01N 33/53 | (2006.01) |
| A61P 9/10 | (2006.01) |
| G01N 21/76 | (2006.01) |
| G01N 33/68 | (2006.01) |
| C07K 14/575 | (2006.01) |
| C07K 14/58 | (2006.01) |
| C07K 14/61 | (2006.01) |
| C07K 7/16 | (2006.01) |

(52) U.S. Cl.
CPC ............... *G01N 21/76* (2013.01); *A61P 9/10* (2018.01); *G01N 33/53* (2013.01); *G01N 33/6893* (2013.01); *C07K 7/16* (2013.01); *C07K 14/57527* (2013.01); *C07K 14/57536* (2013.01); *C07K 14/58* (2013.01); *C07K 14/61* (2013.01); *G01N 2333/4737* (2013.01); *G01N 2333/58* (2013.01); *G01N 2333/585* (2013.01); *G01N 2333/59* (2013.01); *G01N 2800/32* (2013.01)

(58) Field of Classification Search
None
See application file for complete search history.

(56) References Cited

U.S. PATENT DOCUMENTS

2008/0213746 A1    9/2008   Ng et al.
2011/0263821 A1    10/2011  Bergmann et al.

FOREIGN PATENT DOCUMENTS

WO    WO 2008-049422 A2    5/2008

OTHER PUBLICATIONS

Magga et al (2004. J Appl Physiol. 96: 1306-1311).*
Vuolteenaho et al (1992 Am J Physiol. 32: R647-R652).*
Nishida et al, 2008 (Peptides. 29:599-605).*
Abassi, et al., "Implications of the Natriuretic Peptide System in the Pathogenesis of Heart Failure: Diagnostic and Therapeutic Importance," Pharmacology & Therapeutics, vol. 102, No. 3 (Jun. 2004), pp. 223-241.
Donckier, et al., "Reduction of Elevated Plasma Concentrations of Atrial Natriuretic Peptide (ANP) After Successful Cardioversion for Atrial Tachyarrythmias," Regulatory Peptides, Elsevier Science BV, vol. 13, No. 1 (Dec. 1, 1985), p. 97.
Hall, et al., "N-Terminal Proatrial Natriuretic Factor. An Independent Predictor of Long-Term Prognosis After Myocardial Infarction," Circulation, vol. 89, No. 5 (May 1, 1994), pp. 1934-1942.
Katan, et al., "Copeptin, the C-terminal part of the vasopressin pro-hormone to predict outcome in patients with stroke," Neurology, 255(S2): 12, Jun. 2008, 1 page.
International Search Report of PCT/EP2009/007738 (dated Jan. 25, 2010).
O'Neill, et al., "Fluid Balance in Elderly Patients following Acute Stroke," Age and Ageing 1992; 21:4, 280-285.
Makikallio, et al., "Natriuretic Peptides and Mortality After Stroke," Stroke (36), May 2005, pp. 1016-1020, downloaded from http://stroke.abajournals.org.
Miyakis, et al., "Letter to the Editor—Serial Serum Procalcitonin Changes in the Prognosis of Acute Stroke," Clinica Chimica Acta, Vo. 350, pp. 237-239, 2004.
Morgenthaler, et al., "Detection of Procalcitonin (PCT) in Healthy Controls and Patients with Local Infection by a Sensitive ILMA," Clin. Lab., vol. 48, pp. 263-270, 2002.
European Office Action corresponding to Application No: 09 744 085.3-1408, dated May 17, 2017.
Alfons Gegenhuber et al., "Comparative Evaluation of B-Type Natriuretic Peptide, Mid-Regional Pro-A-type Natriuretic Peptide, Mid-Regional Pro-Adrenomedullin, and Copeptin to Predict 1-Year Mortality in Patients With Acute Destabilized Heart Failure", Journal of Cardiac Failure, vol. 13, No. 1, (2007), pp. 42-49.

* cited by examiner

*Primary Examiner* — Zachary C Howard
(74) *Attorney, Agent, or Firm* — Millen White Zelano & Branigan, PC

(57) ABSTRACT

The present invention relates to a method for prognosis of an outcome or assessing the risk of a patient having suffered a stroke or a transient ischemic attack, comprising the determination of the level of at least one marker peptide in said sample said marker peptide selected from the group comprising ANP, AVP, ADM, ET-1, troponin, CRP, calcitonin and hGH or fragments thereof or its precursor or fragments thereof and attributing the level of said at least one marker peptides its precursor or fragments thereof with the prognosis of an outcome or assessing the risk for said patient.

9 Claims, 78 Drawing Sheets
Specification includes a Sequence Listing.

Fig. 75

```
1    MKLVSVALMY LGSLAFLGAD TARLDVASEF RKKWNKWALS RGKRELRMSS
51   SYPTGLADVK AGPAQTLIRP QDMKGASRSP EDSSPDAARI RVKRYRQSMN
101  NFQGLRSFGC RFGTCTVQKL AHQIYQFTDK DKDNVAPRSK ISPQGYGRRR
151  RRSLPEAGPG RTLVSSKPQA HGAPAPPSGS APHFL
```

Fig. 76

```
1    ARLDVASEFR KKWNKWALSR GKRELRMSSS YPTGLADVKA GPAQTLIRPQ
51   DMKGASRSPE DSSPDAARIR VKRYRQSMNN FQGLRSFGCR FGTCTVQKLA
101  HQIYQFTDKD KDNVAPRSKI SPQGYGRRRR RSLPEAGPGR TLVSSKPQAH
151  GAPAPPSGSA PHFL
```

Fig. 77

```
1    ARLDVASEFR KKWNKWALSR
```

Fig. 78

```
1    ELRMSSSYPT GLADVKAGPA QTLIRPQDMK GASRSPEDSS PDAARIRV
```

Fig. 79

```
1    YRQSMNNFQG LRSFGCRFGT CTVQKLAHQI YQFTDKDKDN VAPRSKISPQ
51   GY
```

Fig. 80

```
1    MSSFSTTTVS FLLLLAFQLL GQTRANPMYN AVSNADLMDF KNLLDHLEEK
51   MPLEDEVVPP QVLSEPNEEA GAALSPLPEV PPWTGEVSPA QRDGGALGRG
101  PWDSSDRSAL LKSKLRALLT APRSLRRSSC FGGRMDRIGA QSGLGCNSFR
151  YRR
```

Fig. 81

```
1    NPMYNAVSNA DLMDFKNLLD HLEEKMPLED EVVPPQVLSE PNEEAGAALS
51   PLPEVPPWTG EVSPAQRDGG ALGRGPWDSS DRSALLKSKL RALLTAPRSL
101  RRSSCFGGRM DRIGAQSGLG CNSFRY
```

Fig. 82

```
1    SLRRSSCFGG RMDRIGAQSG LGCNSFRY
```

Fig. 83

```
1    NPMYNAVSNA DLMDFKNLLD HLEEKMPLED EVVPPQVLSE PNEEAGAALS
51   PLPEVPPWTG EVSPAQRDGG ALGRGPWDSS DRSALLKSKL RALLTAPR
```

Fig. 84

```
1    PEVPPWTGEV SPAQRDGGAL GRGPWDSSDR SALLKSKL
```

Fig. 85

```
1    MPDTMLPACF LGLLAFSSAC YFQNCPRGGK RAMSDLELRQ CLPCGPGGKG
51   RCFGPSICCA DELGCFVGTA EALRCQEENY LPSPCQSGQK ACGSGGRCAA
101  FGVCCNDESC VTEPECREGF HRRARASDRS NATQLDGPAG ALLLRLVQLA
151  GAPEPFEPAQ PDAY
```

Fig. 86

```
1    CYFQNCPRGG KRAMSDLELR QCLPCGPGGK GRCFGPSICC ADELGCFVGT
51   AEALRCQEEN YLPSPCQSGQ KACGSGGRCA AFGVCCNDES CVTEPECREG
101  FHRRARASDR SNATQLDGPA GALLLRLVQL AGAPEPFEPA QPDAY
```

Fig. 87

```
1    CYFQNCPRG
```

Fig. 88

```
1    ASDRSNATQL DGPAGALLLR LVQLAGAPEP FEPAQPDAY
```

Fig. 89

```
1    AMSDLELRQC LPCGPGGKGR CFGPSICCAD ELGCFVGTAE ALRCQEENYL
51   PSPCQSGQKA CGSGGRCAAF GVCCNDESCV TEPECREGFH RRA
```

Fig. 90

```
1    MDYLLMIFSL LFVACQGAPE TAVLGAELSA VGENGGEKPT PSPPWRLRRS
51   KRCSCSSLMD KECVYFCHLD IIWVNTPEHV VPYGLGSPRS KRALENLLPT
101  KATDRENRCQ CASQKDKKCW NFCQAGKELR AEDIMEKDWN NHKKGKDCSK
151  LGKKCIYQQL VRGRKIRRSS EEHLRQTRSE TMRNSVKSSF HDPKLKGKPS
201  RERYVTHNRA HW
```

Fig. 91

```
1    APETAVLGAE LSAVGENGGE KPTPSPPWRL RRSKRCSCSS LMDKECVYFC
51   HLDIIWVNTP EHVVPYGLGS PRSKRALENL LPTKATDREN RCQCASQKDK
101  KCWNFCQAGK ELRAEDIMEK DWNNHKKGKD CSKLGKKCIY QQLVRGRKTR
151  RSSEEHLRQT RSETMRNSVK SSFHDPKLKG KPSRERYVTH NRAHW
```

Fig. 92

```
1    CSCSSLMDKE CVYFCHLDII W
```

Fig. 93

```
1    RSSEEHLRQT RSETMRNSVK SSFHDPKLKG KPSRERYVTH NRAHW
```

Fig. 94

```
1    CSCSSLMDKE CVYFCHLDII WVNTPEHVVP YGLGSPRS
```

Fig. 95

```
1    MGFQKFSPFL ALSILVLLQA GSLHAAPFRS ALESSPADPA TLSEDEARLL
51   LAALVQDYVQ MKASELEQEQ EREGSSLDSP RSKRCGNLST CMLGTYTQDF
101  NKFHTFPQTA IGVGAPGKKR DMSSDLERDH RPHVSMPQNA N
```

Fig. 96

```
1    APFRSALESS PADPATLSED EARLLLAALV QDYVQMKASE LEQEQEREGS
51   SLDSPRSKRC GNLSTCMLGT YTQDFNKFHT FPQTAIGVGA PGKKRDMSSD
101  LERDHRPHVS MPQNAN
```

Fig. 97

```
1    APFRSALESS PADPATLSED EARLLLAALV QDYVQMKASE LEQEQEREGS
51   SLDSPRS
```

Fig. 98

```
1    CGNLSTCMLG TYTQDFNKFH TFPQTAIGVG AP
```

Fig. 99

1    DMSSDLERDH RPHVSMPQNA N

Fig. 100

1      MDPQTAPSRA LLLLLFLHLA FLGGRSHPLG SPGSASDLET SGLQEQRNHL
51     QGKLSELQVE QTSLEPLQES PRPTGVWKSR EVATEGIRGH RKMVLYTLRA
101    PRSPKMVQGS GCFGRKMDRI SSSSGLGCKV LRRH

Fig. 101

1      HPLGSPGSAS DLETSGLQEQ RNHLQGKLSE LQVEQTSLEP LQESPRPTGV
51     WKSREVATEG IRGHRKMVLY TLRAPRSPKM VQGSGCFGRK MDRISSSSGL
101    GCKVLRRH

Fig. 102

1      HPLGSPGSAS DLETSGLQEQ RNHLQGKLSE LQVEQTSLEP LQESPRPTGV
51     WKSREVATEG IRGHRKMVLY TLRAPR

Fig. 103

1      SPKMVQGSGC FGRKMDRISS SSGLGCKVLR RH

SEQUENCE LISTING

<160> NUMBER OF SEQ ID NOS: 29

<210> SEQ ID NO 1
<211> LENGTH: 185
<212> TYPE: PRT
<213> ORGANISM: Homo sapiens

<400> SEQUENCE: 1

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

<210> SEQ ID NO 2
<211> LENGTH: 164
<212> TYPE: PRT
<213> ORGANISM: Homo sapiens

<400> SEQUENCE: 2

```
Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
        35                  40                  45
```

Pro Gln Asp Met Lys Gly Ala Ser Arg Ser Pro Glu Asp Ser Ser Pro
    50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
                100                 105                 110

Asn Val Ala Pro Arg Ser Lys Ile Ser Pro Gln Gly Tyr Gly Arg Arg
                115                 120                 125

Arg Arg Arg Ser Leu Pro Glu Ala Gly Pro Gly Arg Thr Leu Val Ser
    130                 135                 140

Ser Lys Pro Gln Ala His Gly Ala Pro Ala Pro Pro Ser Gly Ser Ala
145                 150                 155                 160

Pro His Phe Leu

<210> SEQ ID NO 3
<211> LENGTH: 20
<212> TYPE: PRT
<213> ORGANISM: Homo sapiens

<400> SEQUENCE: 3

Ala Arg Leu Asp Val Ala Ser Glu Phe Arg Lys Lys Trp Asn Lys Trp
1               5                   10                  15

Ala Leu Ser Arg
            20

<210> SEQ ID NO 4
<211> LENGTH: 40
<212> TYPE: PRT
<213> ORGANISM: Homo sapiens

<400> SEQUENCE: 4

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
                20                  25                  30

Ser Arg Ser Pro Glu Asp Ser Ser
            35                  40

<210> SEQ ID NO 5
<211> LENGTH: 52
<212> TYPE: PRT
<213> ORGANISM: Homo sapiens

<400> SEQUENCE: 5

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
    50

<210> SEQ ID NO 6
<211> LENGTH: 153
<212> TYPE: PRT
<213> ORGANISM: Homo sapiens

<400> SEQUENCE: 6

```
Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr Arg Arg
145                 150
```

<210> SEQ ID NO 7
<211> LENGTH: 126
<212> TYPE: PRT
<213> ORGANISM: Homo sapiens

<400> SEQUENCE: 7

```
Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr
        115                 120                 125
```

<210> SEQ ID NO 8
<211> LENGTH: 28
<212> TYPE: PRT
<213> ORGANISM: Homo sapiens

<400> SEQUENCE: 8

```
Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25
```

```
<210> SEQ ID NO 9
<211> LENGTH: 98
<212> TYPE: PRT
<213> ORGANISM: Homo sapiens

<400> SEQUENCE: 9

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
                20                  25                  30

Val Pro Pro Gln Val Leu Ser Glu Pro Asn Glu Glu Ala Gly Ala Ala
            35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg

<210> SEQ ID NO 10
<211> LENGTH: 38
<212> TYPE: PRT
<213> ORGANISM: Homo sapiens

<400> SEQUENCE: 10

Pro Glu Val Pro Pro Trp Thr Gly Glu Val Ser Pro Ala Gln Arg Asp
1               5                   10                  15

Gly Gly Ala Leu Gly Arg Gly Pro Trp Asp Ser Ser Asp Arg Ser Ala
                20                  25                  30

Leu Leu Lys Ser Lys Leu
                35

<210> SEQ ID NO 11
<211> LENGTH: 164
<212> TYPE: PRT
<213> ORGANISM: Homo sapiens

<400> SEQUENCE: 11

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
                20                  25                  30

Met Ser Asp Leu Glu Leu Arg Gln Cys Leu Pro Cys Gly Pro Gly Gly
                35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140
```

-continued

```
Arg Leu Val Gln Leu Ala Gly Ala Pro Glu Pro Phe Glu Pro Ala Gln
145                 150                 155                 160

Pro Asp Ala Tyr

<210> SEQ ID NO 12
<211> LENGTH: 145
<212> TYPE: PRT
<213> ORGANISM: Homo sapiens

<400> SEQUENCE: 12

Cys Tyr Phe Gln Asn Cys Pro Arg Gly Gly Lys Arg Ala Met Ser Asp
1               5                   10                  15

Leu Glu Leu Arg Gln Cys Leu Pro Cys Gly Pro Gly Gly Lys Gly Arg
                20                  25                  30

Cys Phe Gly Pro Ser Ile Cys Cys Ala Asp Glu Leu Gly Cys Phe Val
            35                  40                  45

Gly Thr Ala Glu Ala Leu Arg Cys Gln Glu Glu Asn Tyr Leu Pro Ser
    50                  55                  60

Pro Cys Gln Ser Gly Gln Lys Ala Cys Gly Ser Gly Gly Arg Cys Ala
65                  70                  75                  80

Ala Phe Gly Val Cys Cys Asn Asp Glu Ser Cys Val Thr Glu Pro Glu
                85                  90                  95

Cys Arg Glu Gly Phe His Arg Arg Ala Arg Ala Ser Asp Arg Ser Asn
            100                 105                 110

Ala Thr Gln Leu Asp Gly Pro Ala Gly Ala Leu Leu Leu Arg Leu Val
        115                 120                 125

Gln Leu Ala Gly Ala Pro Glu Pro Phe Glu Pro Ala Gln Pro Asp Ala
    130                 135                 140

Tyr
145

<210> SEQ ID NO 13
<211> LENGTH: 9
<212> TYPE: PRT
<213> ORGANISM: Homo sapiens

<400> SEQUENCE: 13

Cys Tyr Phe Gln Asn Cys Pro Arg Gly
1               5

<210> SEQ ID NO 14
<211> LENGTH: 39
<212> TYPE: PRT
<213> ORGANISM: Homo sapiens

<400> SEQUENCE: 14

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
                20                  25                  30

Pro Ala Gln Pro Asp Ala Tyr
        35

<210> SEQ ID NO 15
<211> LENGTH: 93
<212> TYPE: PRT
<213> ORGANISM: Homo sapiens

<400> SEQUENCE: 15
```

Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
            20                  25                  30

Gly Cys Phe Val Gly Thr Ala Glu Ala Leu Arg Cys Gln Glu Glu Asn
        35                  40                  45

Tyr Leu Pro Ser Pro Cys Gln Ser Gly Gln Lys Ala Cys Gly Ser Gly
    50                  55                  60

Gly Arg Cys Ala Ala Phe Gly Val Cys Cys Asn Asp Glu Ser Cys Val
65                  70                  75                  80

Thr Glu Pro Glu Cys Arg Glu Gly Phe His Arg Ala
                85                  90

<210> SEQ ID NO 16
<211> LENGTH: 212
<212> TYPE: PRT
<213> ORGANISM: Homo sapiens

<400> SEQUENCE: 16

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210

<210> SEQ ID NO 17
<211> LENGTH: 195
<212> TYPE: PRT
<213> ORGANISM: Homo sapiens

<400> SEQUENCE: 17

Ala Pro Glu Thr Ala Val Leu Gly Ala Glu Leu Ser Ala Val Gly Glu
1               5                   10                  15

Asn Gly Gly Glu Lys Pro Thr Pro Ser Pro Pro Trp Arg Leu Arg Arg
            20                  25                  30

Ser Lys Arg Cys Ser Cys Ser Ser Leu Met Asp Lys Glu Cys Val Tyr
        35                  40                  45

Phe Cys His Leu Asp Ile Ile Trp Val Asn Thr Pro Glu His Val Val
50                  55                  60

Pro Tyr Gly Leu Gly Ser Pro Arg Ser Lys Arg Ala Leu Glu Asn Leu
65                  70                  75                  80

Leu Pro Thr Lys Ala Thr Asp Arg Glu Asn Arg Cys Gln Cys Ala Ser
                85                  90                  95

Gln Lys Asp Lys Lys Cys Trp Asn Phe Cys Gln Ala Gly Lys Glu Leu
            100                 105                 110

Arg Ala Glu Asp Ile Met Glu Lys Asp Trp Asn Asn His Lys Lys Gly
        115                 120                 125

Lys Asp Cys Ser Lys Leu Gly Lys Lys Cys Ile Tyr Gln Gln Leu Val
130                 135                 140

Arg Gly Arg Lys Ile Arg Arg Ser Ser Glu Glu His Leu Arg Gln Thr
145                 150                 155                 160

Arg Ser Glu Thr Met Arg Asn Ser Val Lys Ser Ser Phe His Asp Pro
                165                 170                 175

Lys Leu Lys Gly Lys Pro Ser Arg Glu Arg Tyr Val Thr His Asn Arg
            180                 185                 190

Ala His Trp
        195

<210> SEQ ID NO 18
<211> LENGTH: 21
<212> TYPE: PRT
<213> ORGANISM: Homo sapiens

<400> SEQUENCE: 18

Cys Ser Cys Ser Ser Leu Met Asp Lys Glu Cys Val Tyr Phe Cys His
1               5                   10                  15

Leu Asp Ile Ile Trp
            20

<210> SEQ ID NO 19
<211> LENGTH: 45
<212> TYPE: PRT
<213> ORGANISM: Homo sapiens

<400> SEQUENCE: 19

Arg Ser Ser Glu Glu His Leu Arg Gln Thr Arg Ser Glu Thr Met Arg
1               5                   10                  15

Asn Ser Val Lys Ser Ser Phe His Asp Pro Lys Leu Lys Gly Lys Pro
            20                  25                  30

Ser Arg Glu Arg Tyr Val Thr His Asn Arg Ala His Trp
        35                  40                  45

<210> SEQ ID NO 20
<211> LENGTH: 38
<212> TYPE: PRT
<213> ORGANISM: Homo sapiens

<400> SEQUENCE: 20

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Pro Tyr Gly
            20                  25                  30

Leu Gly Ser Pro Arg Ser
            35

<210> SEQ ID NO 21
<211> LENGTH: 141
<212> TYPE: PRT
<213> ORGANISM: Homo sapiens

<400> SEQUENCE: 21

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala Asn
    130                 135                 140

<210> SEQ ID NO 22
<211> LENGTH: 116
<212> TYPE: PRT
<213> ORGANISM: Homo sapiens

<400> SEQUENCE: 22

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 23
<211> LENGTH: 57
<212> TYPE: PRT
<213> ORGANISM: Homo sapiens

```
<400> SEQUENCE: 23

Ala Pro Phe Arg Ser Ala Leu Glu Ser Pro Ala Asp Pro Ala Thr
1               5                  10                 15

Leu Ser Glu Asp Glu Ala Arg Leu Leu Leu Ala Ala Leu Val Gln Asp
                20                  25                  30

Tyr Val Gln Met Lys Ala Ser Glu Leu Glu Gln Glu Gln Glu Arg Glu
                35                  40                  45

Gly Ser Ser Leu Asp Ser Pro Arg Ser
            50                  55

<210> SEQ ID NO 24
<211> LENGTH: 32
<212> TYPE: PRT
<213> ORGANISM: Homo sapiens

<400> SEQUENCE: 24

Cys Gly Asn Leu Ser Thr Cys Met Leu Gly Thr Tyr Thr Gln Asp Phe
1               5                  10                 15

Asn Lys Phe His Thr Phe Pro Gln Thr Ala Ile Gly Val Gly Ala Pro
                20                  25                  30

<210> SEQ ID NO 25
<211> LENGTH: 21
<212> TYPE: PRT
<213> ORGANISM: Homo sapiens

<400> SEQUENCE: 25

Asp Met Ser Ser Asp Leu Glu Arg Asp His Arg Pro His Val Ser Met
1               5                  10                 15

Pro Gln Asn Ala Asn
                20

<210> SEQ ID NO 26
<211> LENGTH: 134
<212> TYPE: PRT
<213> ORGANISM: Homo sapiens

<400> SEQUENCE: 26

Met Asp Pro Gln Thr Ala Pro Ser Arg Ala Leu Leu Leu Leu Leu Phe
1               5                  10                 15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
                100                 105                 110

Phe Gly Arg Lys Met Asp Arg Ile Ser Ser Ser Ser Gly Leu Gly Cys
            115                 120                 125

Lys Val Leu Arg Arg His
        130

<210> SEQ ID NO 27
```

```
<211> LENGTH: 108
<212> TYPE: PRT
<213> ORGANISM: Homo sapiens

<400> SEQUENCE: 27

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 28
<211> LENGTH: 76
<212> TYPE: PRT
<213> ORGANISM: Homo sapiens

<400> SEQUENCE: 28

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 29
<211> LENGTH: 32
<212> TYPE: PRT
<213> ORGANISM: Homo sapiens

<400> SEQUENCE: 29

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

PROGNOSIS AND RISK ASSESSMENT IN STROKE PATIENTS BY DETERMINING THE LEVEL OF MARKER PEPTIDES

SEQUENCE LISTING

The instant application contains a Sequence Listing which has been submitted electronically in ASCII format and is hereby incorporated by reference in its entirety. Said ASCII copy, created on Apr. 6, 2018, is named Voss-0066-D01_SL.txt and is 24,408 bytes in size.

FIELD OF THE INVENTION

The present invention is in the field of clinical diagnostics. Particularly the present invention relates to outcome prognosis and risk assessment in stroke patients by determination of the level of marker peptides.

BACKGROUND OF THE INVENTION

Stroke is defined as an acute focal neurological deficit resulting from a cerebrovascular disease. The two main types of stroke are ischemic and hemorrhagic, accounting for approximately 85% and 15%, respectively (Hickey 2003. *The clinical practice of neurological and neurosurgical nursing* (5$^{th}$ ed.). Philadelphia: Lippincott, Williams & Wilkins). When an ischemic stroke occurs, the blood supply to the brain is interrupted, and brain cells are deprived of glucose and oxygen. Approximately 45% of ischemic strokes are caused by small or large artery thrombus, 20% are embolic origin, and others have an unknown cause (Hickey 2003. *The clinical practice of neurological and neurosurgical nursing* (5$^{th}$ ed.). Philadelphia: Lippincott, Williams & Wilkins).

Transient ischemic attack (TIA) (also known as "mini-stroke") is a syndrome characterized by the sudden onset of discrete neurological symptoms that resolve completely within 24 hours. TIA may be reported by 0.5-8% of the elderly population (Bots et al., 1997. *Stroke* 28(4): 768-73). A patient representing with a TIA is at high risk of subsequent adverse events. The 90-day risk of stroke has been reported to be greater than 10%, with the highest risk occurring within the first 2 days (Jonston et al., 2003. *Neurology* 60: 1429-34).

Stroke is one of the most important vascular diseases. Stroke remains the second leading cause of death worldwide and is one of the main causes of adult disability and early invalidity in Europe (Murray and Lopez, 1997. *Lancet* 349: 1269-76; Murray and Lopez 1997. *Lancet* 349:1498-504). In the US more than 700 000 people have a stroke each year, whereof 550 000 are first strokes (Thom et al. 2006. *Heart disease and stroke statistics—2006 update: A report from the American Heart Association Statistics Committee and Stroke Statistics Subcommittee. Circulation* 113: 85-151). Therefore, it is an important public health problem and a burden to health care providers and to the community at large because of the amount of effort that has to be invested in the planning and provision of healthcare.

The incidence of stroke increases markedly with increasing age in our society (Modan and Wagener, 1992. *Stroke* 23:1230-36). Most ischemic strokes occur between the ages of 71 an 80 years while most hemorrhagic strokes between 60 and 70 years appear (Colombo et al., 1989. *Rivista de Neurologia* 59: 1-7).

Neuroradiological imaging methods like computer tomography (CT) or magnetic resonance tomography (MRT) are used for diagnosis of stroke. CT scanning is recommended for patients suffering from acute stroke caused by cerebral haemorrhage. This method, however, is less effective in patients suffering from an acute ischemic insult (sensitivity less than 33%). Doppler sonography and digital subtraction angiography (DSA) can additionally be used to determine the causes of acute circulatory disturbances.

Treatment of ischemic stroke is normally focussed on supporting vital functions and on rehabilitative measures. Therapies are aimed at removing the blockage by breaking the clot or by removing it mechanically, minimizing clot enlargement and preventing new clots from forming. Thrombolysis (breakdown of blood clots) can be induced by applying plasminogen activator (tPA or PLAT) within the first 3 hours after the stroke. Since some disease states like hypoglycaemia, migraine, cerebral haemorrhage and certain brain tumours have similar symptoms as acute ischemic stroke, there is a need for rapid differential diagnosis.

Therapy also needs to be adjusted according to the patients individual situation, e.g. the individual prognosis and/or the individual risk of further strokes.

Prognosis of the outcome for stroke patients after a defined interval can either be functional or related to individual survival. For functional outcome prognosis the morbidity of a patient after a defined time is determined using a score system such as the modified Rankin_Scale (mRS; Bonita and Beaglehole, 1988. *Modification of Rankin Scale: Recovery of motor function after stroke. Stroke* 19: 1497-1500) or the National Institutes of Health Stroke Scale (NIHSS; Adams et al., 1999. *Baseline NIH Stroke Scale score strongly predicts outcome after stroke: A report of the Trial of Org* 10172 *in Acute Stroke Treatment (TOAST). Neurology* 53: 126-31), the NIHSS currently being the gold standard. The functional outcome may also be expressed in terms of need of nursing care or with respect to activities of daily living (ADL), e.g. according to the Barthel Index and Rankin Scale (Collin et al., 1988. *The Barthel ADL Index: a reliability study. International Disability Study* 10: 61-3; Bonita and Beaglehole, 1988. *Modification of Rankin Scale: Recovery of motor function after stroke. Stroke* 19: 1497-1500). Some biomarkers have been reported to be indicative for future cardiovascular events, e.g. a further stroke. Potential stroke biomarkers that have been reported are S-100B (Serum protein 100 Beta; Stranjalis et al. 2007 *Acta Neurochir (Wien)* 149: 231-7; Foerch et al. 2005. *Arch Neurol* 62: 1130-4), NSE (neuronenspezifische Enolase; Anand and Staed 2005. *Cerebrovasc Dis* 20: 213-9), GFAP (glial fibrillary acidic protein; Nylen et al., 2007. *Stroke* 38: 1489-94), CRP (C-reactive protein; Di Napoli et al. 2001. *Stroke* 32: 133-8; Di Napoli et al. 2001. *Stroke* 32: 917-24), IL-6 (Interleukin-6; Orion et al. 2008. *Eur J Neurol* 15:323-8; Shenhar-Tsarfaty et al., 2007. *Thromb Res* 122:167-73), and Plasma-Fibrinogen (Turaj et al. 2006. *J Neurol Sci* 246: 13-9).

N-terminal proBNP (NT-proBNP) has been shown to be an independent variable for individual survival prognosis after an ischemic stroke (Jensen et al. 2006. *Cerebrovasc Dis* 22: 439-44; Sharma et al. 2006. *J Stroke Cerebrovasc Dis* 15: 121-7; Mäkikallio et al. 2005. *Stroke* 36: 1016-20; Yip et al. 2006. *Circ J* 70: 447-52) and after an hemorrhagic stroke (Sharma et al. 2006. *J Stroke Cerebrovasc Dis* 15: 121-7).

The levels of mature ANP (Estrada et al. 1994. *Am J Hypertens* 7: 1085-9) and ADM (Hosomi et al. 2004. *J Hypertens* 22: 1945-51) have been determined in samples of patients with ischemic stroke. However, no correlation of the ANP concentrations with the neurological status (Mathew's modified scale) or outcome could be shown.

Elevated ET-1 concentrations have been found in the blood of stroke patients without investigating the prognostic value of these data (Ziv et al. 1992 *Stroke* 23: 1014-6; Alioglu et al. 2002. *Angiology* 53: 77-82; Giannopoulos et al. 2008. *Neurol. Res.* 30(7):727-30). ET-1 levels have been found to be elevated in patients after an ischemic stroke (Estrada et al. 1994. *Am J Hypertens* 7: 1085-9) but no correlation with the rate of survival has been determined.

An investigation of the serum Procalcitonin (PCT) levels of patients suffering from an acute stroke (Miyakis et al. 2004. *Clin Chim Acta* 350: 437-9) did not reveal significant differences of the levels at the day of hospitalization and day 7. No correlation of the PCT levels with mortality or neurological outcome has been found in this study.

Human growth hormone (hGH) is a polypeptide produced by the somatotrope cells in the pituitary. It is secreted in a pulsatile fashion (10 to 20 pulses in each 24-hour cycle) and its secretion is regulated by three hypothalamic peptides, growth hormone releasing hormone (GHRH) and ghrelin, which stimulate hGH secretion, and somatostatin, which inhibits hGH secretion by back regulation (Kato et al. 2002. *Regulation of human growth hormone secretion and its disorders. Internal Med* 41: 7-13).

HGH is heterogenous, consisting of several molecular isoforms and fragments (Baumann G. 1991. *Growth hormone heterogeneity: genes, isohormones, variants and binding proteins. Endocr Rev* 12: 424-449). Four major isoforms of hGH have been identified in the human pituitary ranging in the amino acid number and include 191 aa (frequency of 87.5%), 176 aa (8.1%), 153 aa (3.3%) and 145 aa (11%) (Zhan X. et al. 2005. *Proteomics analysis of growth hormone isoforms in the human pituitary. Proteomics* 5: 1228-41). The 191 aa form has a molecular weight of 22 kDa and is co-secreted from the anterior pituitary gland with the 176 aa form (20 kDa isoform), lacking the amino acid residues 32 to 46 (De Palo E. et al. 2006. *Growth hormone isoforms and segments/fragments: molecular structure and laboratory measurements. Clin Chim Acta* 365: 67-76).

The secretion of hGH is slightly higher in women than in men, with the highest levels observed at puberty. Secretion decreases with age by around 14% per decade. Moreover secretion varies with normal physiological and pathophysiological conditions. The principal physiological regulation mechanisms of hGH secretion are neural endogenous rhythm, sleep, stress, exercise, and nutritional and metabolic signals: hGH levels are higher during slow wave sleep (typically one to two hours after falling asleep) and are increased by exercise, stress, fever, fasting and with some amino acids (leucine and argininin). HGH secretion is also stimulated by insulin-induced hypoglycaemia, L-dopa, clonidine (α2-adrenergic agonist), γ-hydroxybutyrate and β-adrenergic blocking agents, whereas oral administration of glucose and increased serum free fatty acid levels rather suppress hGH secretion. hGH secretion is also blunted in obesity and by aging. (Review in: Kato et al. 2002. *Regulation of human growth hormone secretion and its disorders. Internal Med* 41: 7-13).

C-reactive protein (CRP) is a plasma protein that was originally discovered by Tillett and Francis in 1930 as a substance in the serum of patients with acute inflammation that reacted with the C polysaccharide of pneumococcus. Patients with elevated basal levels of CRP have been shown to have an increased risk for diabetes, hypertension and cardiovascular disease (Pradhan et al. (2001. *JAMA* 286: 327-334; Dehghan. 2007, *Diabetes* 56: 872).

Troponin is a complex of three regulatory proteins that is integral to muscle contraction in skeletal and cardiac muscle, but not smooth muscle. Troponin has three subunits: TnC, TnI, and TnT. Individual subunits serve different functions: Troponin C (TnC) binds to calcium ions to produce a conformational change in TnI. Troponin T binds to tropomyosin, interlocking them to form a troponin-tropomyosin complex. Troponin I binds to actin in thin myofilaments to hold the troponin-tropomyosin complex in place. Certain subtypes of troponin (cardiac troponin I and T) are very sensitive and specific indicators of damage to the heart muscle (myocardium). Their level in blood samples can be used to differentiate between unstable angina and myocardial infarction (heart attack) in patients with chest pain (Antman et al. 1996. *N Engl J Med;* 335:1342-9).

SUMMARY OF THE INVENTION

A subject of the present invention is the provision of an improved method for prognosis of an outcome or assessing the risk of a patient having suffered a stroke or a transient ischemic attack, comprising determining the level of at least one marker peptide in a sample of said patient.

The present invention relates to a method for prognosis of an outcome or assessing the risk of a patient having suffered a stroke or a transient ischemic attack, comprising the following steps:
  a) providing a sample from said patient,
  b) determining the level of at least one marker peptide in said sample said marker peptide selected from the group comprising ANP, AVP, ADM, ET-1, Calcitonin, troponin, CRP and hGH or fragments thereof or its precursor or fragments thereof,
  c) correlating the level of said at least one marker peptides or fragments thereof or its precursor or fragments thereof with the prognosis of an outcome or assessing the risk for said patient.

The invention also pertains to the use of the methods of the invention for prognosis of an outcome or assessing the risk of a patient having suffered a stroke or a transient ischemic attack.

DETAILED DESCRIPTION OF THE INVENTION

The present invention relates to a method for prognosis of an outcome or assessing the risk of a patient having suffered a stroke or a transient ischemic attack, comprising the following steps:
  a. providing a sample from said patient,
  b. determining the level of at least one marker peptide in said sample said marker peptide selected from the group comprising ANP, AVP, ADM, ET-1, Calcitonin, troponin, CRP and hGH or fragments thereof or its precursor or fragments thereof,
  c. correlating the level of said at least one marker peptides or fragments thereof or its precursor or fragments thereof with the prognosis of an outcome or assessing the risk for said patient.

Preferred marker peptides according to the present invention are ANP, BNP, AVP, ADM, ET-1, Calcitonin, troponin, CRP (C-reactive protein) and hGH. Particularly preferred marker peptides are ANP, BNP, AVP, ADM, ET-1, Calcitonin and hGH. These peptides can also be classified into subsets according to their origin and/or place of synthesis within the body or according to the main site of action or according to functional properties: ANP, BNP and troponin (cT) are cardiovascular peptides, ET-1 and ADM are endothelial peptides, AVP (including e.g. copeptin) and hGH are pituitary peptides, whereas PCT and CRP are inflammatory peptides.

Troponin and CRP (C-reactive protein) are proteins or protein complexes, i.e. polypeptides. In the context of the present invention they are like the other peptides mentioned also referred to as marker peptides.

The term "marker peptides" in the context of the present invention thus relates to the cardiovascular, inflammatory and/or pituitary peptides of the invention.

In a preferred embodiment of the invention said sample has been taken pre-interventionally from said patient. In another preferred embodiment of the invention, said sample has been taken post-interventionally from said patient.

The terms "pre-interventionally", "pre-interventional" and "before intervention" herein relate to the time before intervention for the treatment of the stroke or TIA has been started. By "intervention" any medical intervention used to modify a health outcome is meant. This definition includes drug administration, surgical procedures, application of devices, behavioural treatments, process-of-care changes, and the like. Preferably, the sample is taken upon admission of the patient to a hospital or before the diagnosis of stroke or TIA has been confirmed. The terms "post-interventionally", "post-interventional" and "after intervention" relate to the time after intervention or the treatment has been started.

The levels of the markers as obtained by the methods or the use of the assays according to the present invention may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In certain embodiments, particular thresholds for one or more markers in a panel are not relied upon to determine if a profile of marker levels obtained from a subject is indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. As discussed herein, that pattern of changes may be obtained from a single sample, or from temporal changes in one or more members of the panel (or a panel response value). A panel herein refers to a set of markers.

As described herein after, a panel response value is preferably determined by plotting ROC curves for the sensitivity (i.e. true positives) of a particular panel of markers versus 1-(specificity) (i.e. false positives) for the panel at various cut-offs. In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The term "patient" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

The term "correlating," as used herein in reference to the use of diagnostic and prognostic markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a panel of marker levels is correlated to a global probability or a particular outcome.

Preferably, said outcome or said risk regards survival and/or a functional outcome and/or a re-stroke or a re-transient ischemic attack.

The invention also pertains to a method for the stratification of a patient into risk groups said patient having suffered a stroke or a transient ischemic attack and said method comprising the steps as described above.

ANP in the context of the present invention relates to atrial natriuretic peptide or fragments thereof or precursors or fragments thereof. A preferred fragment of a precursor of ANP is mid-regional proANP (MR-proANP). Mid-regional proANP (MR-proANP) is defined as proANP or any fragment thereof comprising at least amino acid residues 53-90 of proANP. MR-proANP$_{53-90}$ is a particularly preferred marker peptide in the context of the present invention.

AVP in the context of the present invention relates to arginine vasopressin (=vasopressin) or fragments thereof or precursors or fragments thereof. A preferred fragment of a precursor of AVP is C-terminal proAVP (CT-proAVP or Copeptin). CT-proAVP$_{107-145}$ (or CT-pre-proAVP$_{126-164}$) is a particularly preferred marker peptide in the context of the present invention.

ADM in the context of the present invention relates to adrenomedullin or fragments thereof or precursors or fragments thereof. A preferred fragment of a precursor of ADM is mid-regional proADM (MR-proADM). MR-proADM$_{24-71}$ (or MR-preproADM$_{45-92}$) is a particularly preferred marker peptide in the context of the present invention.

ET-1 in the context of the present invention relates to endothelin 1 or fragments thereof or precursors or fragments thereof. A preferred fragment of a precursor of ET-1 is C-terminal-proET1 (CT-proET1). CT-proET-1$_{151-195}$ (or CT-preproET-1$_{168-212}$) is a particularly preferred marker peptide in the context of the present invention.

Calcitonin in the context of the present invention also relates to fragments thereof or precursors or fragments thereof. A preferred precursor of Calcitonin is procalcitonin (PCT). PCT in the context of the present invention relates to procalcitonin comprising the amino acids 1-116, 2-116, or 3-116 or fragments thereof. Procalcitonin may comprise posttranslational modifications such as glycosylation, liposidation or derivatisation.

hGH in the context of the present invention relates to human growth hormone or fragments thereof or precursors or fragments thereof. hGH is a particularly preferred pituitary peptide in the context of the present invention.

"Fragments" of the marker peptides relate to fragments of at least 12 amino acids in length, preferably at least six amino acid residues in length.

Furthermore, the invention relates to a method for diagnosing a patient who is under suspect of having a stroke or a transient ischemic attack or who shows symptoms at least similar to stroke or a transient ischemic attack comprising
  a. providing a sample from said patient,
  b. determining the level of at least one marker peptide in said sample said marker peptide selected from the group comprising ANP, AVP, ADM, ET-1, Calcitonin and hGH or fragments thereof or its precursor or fragments thereof
  c. determining whether said patient is suffering from stroke or a transient ischemic attack based on the level of said at least one marker peptide.

Symptoms of stroke or similar to stroke may for example comprise hemiplegia, muscle weakness of the face, numbness and reduction in sensory or vibratory sensation. In most cases, the symptoms affect only one side of the body (unilateral). Depending on the cause of the stroke, symptoms may also comprise one or more of the following symptoms: altered smell, taste, hearing, or vision (total or partial), drooping of eyelid (ptosis) and weakness of ocular muscles, decreased reflexes (e.g. gag, swallow, pupil reactivity to light), decreased sensation and muscle weakness of the face, balance problems and nystagmus, altered breathing and heart rate, weakness in sternocleidomastoid muscle with inability to turn head to one side, weakness in tongue (inability to protrude and/or move from side to side), aphasia (inability to speak or understand language from involvement of Broca's or Wernicke's area), apraxia (altered voluntary movements), visual field defect, memory deficits (involvement of temporal lobe), hemineglect (involvement of parietal lobe), disorganized thinking, confusion, hypersexual gestures (with involvement of frontal lobe), anosognosia (persistent denial of the existence of a, usually stroke-related, deficit), trouble walking, altered movement coordination, vertigo and or disequilibrium.

Preferably, the level of said at least one marker peptide is attributed to either ischemic stroke or hemorrhagic stroke or a transient ischemic attack. The term "level" in the context of the present invention relates to the concentration (preferably expressed as weight/volume; w/v) of marker peptides in a sample taken from a patient.

As outlined above, the marker peptides of the present invention also relate to fragments thereof or precursor peptides or fragments thereof. The marker peptides also include the prohormones or pre-prohormones or fragments thereof, particularly the prohormones and fragments thereof. Preferably in the context of the present invention ANP is proANP, most preferably MR-proANP. Preferably AVP is proAVP, more preferably CT-proAVP, most preferably CT-proAVP$_{107-145}$ and fragments thereof. Preferably ADM is proADM, more preferably MR-proADM, most preferably MR-proADM$_{24-71}$ and fragments thereof. Preferably ET-1 is proET-1, more preferably CT-proET-1, most preferably CT-proET-1$_{151-195}$ and fragments thereof. Preferably Calcitonin is PCT$_{1-116}$ and fragments thereof.

In one preferred embodiment of the invention the marker peptide is selected from the group comprising ANP, AVP, ADM, ET-1 and Calcitonin.

In another preferred embodiment of the invention of the invention the marker peptide is selected from the group comprising ANP, AVP, ADM, ET-1 and hGH.

In another preferred embodiment of the invention of the invention the marker peptide is selected from the group comprising ANP, AVP, ADM and ET-1.

In another preferred embodiment of the invention of the invention the marker peptide is selected from the group comprising ANP, AVP and ADM.

In yet another preferred embodiment of the invention of the invention the marker peptide is selected from the group comprising ANP and ADM.

In yet another preferred embodiment of the invention of the invention the marker peptide is selected from the group comprising ANP, ADM, ET-1, Calcitonin and hGH.

In yet another preferred embodiment of the invention of the invention the marker peptide is selected from the group comprising ANP, ADM and ET-1.

In a particularly preferred embodiment of the invention the marker peptide is selected from the group comprising MR-proANP, C-terminal proAVP (Copeptin), MR-proADM, CT-proET-1, PCT and hGH.

In another particularly preferred embodiment the marker peptide is selected from the group comprising MR-proANP, MR-proADM and CT-proET-1.

In another preferred embodiment of the invention the marker peptide is selected from the group comprising MR-proANP, C-terminal proAVP (Copeptin), MR-proADM and CT-proET-1.

In yet another preferred embodiment of the invention the marker peptide is selected from the group comprising MR-proANP, MR-proADM, PCT and hGH.

In yet another preferred embodiment of the invention the marker peptide is selected from the group comprising MR-proANP, C-terminal proAVP (Copeptin), MR-proADM, CT-proET-1 and hGH.

In yet another preferred embodiment of the invention the marker peptide is selected from the group comprising MR-proANP, MR-proADM, CT-proET-1, PCT and hGH.

In a preferred embodiment of the methods of the invention, the marker peptide is proANP. Preferably, the level of marker peptide is determined by detecting mid-regional proANP.

In a preferred embodiment of the methods of the invention, the marker peptide is proAVP. Preferably, the level of marker peptide is determined by detecting C-terminal proAVP.

In a preferred embodiment of the methods of the invention, the marker peptide is proADM. Preferably, the level of marker peptide is determined by detecting mid-regional proADM.

In a preferred embodiment of the methods of the invention, the marker peptide is proET-1. Preferably, the level of marker peptide is determined by detecting C-terminal proET-1.

In a preferred embodiment of the methods of the invention, the marker peptide is PCT. Preferably, the level of marker peptide is determined by detecting PCT.

In a preferred embodiment of the methods of the invention, the marker peptide is hGH. Preferably, the level of marker peptide is determined by detecting hGH.

In a preferred embodiment of the invention, a combination of two or more cardiovascular marker is used. Preferably herein, the second or further cardiovascular marker is selected from the group comprising ANP, BNP, AVP, ADM, ET-1, Calcitonin and hGH.

Optionally the level of BNP or fragments thereof or a precursor or fragments thereof is additionally determined.

BNP in the context of the present invention relates to brain natriuretic peptide or fragments thereof or precursors or fragments thereof. A preferred fragment of a precursor of BNP is N-terminal proBNP (NT-proBNP). NT-proBNP is a particularly preferred marker peptide in the context of the present invention.

In a preferred embodiment of the invention, the level of more than one cardiovascular marker is determined and the result for each individual marker are differently weighted for prognosis of an outcome or assessing the risk of a patient having suffered a stroke or a transient ischemic attack. It is particularly preferred that the level of a set of two or more marker peptides is determined, most preferably the level of a set of two marker peptides is determined.

The determination of the level of more than one marker peptide in the sample leads to a higher probability as compared to a single marker for the prognosis of an outcome or assessing the risk for the patient.

A particular embodiment of the invention relates to the method for prognosis of an outcome or assessing the risk of a patient having suffered a stroke or a transient ischemic attack according to the present invention, wherein the level of at least two marker peptides is determined and wherein each marker peptide is selected from a different subset of peptides selected from the group comprising cardiac peptides, endothelial peptides, pituitary peptides and inflammatory peptides, wherein the cardiac peptides are selected from the group comprising ANP, BNP and troponin (cT), the endothelial peptides are selected from the group comprising ET-1 and ADM, the pituitary peptides are selected from the group comprising AVP and hGH and the inflammatory peptides are selected from the group comprising PCT and CRP.

In another preferred embodiment the level of two, three, four, five, six, seven, eight or nine marker peptides in the sample is determined.

Most preferably the level of a set of at least two marker peptides is determined and the set of the at least two marker peptides is selected from the group comprising the following combinations of cardiovascular peptides: ANP and AVP, ANP and ADM, ANP and ET-1, ANP and Calcitonin, ANP and hGH, ADM and ET-1, ADM and Calcitonin, ADM and hGH, ET-1 and Calcitonin, ET-1 and hGH, and Calcitonin and hGH. However, additionally to the set of two cardiovascular peptides, the level of a third or further marker peptides may be determined in some embodiments of the invention.

In one preferred embodiment the level of ANP and ADM is determined. Preferably, the level of MR-proANP and MR-proADM is determined.

In another preferred embodiment the level of ANP and ET-1 is determined. Preferably, the level of MR-proANP and CT-proET-1 is determined.

In another preferred embodiment the level of ANP and Calcitonin is determined. Preferably, the level of MR-proANP and PCT is determined.

In another preferred embodiment the level of ANP and hGH is determined. Preferably, the level of MR-proANP and hGH is determined.

In another preferred embodiment the level of ANP and BNP is determined. Preferably, the level of MR-proANP and NT-proBNP is determined.

In another preferred embodiment the level of ADM and ET-1 is determined. Preferably, the level of MR-proADM and CT-proET-1 is determined.

In another preferred embodiment the level of ADM and Calcitonin is determined. Preferably, the level of MR-proADM and PCT is determined.

In another preferred embodiment the level of ADM and hGH is determined. Preferably, the level of MR-proADM and hGH is determined.

In another preferred embodiment the level of ADM and BNP is determined. Preferably, the level of MR-proADM and NT-proBNP is determined.

In another preferred embodiment the level of ET-1 and Calcitonin is determined. Preferably, the level of CT-proET-1 and PCT is determined.

In another preferred embodiment the level of ET-1 and hGH is determined. Preferably, the level of CT-proET-1 and hGH is determined.

In another preferred embodiment the level of ET-1 and BNP is determined. Preferably, the level of CT-proET-1 and NT-proBNP is determined.

In another preferred embodiment the level of PCT and hGH is determined. Preferably, the level of PCT and hGH is determined.

In another preferred embodiment the level of PCT and BNP is determined. Preferably, the level of PCT and NT-proBNP is determined.

In another preferred embodiment the level of hGH and BNP is determined. Preferably, the level of hGH and NT-proBNP is determined.

In one particular embodiment, the level of at least one marker peptide is determined on the first day of hospitalization (day 0) and on day 1, day 2, day 3, day 4, day 5, day 6, day 7, day 8, day 9 or day 10 after hospitalization. Preferably, the level of at least one marker peptide is determined on day 0, on day 1, on day 3 and on day 5 after hospitalization. More preferably, the level of at least one marker peptide is determined on day 0 and on day 5 after hospitalization. In another preferred embodiment, the level of at least one marker peptide is determined pre-interventional and post-interventionally. More preferably, the level of at least one marker peptide is determined pre-interventional and on day 5. Whenever the level of one or more marker peptides is determined, a sample is taken from the patient.

In a particular embodiment of the invention a sample from said patient is taken on day 0, 1, 2, 3, 4, 5, 6, 7, 8, 9 and/or 10 and the level of at least one marker peptide in said sample is measured and used for the prognosis of an outcome or assessing the risk for said patient or for the determination whether said patient is suffering from stroke or a transient ischemic attack.

It is particularly preferred in the context of the present invention that the presence or amount of a marker selected from the group consisting of NOGO receptor, RNA binding protein regulatory subunit, ubiquitin fusion degradation protein 1 homolog, β-chimerin, nucleoside diphosphate kinaseA, and nitrotyrosine, or one or more markers related thereto is not determined in the sample. The term "related marker" in this context refers to one or more fragments of a particular marker that may be detected as a surrogate for the marker itself. These related markers may be, for example, "pre," "pro," or "prepro" forms of markers, or the "pre," "pro," or "prepro" fragment removed to form the mature marker.

According to a preferred embodiment, the determination is performed using a multivariate analysis considering in addition one or more covariates selected from a group comprising NIHSS, Barthel Index and mRS.

The term "outcome" herein relates for instance to the survival of the patient after a defined time, e.g. after 5 days, 4 weeks, 3 months, 1 year or re-stroke or to a functional outcome. Most preferably the outcome 3 months after the stroke or TIA is predicted.

The term "functional outcome" in the context of the present invention relates to the degree of severity of the disease, i.e. the state of health the patient after a defined time, e.g. after 5 days, 4 weeks, 3 months, or 1 year, preferably with regard to the stroke or stroke-like symptoms. Most preferably the functional outcome 3 months after the stroke or TIA is predicted.

It is preferred in the context of the present invention, that the functional outcome is determined as ranking or the degree of severity of the outcome. The functional outcome may also be expressed in terms of need of nursing care or with respect to activities of daily living (ADL), e.g. according to the Barthel Index, NIHSS and modified Rankin Scale.

Furthermore the present invention also relates to a kit for prognosis of an outcome or assessing the risk of a patient having suffered a stroke or a transient ischemic attack, the kit comprising one or more capture probes (preferably antibodies or functional fragments thereof) directed against marker peptides or fragments thereof or precursors or fragments thereof selected from the group comprising ANP, AVP, ADM, ET-1, calcitonin, troponin, CRP and hGH. The kit may optionally comprise a capture probe (preferably an antibody or functional fragment thereof) directed against BNP. The kit may additionally comprise reagents necessary for detection, such as buffers. In addition the kit may also comprise one or more standard samples, i.e. one or more samples of defined concentration of one or more of the marker peptides.

Preferably, the kit comprises a combination of at least two capture probes directed marker peptides or fragments thereof or precursors or fragments thereof, the combinations being selected from the group comprising MR-proANP and MR-proADM, MR-proANP and CT-proET-1, MR-proADM and CT-proET-1, MR-proANP and hGH, hGH and MR-proADM, hGH and CT-proET-1, MR-proANP and PCT, MR-proADM and PCT, CT-proAVP and PCT, CT-proET-1 and PCT, hGH and PCT.

The present invention also relates to the use of the methods of the invention or the kits of the invention for prognosis of an outcome or assessing the risk of a patient having suffered a stroke or a transient ischemic attack.

The invention also relates to the use of the methods of the invention for monitoring of the therapy in a patient having suffered a stroke or a transient ischemic attack.

The invention also relates to the use of the methods of the invention for differentially diagnosing ischemic stroke, hemorrhagic stroke and/or transient ischemic attack in said subject, preferably within 24 hours after the first symptoms of stroke or TIA. It is particularly preferred that the methods or the kits are used for differentiating ischemic stroke from hemorrhagic stroke or for differentiating ischemic and/or hemorrhagic stroke from transient ischemic attack. Preferred single markers in this context are ANP, particularly MR-proANP, AVP, particularly copeptin, ADM, particularly MR-proADM, ET-1, particularly CT-proET-1, PCT and hGH. Also combinations of two or more of the marker peptides of the present invention may be used in this context. Particularly preferred combinations comprise MR-proANP and MR-proADM, MR-proANP and CT-proET-1, MR-proADM and CT-proET-1, MR-proANP and hGH, hGH and MR-proADM, hGH and CT-proET-1, MR-proANP and PCT, MR-proADM and PCT, CT-proAVP and PCT, CT-proET-1 and PCT, hGH and PCT.

Determining (or measuring or detecting) the level of a marker peptide herein is performed using a detection method and/or a diagnostic assay as explained below.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ M$^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (*The Immunoassay Handbook*, Ed. David Wild, Elsevier LTD, Oxford; 3rd ed. (May 2005), ISBN-13: 978-0080445267; Hultschig C et al., *Curr Opin Chem Biol*. 2006 February; 10(1):4-10. PMID: 16376134), incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, auch as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The levels, i.e. the concentrations, of the one or more marker peptides (or fragments thereof or precursors or fragments thereof) in the sample of the patient are attributed to the prognosis of an outcome or assessing the risk for the patient. For instance, concentrations of the marker peptide above a certain threshold value are indicative for an adverse outcome or an elevated risk for the patient. Such threshold values are preferably in the range of from about 100 to 300 pmol/l, more preferably 250 pmol/l, most preferably 188 pmol/l for MR-proANP; in the range of from about 10 to 40 pmol/l, more preferably 15 pmol/l, most preferably 20.3 pmol/l for Copeptin; in the range of from about 0.4 to 1.0 nmol/l, more preferably 0.5 nmol/l, most preferably 0.67 nmol/l for MR-proADM; in the range of from about 50 to 120 pmol/l, more preferably 75 pmol/l, most preferably 98.3 pmol/l for CT-pro-ET-1; in the range of from about 0.01 to 0.06 ng/ml, more preferably 0.015 ng/ml, most preferably 0.026 ng/ml for PCT; in the range of from about 0.25 to 1.0 ng/ml, more preferably 0.5 ng/ml, most preferably 0.34 ng/ml for hGH; in the range of from about 250 to 500 pg/ml, more preferably 450 pg/ml, most preferably 370 pg/ml for NT-proBNP.

Preferably herein a sensitive PCT assay (e.g. the PCT sensitive assay, B.R.A.H.M.S AG, Hennigsdorf, Germany) is used. Preferably herein, the PCT assay has a functional sensitivity of 0.05 ng/ml or below.

This means that in one embodiment of the methods of the invention, PCT levels are measured with high sensitivity (i.e. a sensitivity of 0.05 ng/ml, preferably 0.02 ng/ml), in the sample of the patient. Preferably in this context, the level of PCT is correlated with the survival prognosis of a patient.

In another embodiment of the invention, the risk and/or outcome for a patient is determined by relating the patient's individual level of marker peptide to certain percentiles (e.g. 97.5$^{th}$ percentile) of a healthy population.

Preferred threshold values for the differential diagnosis of stroke (hemorrhagic and/or ischemic) from TIA are in the range of from about 90 to about 140 pmol/l for MR-proANP, in the range of from about 9.5 to about 11.5 pmol/l for Copeptin, in the range of from about 0.5 to about 0.8 nmol/l for MR-proADM, in the range of from about 65 to about 90 pmol/l for CT-pro-ET-1, in the range of from about 0.0230 to about 0.0260 ng/ml for PCT, and in the range of from about 0.10 to about 0.3 ng/ml for hGH, wherein a value below the threshold is indicative for TIA and above the threshold indicative for stroke. Exemplary thresholds for the differential diagnosis are also given in table 25 of example 11.

Survival analysis (Cox regression and hazard ratios) and Kaplan-Meier estimators may be used for the assessment or prediction of the outcome or risk (e.g. morbidity) of a patient with a peptide level e.g. above or below a cut off. The mortality, e.g. 3, 4 or 12 months after the stroke or TIA can be assessed by hazard ratios, describing the increase of risk for patients with peptide levels above a certain cut-off value. The increase of risk of a re-stroke or re-TIA, respectively, occurring within the observation period after the stroke or TIA can for instance be determined by odds ratios and cross tables.

From the comparison of the respective levels of one or more of the marker peptides at the day of hospitalization and at a certain time after hospitalization, e.g. on day 5 after hospitalization, the outcome/risk, e.g. the survival probability after 3, 4, 12 months may be predicted using Kaplan- Meier estimators and hazard ratios for patients with a peptide level e.g. above or below a cut off.

In general, the determined values of the levels of more than one marker peptide may be used for the assessment of the outcome and the risk for the patient by counting the number of peptide levels that have values above the respective cut off. The more peptide levels are above the cut off, the higher the risk for the patient. Kaplan-Meier estimators can be used to predict mortality, odds ratios can be applied to describe the risk increase for prediction of re-stroke or re-TIA.

As mentioned herein above, the determined levels of the marker peptides may according to the present invention be expressed in terms of functional outcome, e.g. expressed as according to the Barthel Index, NIHSS or modified Rankin Scale. E.g., using box plots (peptide levels by outcome), receiver operating characteristics (ROC) analysis and odds ratios, peptide levels can be used to predict the future functional outcome.

The methods and kits according to the invention may also be used for determining whether said patient is suffering from stroke or a transient ischemic attack based on the level of said at least one cardiovascular peptide. In this context, the sample is preferably taken pre-interventionally.

Sequences

The amino acid sequence of the precursor peptide of Adrenomedulin (pre-pro-Adrenomedullin) is given in SEQ ID NO: 1. Pro-Adrenomedullin relates to amino acid residues 22 to 185 of the sequence of pre-pro-Adrenomedullin. The amino acid sequence of pro-Adrenomedullin (pro-ADM) is given in SEQ ID NO:2. The pro-ADM N-terminal 20 peptide (PAMP) relates to amino acid residues 22-41 of pre-proADM. The amino acid sequence of PAMP is given in SEQ ID NO:3. MR-pro-Adrenomedullin (MR-pro-ADM) relates to amino acid residues 45-92 of pre-pro-ADM. The amino acid sequence of MR-pro-ADM is provided in SEQ ID NO:4. The amino acid sequence of mature Adrenomedullin (ADM) is given in SEQ ID NO:5.

The amino acid sequence of ANP is given in SEQ ID NO:8. The sequence of the 153 amino acid pre-pro-ANP is shown in SEQ ID NO:6. Upon cleavage of an N-terminal signal peptide (25 amino acids) and the two C-terminal amino acids (127/128) proANP (SEQ ID NO:7) is released. ANP comprises residues 99-126 from the C-terminus of the precursor prohormone pro-ANP. This prohormone is cleaved into the mature 28 amino acid peptide ANP, also known as ANP (1-28) or α-ANP, and the amino terminal fragment ANP (1-98) (NT-proANP, SEQ ID NO:9). Midregional proANP (MR-proANP) is defined as NT-proANP or any fragments thereof comprising at least amino acid residues 53-90 (SEQ ID NO:10) of proANP. The C-terminal two arginine residues (positions 152 and 153 in pre-pro-ANP, SEQ ID NO:6, are not present in another allele of the gene encoding pre-pro-ANP, thus pre-pro-ANP may comprise only residues 1 to 151. This of course is also true for the respective fragments of pre-pro-ANP, particularly pro-ANP and copeptin may or may not comprise these two C-terminal arginines.

The sequence of the 164 amino acid precursor peptide of Vasopressin (pre-pro-Vasopressin) is given in SEQ ID NO:11. Pro-Vasopressin relates to the amino acid residues 29 to 164 of the sequence of pre-pro-Vasopressin. The amino acid sequence of pro-Vasopressin is given in SEQ ID NO:12. Pro-Vasopressin is cleaved into mature Vasopressin, Neurophysin II and C-terminal proVasopressin (CT-proAVP or Copeptin). Vasopressin relates to the amino acid residues 20 to 28 of pre-pro-Vasopressin. The amino acid sequence of Vasopressin is shown in SEQ ID NO:13. Coeptin relates to amino acid residues 126 to 164 of pre-pro-Vasopressin. The amino acid sequence of Copeptin is provided in SEQ ID NO:14. Neurophysin II comprises the amino acid residues 32 to 124 of pre-pro-Vasopressin and its sequence is shown in SEQ ID NO:15.

The sequence of the 212 amino acid precursor peptide of Endothelin-1 (pre-pro-Endothelin-1) is given in SEQ ID NO:16. Pro-ET-1 relates to the amino acid residues 18 to 212 of the sequence of pre-pro-ET-1. The amino acid sequence of pro-ET-1 is given in SEQ ID NO:17. Pro-ET-1 is cleaved into mature ET-1, big-ET-1 and C-terminal proET-1 (CT-proET-1). ET-1 relates to the amino acid residues 53 to 73 of pre-pro-ET-1. The amino acid sequence of ET-1 is shown in SEQ ID NO:18. CT-proET-1 relates to amino acid residues 168 to 212 of pre-pro-ET-1. The amino acid sequence of CT-proET-1 is provided in SEQ ID NO:19. Big-ET-1 comprises the amino acid residues 53 to 90 of pre-pro-ET-1 and its sequence is shown in SEQ ID NO:20.

The sequence of the 141 amino acid precursor peptide of calcitonin (pre-pro-Calcitonin) is given in SEQ ID NO:21. Procalcitonin (PCT) relates to the amino acid residues 26 to 141 of the pre-pro-Calcitonin sequence. The amino acid sequence of PCT is shown in SEQ ID NO:22. Procalcitonin is cleaved into N-terminal PCT, Calcitonin and Katacalcin. N-terminal PCT comprises the amino acids 26 to 82 and its sequence is shown in SEQ ID NO:23. Calcitonin relates to amino acid residues 85 to 116 and its sequence is given in SEQ ID NO:24. The sequence of Katacalcin, comprising amino acid residues 121-141, is provided in SEQ ID NO:25.

The sequence of the 134 amino acid precursor peptide of brain natriuretic peptide (pre-pro-BNP) is given in SEQ ID NO:26. Pro-BNP relates to amino acid residues 27 to 134 of pro-pro-BNP. The sequence of pro-BNP is shown in SEQ ID NO:27. Pro-BNP is cleaved into N-terminal pro-BNP (NT-pro-BNP) and mature BNP. NT-pro-BNP comprises the amino acid residues 27 to 102 and its sequence is shown in SEQ ID NO:28. The SEQ ID NO:29 shows the sequence of BNP comprising the amino acid residues 103 to 134 of the pre-pro-BNP peptide.

```
                                              SEQ ID NO: 1
(amino acid sequence of pre-pro-ADM):
   1   MKLVSVALMY LGSLAFLGAD TARLDVASEF RKKWNKWALS
       RGKRELRMSS

51   SYPTGLADVK AGPAQTLIRP QDMKGASRSP EDSSPDAARI
       RVKRYRQSMN

101   NFQGLRSFGC RFGTCTVQKL AHQIYQFTDK DKDNVAPRSK
       ISPQGYGRRR

151   RRSLPEAGPG RTLVSSKPQA HGAPAPPSGS APHFL

SEQ ID NO: 2
(amino acid sequence of pro-ADM):
   1   ARLDVASEFR KKWNKWALSR GKRELRMSSS YPTGLADVKA
       GPAQTLIRPQ

51   DMKGASRSPE DSSPDAARIR VKRYRQSMNN FQGLRSFGCR
       FGTCTVQKLA

101   HQIYQFTDKD KDNVAPRSKI SPQGYGRRRR RSLPEAGPGR
       TLVSSKPQAH

151   GAPAPPSGSA PHFL

SEQ ID NO: 3
(amino acid sequence of pro-ADM N20):
   1   ARLDVASEFR KKWNKWALSR
```

-continued

SEQ ID NO: 4
(amino acid sequence of MR-pro-ADM):
1    ELRMSSSYPT GLADVKAGPA QTLIRPQDMK GASRSPEDSS
     PDAARIRV SEQ ID NO: 5
(amino acid sequence of ADM):
1    YRQSMNNFQG LRSFGCRFGT CTVQKLAHQI YQFTDKDKDN
     VAPRSKISPQ
51   GY SEQ ID NO: 6
(amino acid sequence of pre-pro-ANP):
1    MSSFSTTTVS FLLLLAFQLL GQTRANPMYN AVSNADLMDF
     KNLLDHLEEK
51   MPLEDEVVPP QVLSEPNEEA GAALSPLPEV PPWTGEVSPA
     QRDGGALGRG
101  PWDSSDRSAL LKSKLRALLT APRSLRRSSC FGGRMDRIGA
     QSGLGCNSFR
151  YRR SEQ ID NO: 7
(amino acid sequence of pro-ANP):
1    NPMYNAVSNA DLMDFKNLLD HLEEKMPLED EVVPPQVLSE
     PNEEAGAALS
51   PLPEVPPWTG EVSPAQRDGG ALGRGPWDSS DRSALLKSKL
     RALLTAPRSL
101  RRSSCFGGRM DRIGAQSGLG CNSFRY SEQ ID NO: 8
(amino acid sequence of ANP):
1    SLRRSSCFGG RMDRIGAQSG LGCNSFRY SEQ ID NO: 9
(amino acid sequence of NT-proANP):
1    NPMYNAVSNA DLMDFKNLLD HLEEKMPLED EVVPPQVLSE
     PNEEAGAALS
51   PLPEVPPWTG EVSPAQRDGG ALGRGPWDSS DRSALLKSKL
     RALLTAPR SEQ ID NO: 10
(amino acid sequence of amino acids 53-90 of proANP):
1    PEVPPWTGEV SPAQRDGGAL GRGPWDSSDR SALLKSKL SEQ ID NO: 11
(amino acid sequence of pre-pro-AVP):
1    MPDTMLPACF LGLLAFSSAC YFQNCPRGGK RAMSDLELRQ
     CLPCGPGGKG
51   RCFGPSICCA DELGCFVGTA EALRCQEENY LPSPCQSGQK
     ACGSGGRCAA
101  FGVCCNDESC VTEPECREGF HRRARASDRS NATQLDGPAG
     ALLLRLVQLA
151  GAPEPFEPAQ PDAY SEQ ID NO: 12
(amino acid sequence of pro-AVP):
1    CYFQNCPRGG KRAMSDLELR QCLPCGPGGK GRCFGPSICC
     ADELGCFVGT
51   AEALRCQEEN YLPSPCQSGQ KACGSGGRCA AFGVCCNDES
     CVTEPECREG
101  FHRRARASDR SNATQLDGPA GALLLRLVQL AGAPEPFEPA
     QPDAY SEQ ID NO: 13
(amino acid sequence of AVP):
1    CYFQNCPRG SEQ ID NO: 14
(amino acid sequence of CT-pre-proAVP or Copeptin):
1    ASDRSNATQL DGPAGALLLR LVQLAGAPEP FEPAQPDAY SEQ ID NO: 15
(amino acid sequence of Neurophysin II):
1    AMSDLELRQC LPCGPGGKGR CFGPSICCAD ELGCFVGTAE
     ALRCQEENYL
51   PSPCQSGQKA CGSGGRCAAF GVCCNDESCV TEPECREGFH
     RRA SEQ ID NO: 16
(amino acid sequence of pre-pro-ET-1):
1    MDYLLMIFSL LFVACQGAPE TAVLGAELSA VGENGGEKPT
     PSPPWRLRRS
51   KRCSCSSLMD KECVYFCHLD IIWVNTPEHV VPYGLGSPRS
     KRALENLLPT
101  KATDRENRCQ CASQKDKKCW NFCQAGKELR AEDIMEKDWN
     NHKKGKDCSK
151  LGKKCIYQQL VRGRKIRRSS EEHLRQTRSE TMRNSVKSSF
     HDPKLKGKPS
201  RERYVTHNRA HW SEQ ID NO: 17
(amino acid sequence of pro-ET-1):
1    APETAVLGAE LSAVGENGGE KPTPSPPWRL RRSKRCSCSS
     LMDKECVYFC
51   HLDIIWVNTP EHVVPYGLGS PRSKRALENL LPTKATDREN
     RCQCASQKDK
101  KCWNFCQAGK ELRAEDIMEK DWNNHKKGKD CSKLGKKCIY
     QQLVRGRKIR
151  RSSEEHLRQT RSETMRNSVK SSFHDPKLKG KPSRERYVTH
     NRAHW SEQ ID NO: 18
(amino acid sequence of ET-1):
1    CSCSSLMDKE CVYFCHLDII W SEQ ID NO: 19
(amino acid sequence of CT-pro-ET-1):
1    RSSEEHLRQT RSETMRNSVK SSFHDPKLKG KPSRERYVTH
     NRAHW SEQ ID NO: 20
(amino acid sequence of Big-ET-1):
1    CSCSSLMDKE CVYFCHLDII WVNTPEHVVP YGLGSPRS SEQ ID NO: 21
(amino acid sequence of pre-pro-Calcitonin):
1    MGFQKFSPFL ALSILVLLQA GSLHAAPFRS ALESSPADPA
     TLSEDEARLL
51   LAALVQDYVQ MKASELEQEQ EREGSSLDSP RSKRCGNLST
     CMLGTYTQDF
101  NKFHTFPQTA IGVGAPGKKR DMSSDLERDH RPHVSMPQNA
     N SEQ ID NO: 22
(amino acid sequence of PCT):
1    APFRSALESS PADPATLSED EARLLLAALV QDYVQMKASE
     LEQEQEREGS
51   SLDSPRSKRC GNLSTCMLGT YTQDFNKFHT FPQTAIGVGA
     PGKKRDMSSD
101  LERDHRPHVS MPQNAN -continued SEQ ID NO: 23
(amino acid sequence of N-terminal PCT):
  1   APFRSALESS PADPATLSED EARLLLAALV QDYVQMKASE
      LEQEQEREGS
 51   SLDSPRS SEQ ID NO: 24
(amino acid sequence of Calcitonin):
  1   CGNLSTCMLG TYTQDFNKFH TFPQTAIGVG AP SEQ ID NO: 25
(amino acid sequence of Katacalcin):
  1   DMSSDLERDH RPHVSMPQNA N SEQ ID NO: 26
(amino acid sequence of pre-pro-BNP):
  1   MDPQTAPSRA LLLLLFLHLA FLGGRSHPLG SPGSASDLET
      SGLQEQRNHL
 51   QGKLSELQVE QTSLEPLQES PRPTGVWKSR EVATEGIRGH
      RKMVLYTLRA
101   PRSPKMVQGS GCFGRKMDRI SSSSGLGCKV LRRH SEQ ID NO: 27
(amino acid sequence of pro-BNP):
  1   HPLGSPGSAS DLETSGLQEQ RNHLQGKLSE LQVEQTSLEP
      LQESPRPTGV
 51   WKSREVATEG IRGHRKMVLY TLRAPRSPKM VQGSGCFGRK
      MDRISSSSGL
101   GCKVLRRH SEQ ID NO: 28
(amino acid sequence of NT-pro-BNP):
  1   HPLGSPGSAS DLETSGLQEQ RNHLQGKLSE LQVEQTSLEP
      LQESPRPTGV
 51   WKSREVATEG IRGHRKMVLY TLRAPR SEQ ID NO: 29
(amino acid sequence of BNP):
  1   SPKMVQGSGC FGRKMDRISS SSGLGCKVLR RH

Figure 1:
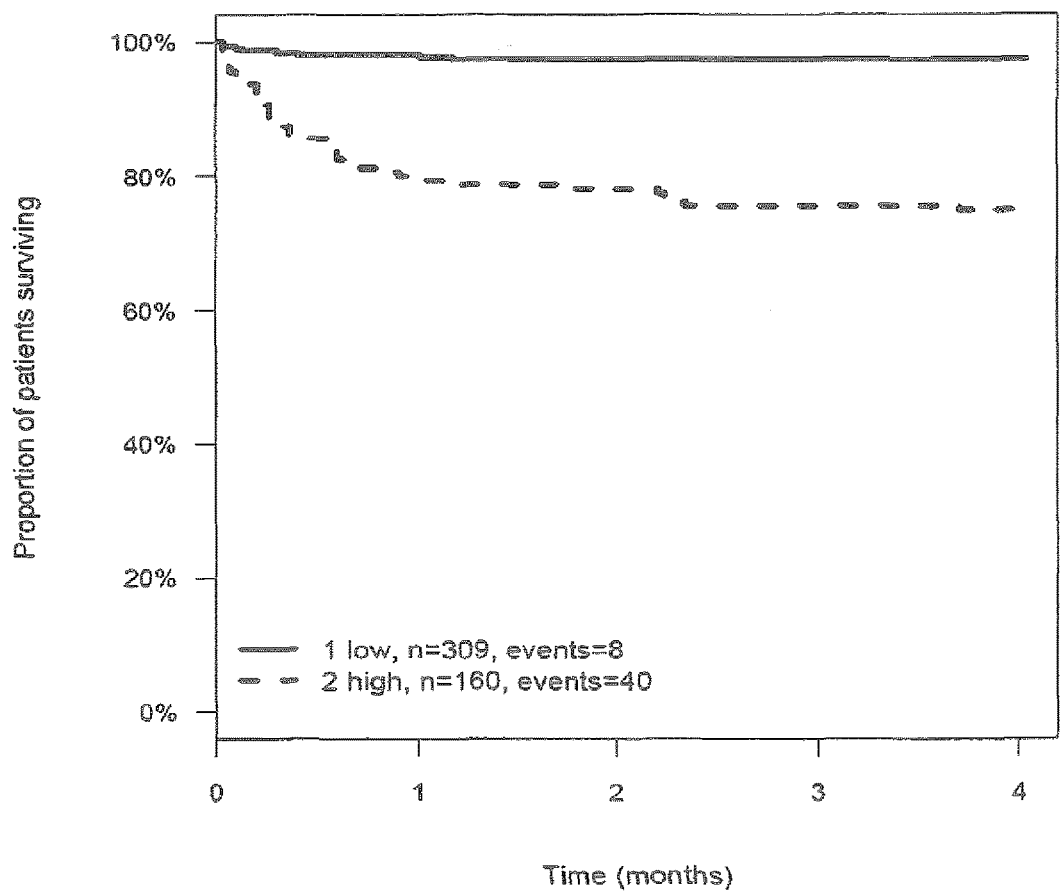
FIG. 1: Kaplan-Meier plot (proportion of patients surviving within four months) for patients with high (dashed lined) and low (solid line) levels of pre-interventionally measured MR-proANP.
Figure 2:
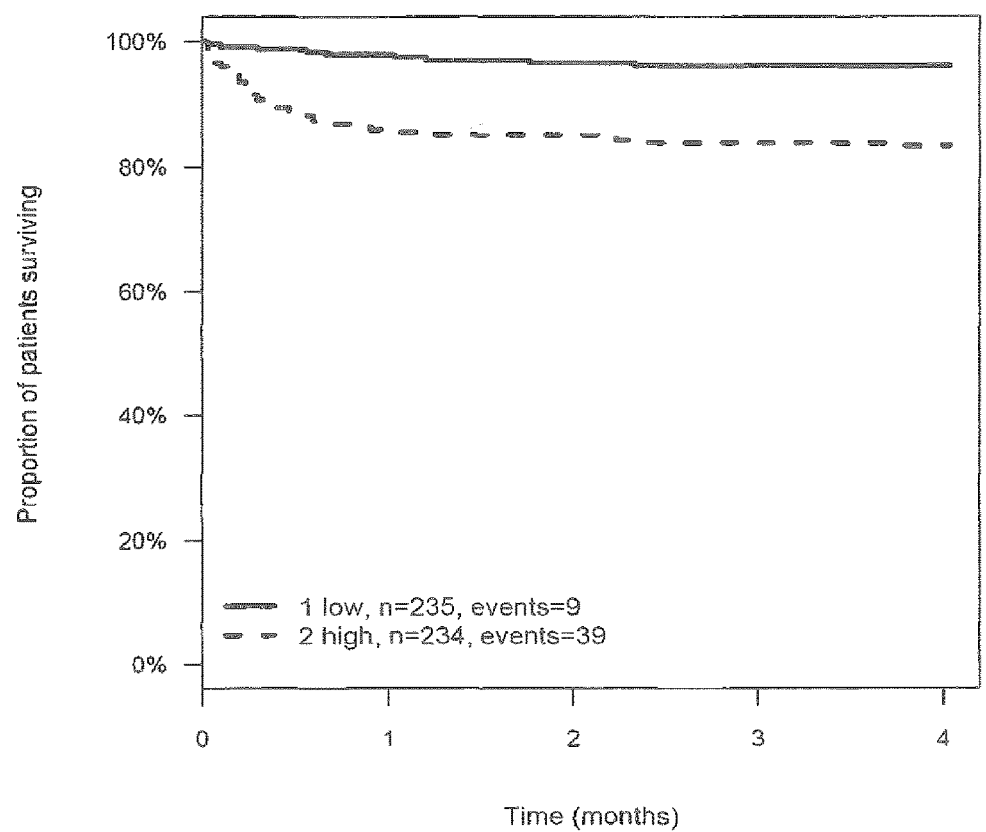
FIG. 2: Kaplan-Meier plot for patients with high (dashed lined) and low (solid line) levels of pre-interventionally measured MR-proADM.
Figure 3:
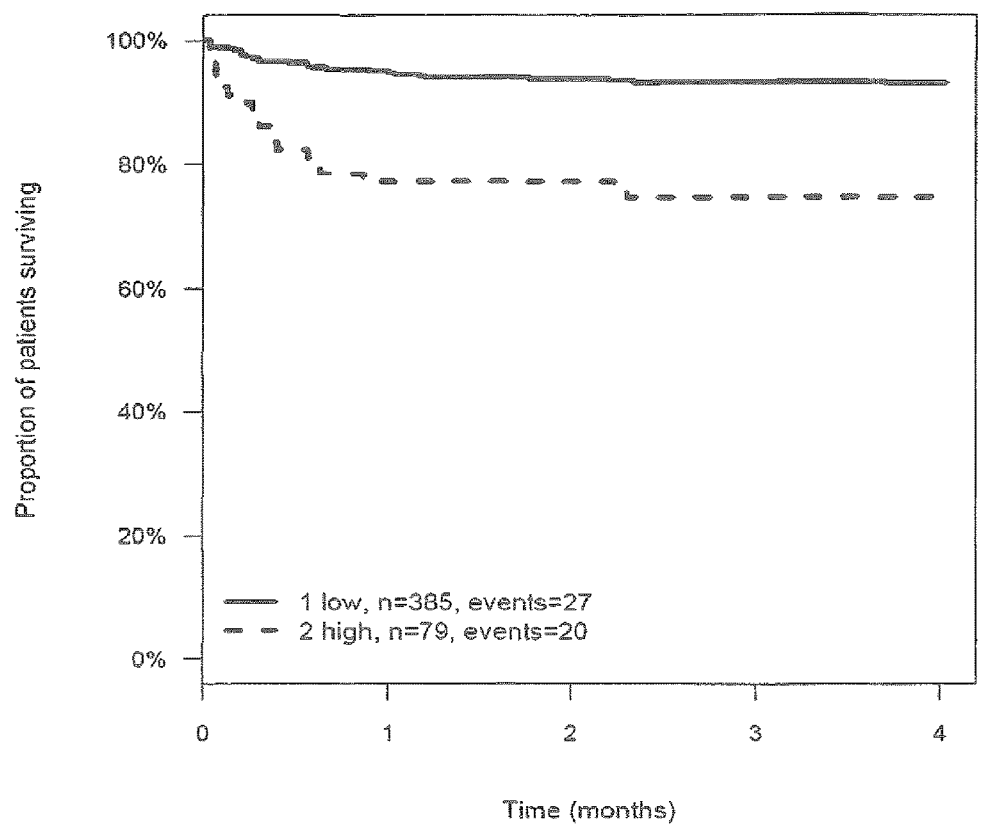
FIG. 3: Kaplan-Meier plot for patients with high (dashed lined) and low (solid line) levels of pre-interventionally measured CT-proET-1.
Figure 4:
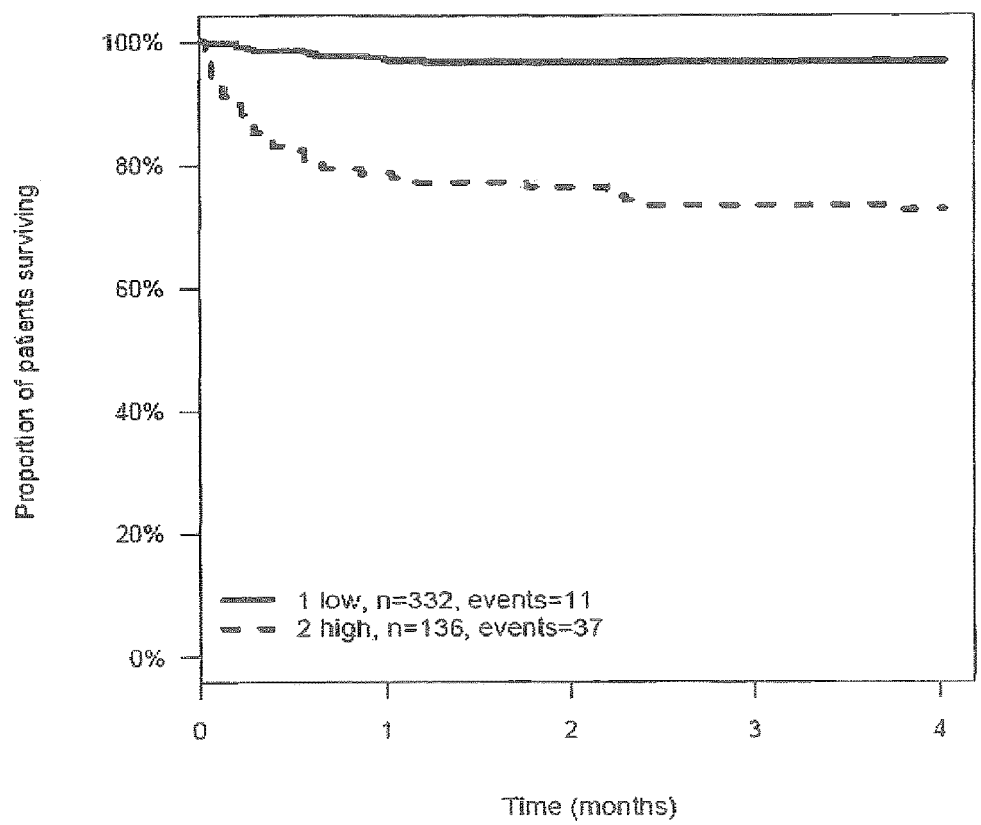
FIG. 4: Kaplan-Meier plot for patients with high (dashed lined) and low (solid line) levels of pre-interventionally measured CT-proAVP.
Figure 5:
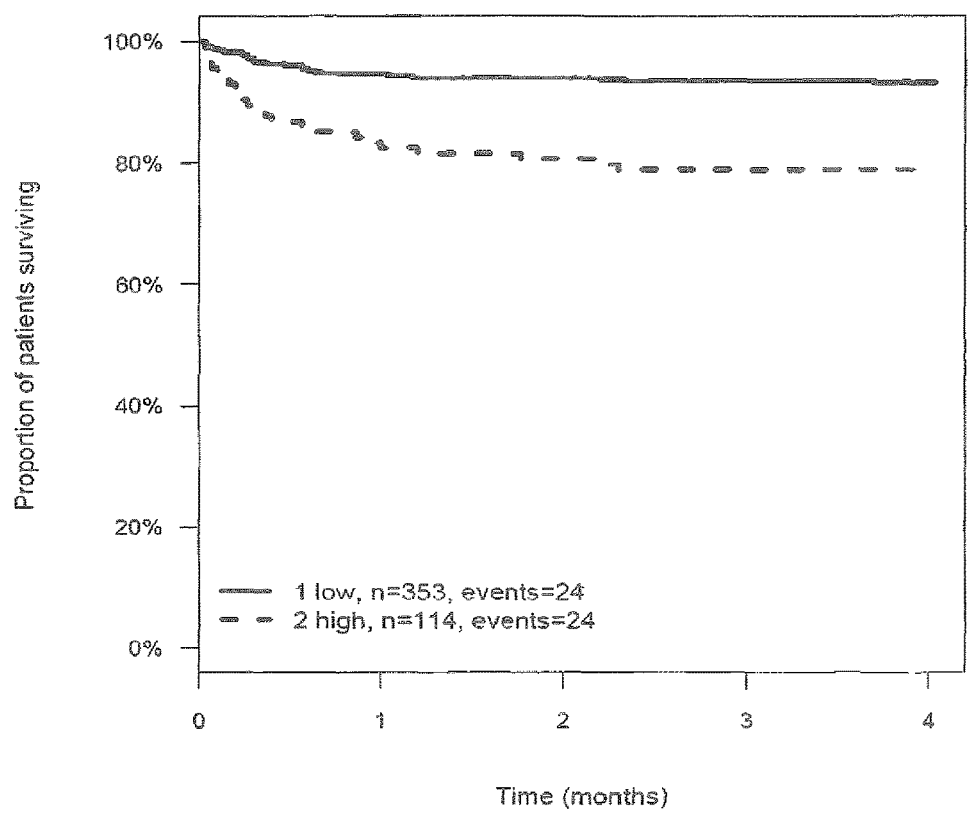
FIG. 5: Kaplan-Meier plot for patients with high (dashed lined) and low (solid line) levels of pre-interventionally measured PCT.
Figure 6:
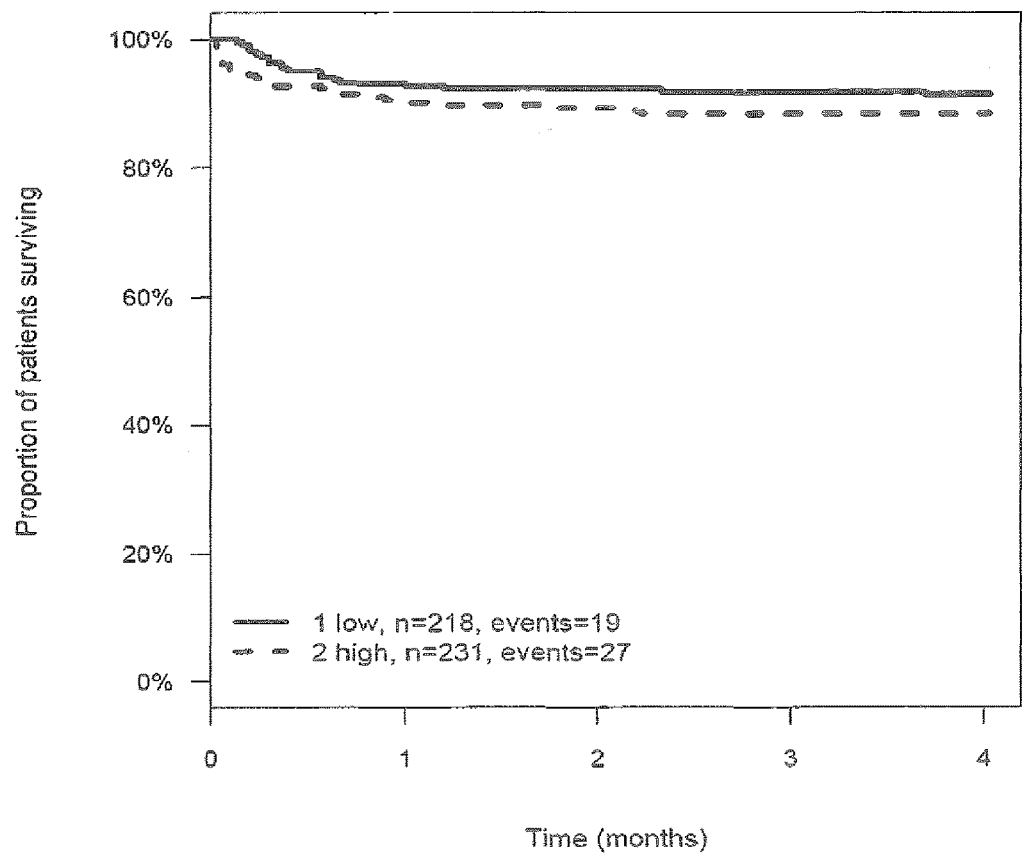
FIG. 6: Kaplan-Meier plot for patients with high (dashed lined) and low (solid line) levels of pre-interventionally measured hGH.
Figure 7:
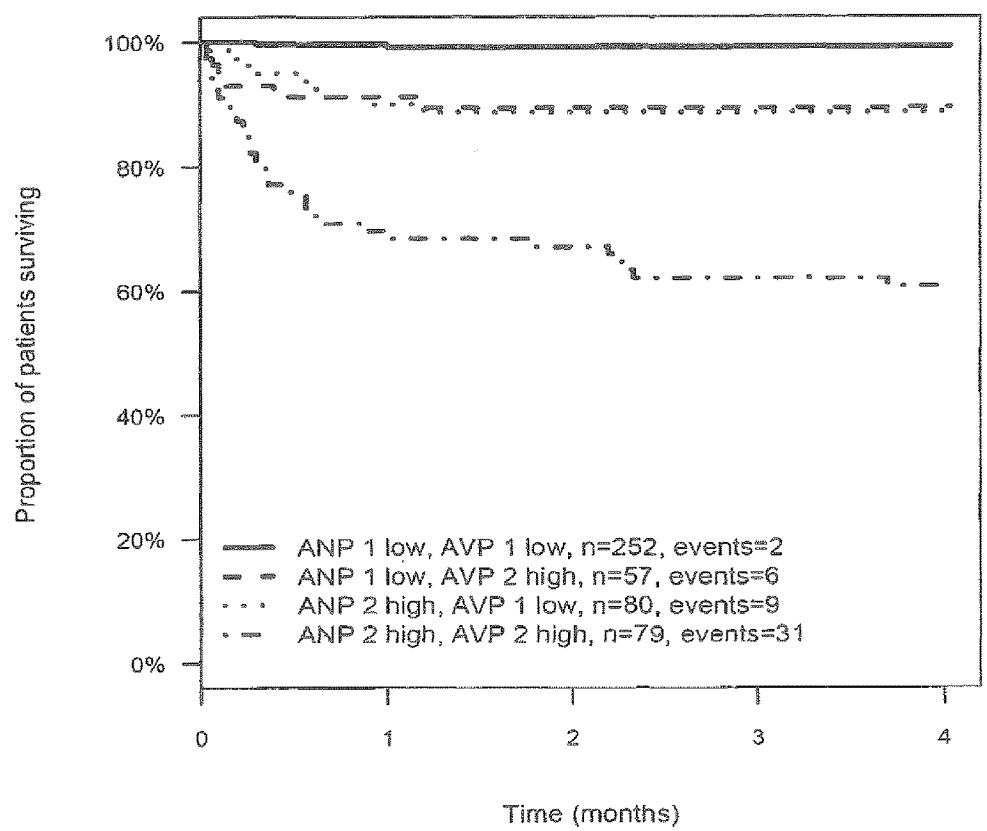
FIG. 7: Kaplan-Meier plot for patients with high and low levels of pre-interventionally measured MR-proANP and CT-proAVP (pairwise combination of both markers). Solid line: both markers low (below defined threshold); dashed/dotted line: both markers high (above defined threshold); dashed line: first marker low, second marker high; dotted line: first marker high, second marker low.
Figure 8:
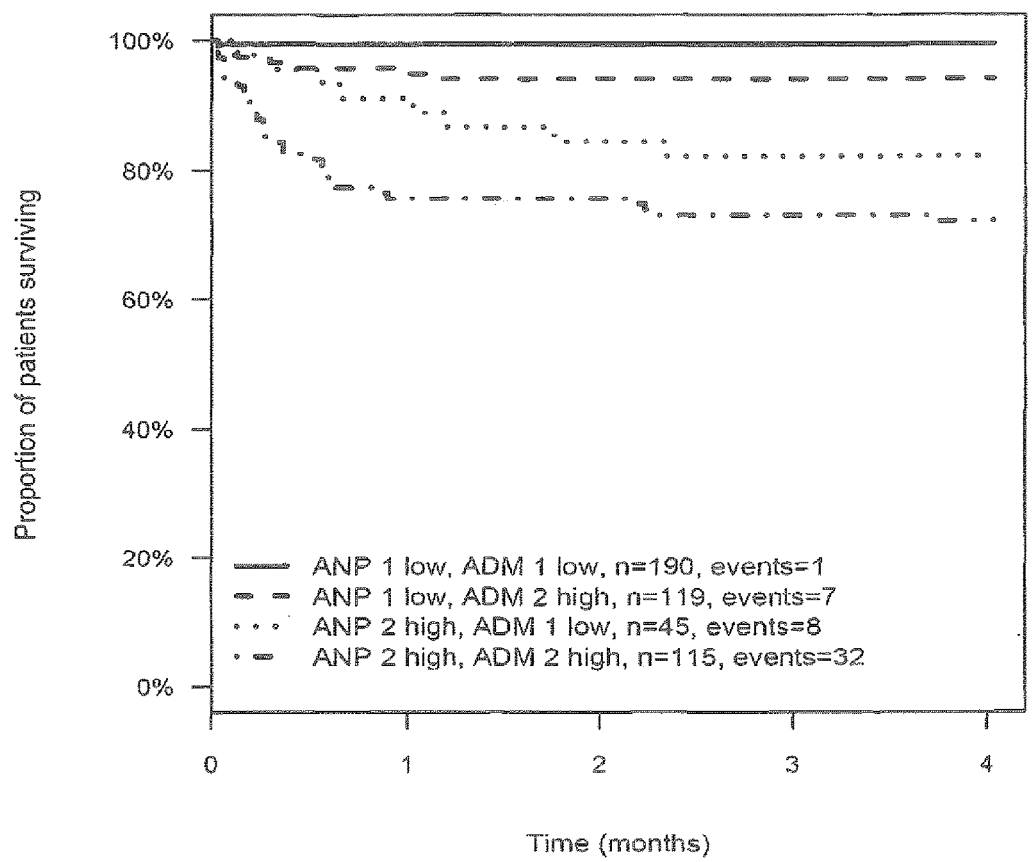
FIG. 8: Kaplan-Meier plot for patients with high and low levels of pre-interventionally measured MR-proANP and MR-proADM (pairwise combination of both markers). Solid line: both markers low (below defined threshold); dashed/dotted line: both markers high (above defined threshold); dashed line: first marker low, second marker high; dotted line: first marker high, second marker low.
Figure 9:
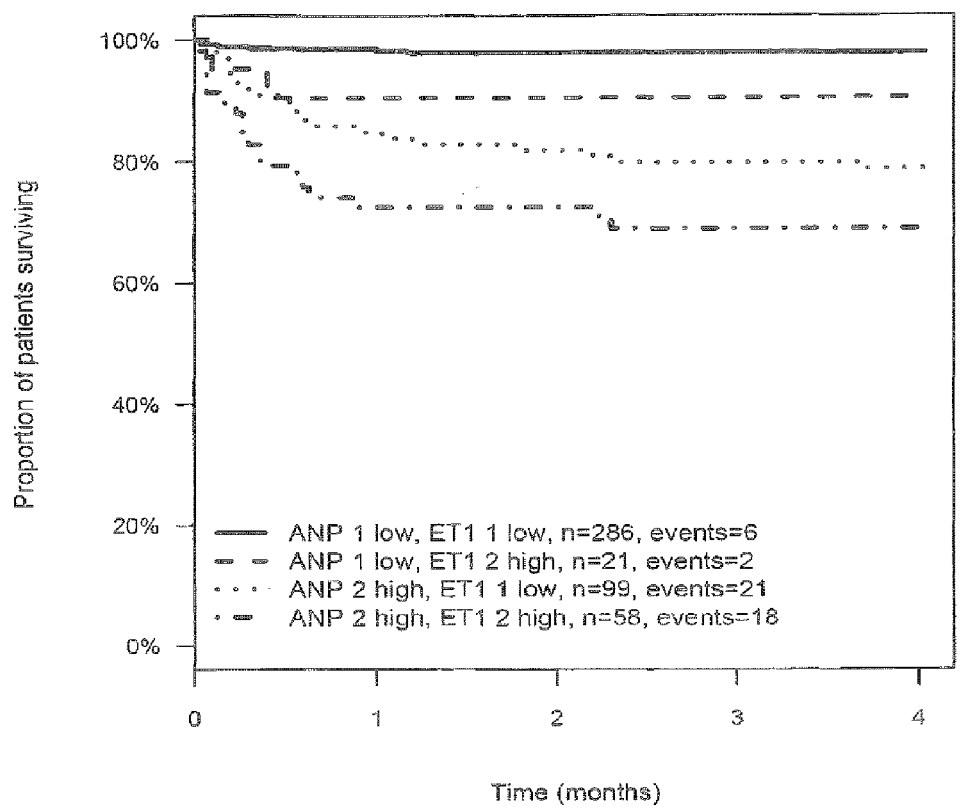
FIG. 9: Kaplan-Meier plot for patients with high and low levels of pre-interventionally measured MR-proANP and CT-proET-1 (pairwise combination of both markers). Solid line: both markers low (below defined threshold); dashed/dotted line: both markers high (above defined threshold); dashed line: first marker low, second marker high; dotted line: first marker high, second marker low.
Figure 10:
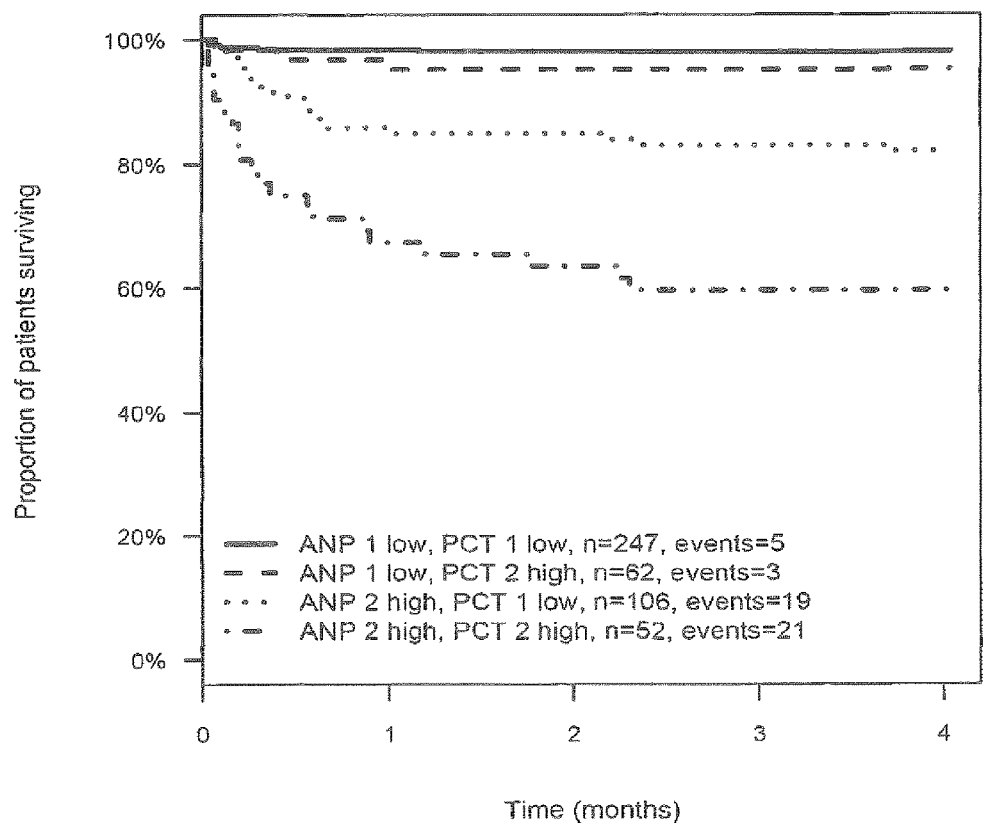
FIG. 10: Kaplan-Meier plot for patients with high and low levels of pre-interventionally measured MR-proANP and PCT (pairwise combination of both markers). Solid line: both markers low (below defined threshold); dashed/dotted line: both markers high (above defined threshold); dashed line: first marker low, second marker high; dotted line: first marker high, second marker low.
Figure 11:
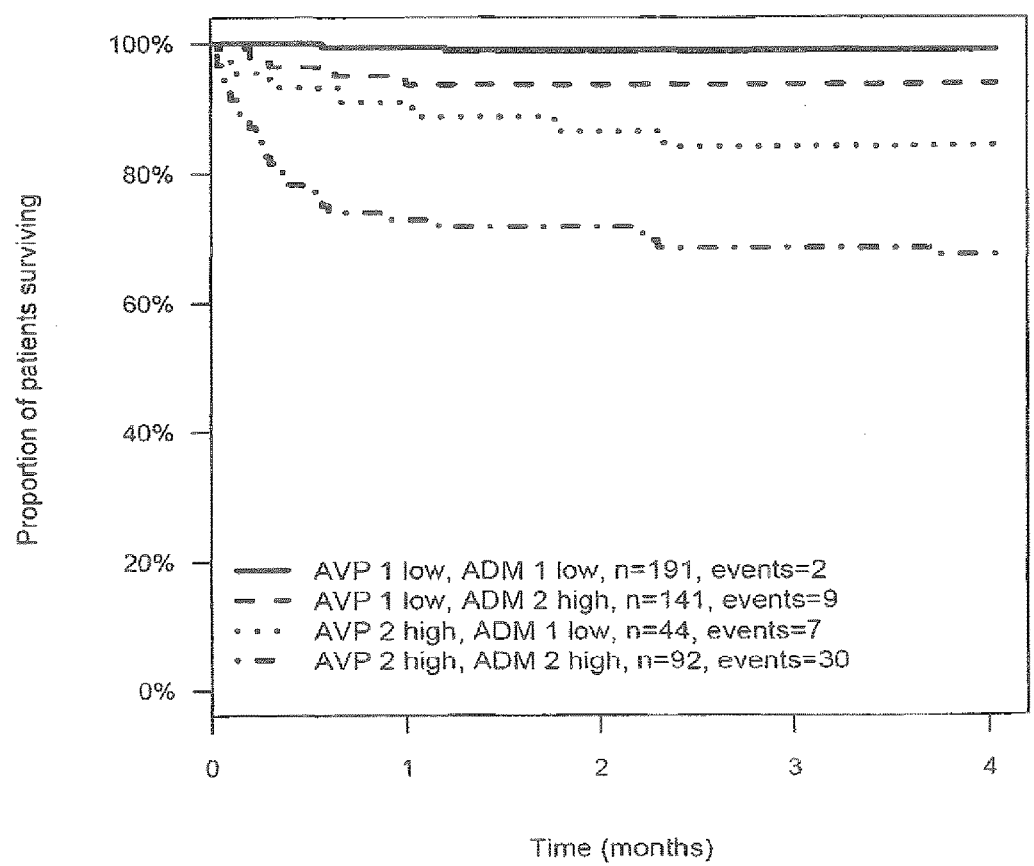
FIG. 11: Kaplan-Meier plot for patients with high and low levels of pre-interventionally measured CT-proAVP and MR-proADM (pairwise combination of both markers). Solid line: both markers low (below defined threshold); dashed/dotted line: both markers high (above defined threshold); dashed line: first marker low, second marker high; dotted line: first marker high, second marker low.
Figure 12:
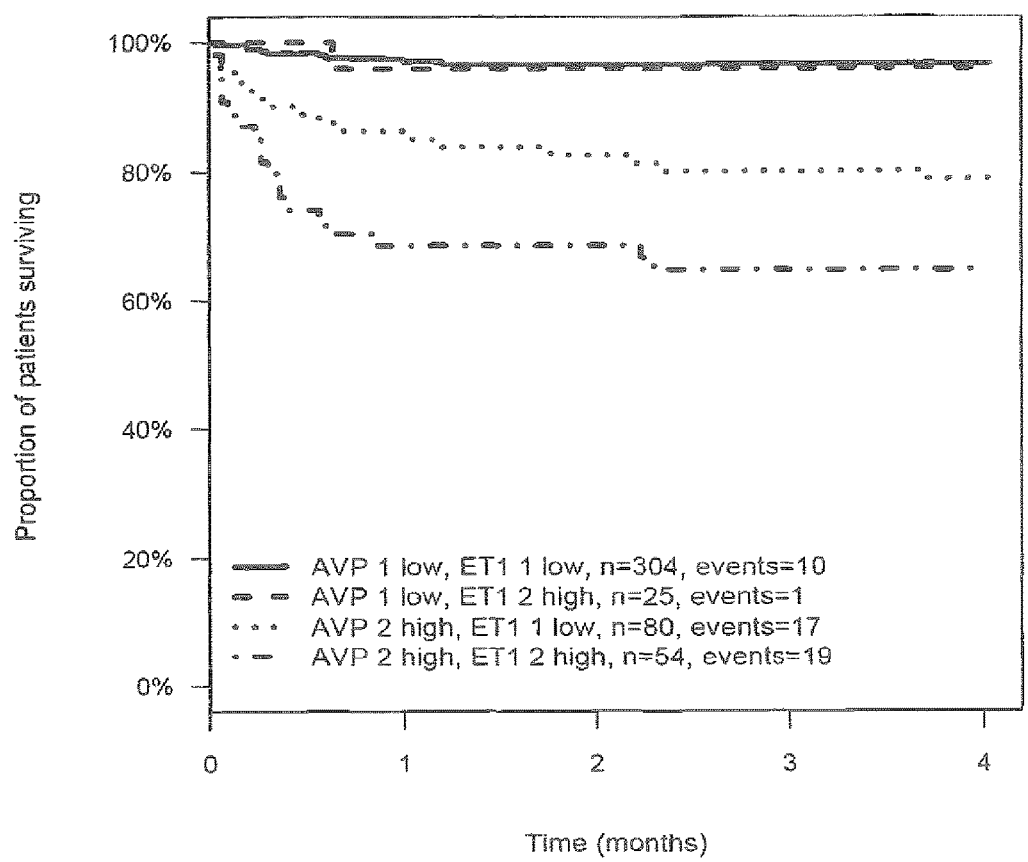
FIG. 12: Kaplan-Meier plot for patients with high and low levels of pre-interventionally measured CT-proAVP and CT-proET-1 (pairwise combination of both markers). Solid line: both markers low (below defined threshold); dashed/dotted line: both markers high (above defined threshold); dashed line: first marker low, second marker high; dotted line: first marker high, second marker low.
Figure 13:
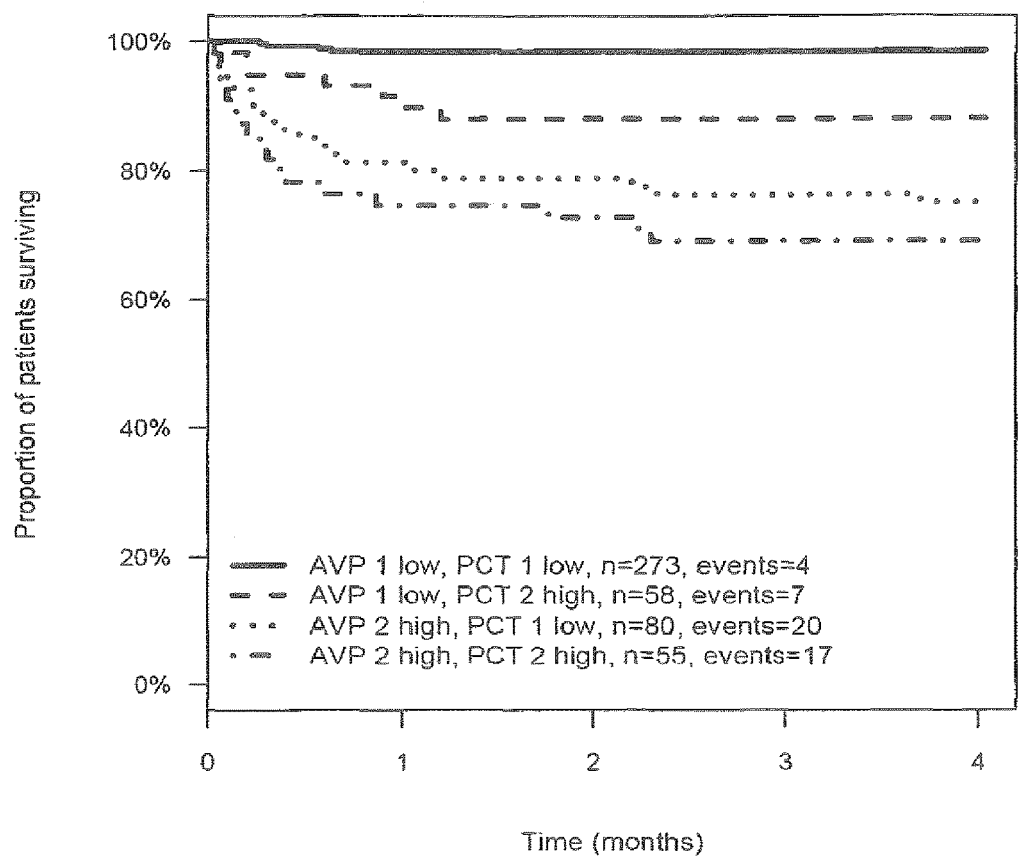
FIG. 13: Kaplan-Meier plot for patients with high and low levels of pre-interventionally measured CT-proAVP and PCT (pairwise combination of both markers). Solid line: both markers low (below defined threshold); dashed/dotted line: both markers high (above defined threshold); dashed line: first marker low, second marker high; dotted line: first marker high, second marker low.
Figure 14:
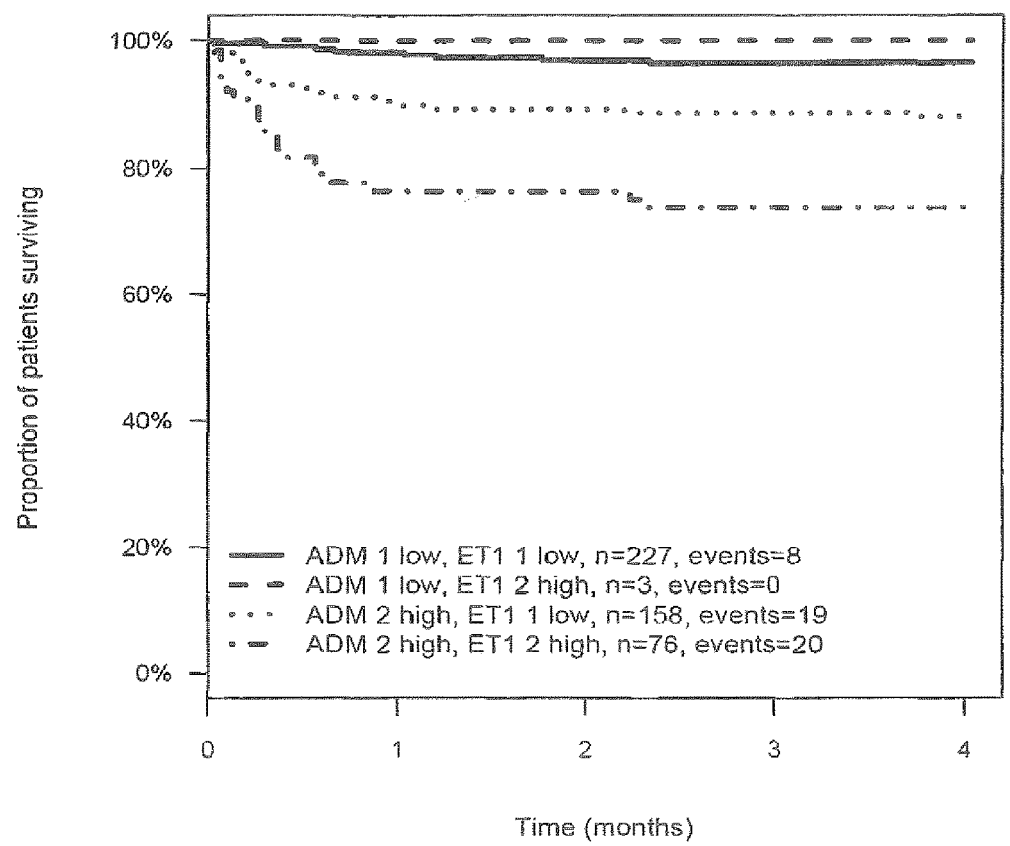
FIG. 14: Kaplan-Meier plot for patients with high and low levels of pre-interventionally measured MR-proADM and CT-proET-1 (pairwise combination of both markers). Solid line: both markers low (below defined threshold); dashed/dotted line: both markers high (above defined threshold); dashed line: first marker low, second marker high; dotted line: first marker high, second marker low.
Figure 15:
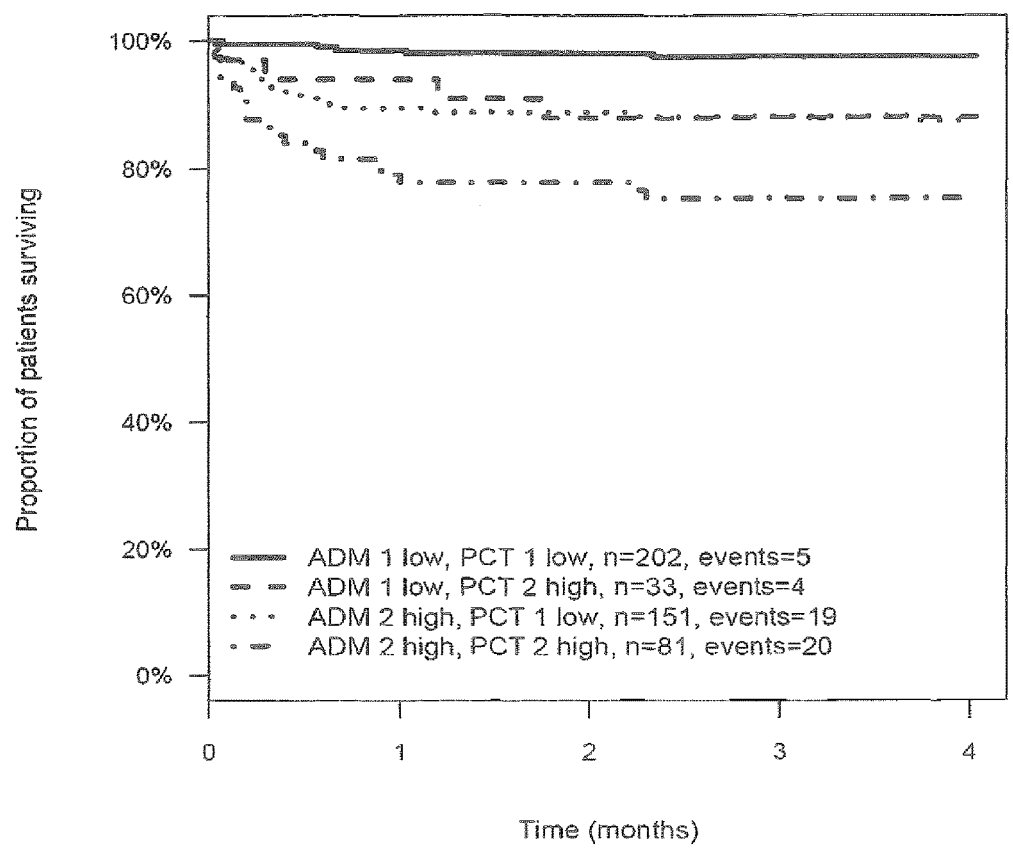
FIG. 15: Kaplan-Meier plot for patients with high and low levels of pre-interventionally measured MR-proADM and PCT (pairwise combination of both markers). Solid line: both markers low (below defined threshold); dashed/dotted line: both markers high (above defined threshold); dashed line: first marker low, second marker high; dotted line: first marker high, second marker low.
Figure 16:
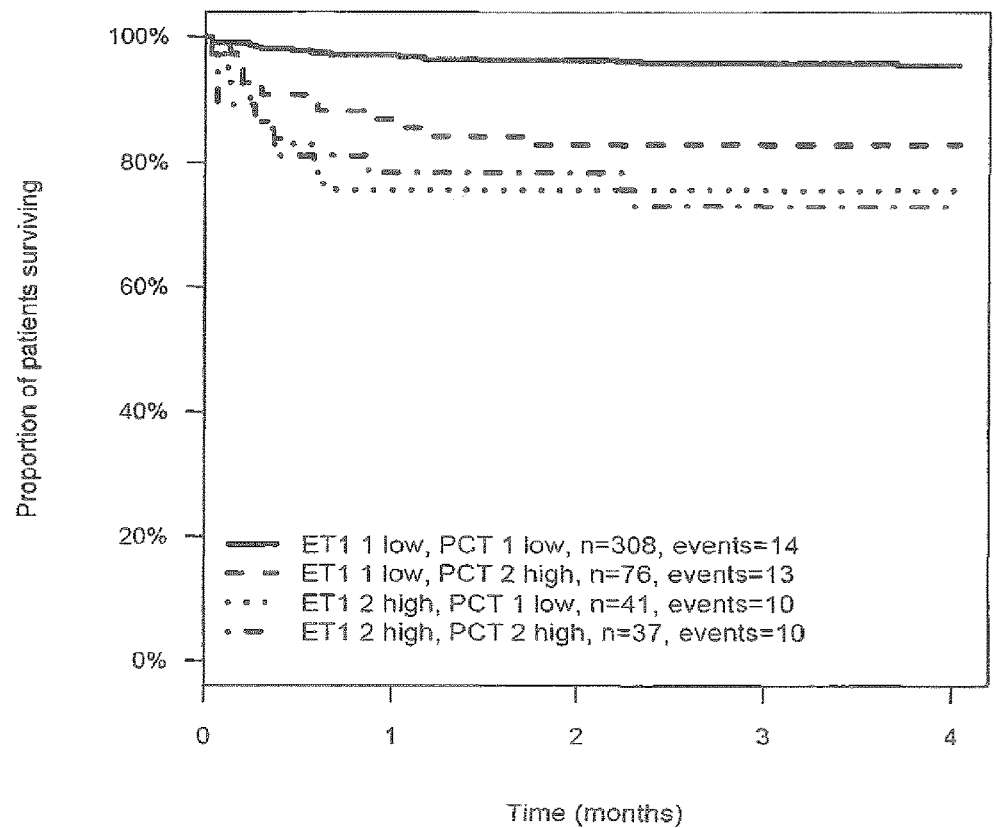
FIG. 16: Kaplan-Meier plot for patients with high and low levels of pre-interventionally measured CT-proET-1 and PCT (pairwise combination of both markers). Solid line: both markers low (below defined threshold); dashed/dotted line: both markers high (above defined threshold); dashed line: first marker low, second marker high; dotted line: first marker high, second marker low.
Figure 17:
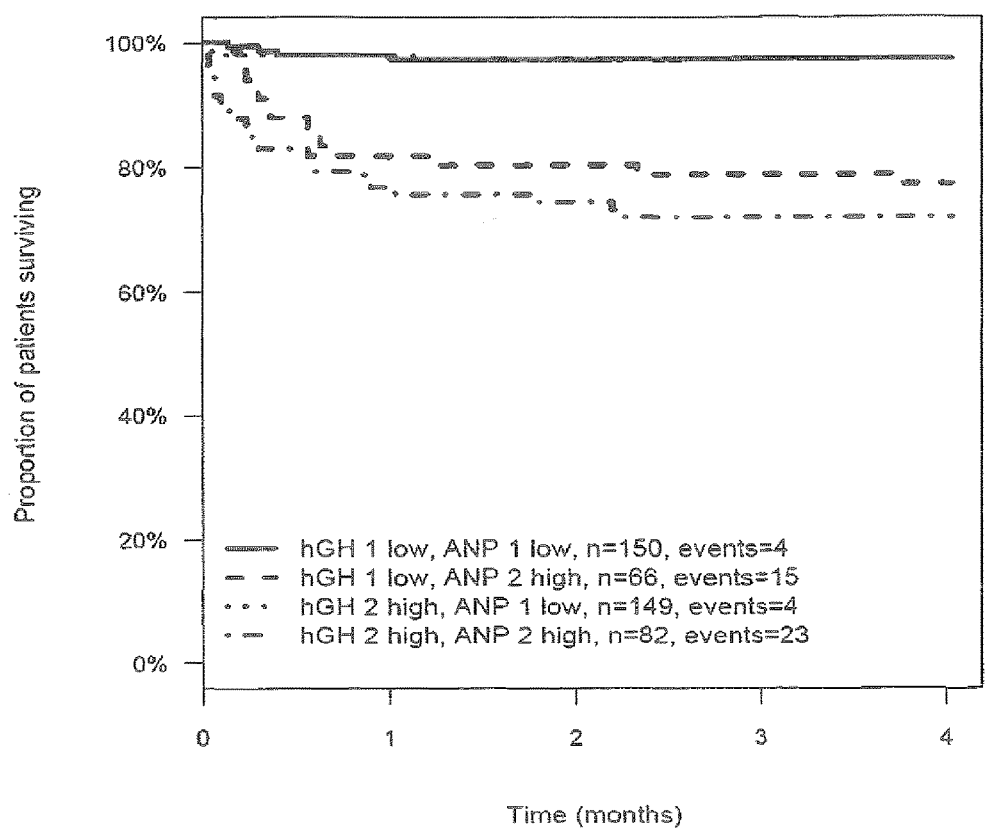
FIG. 17: Kaplan-Meier plot for patients with high and low levels of pre-interventionally measured hGH and MR-proANP (pairwise combination of both markers). Solid line: both markers low (below defined threshold); dashed/ dotted line: both markers high (above defined threshold); dashed line: first marker low, second marker high; dotted line: first marker high, second marker low.
Figure 18:
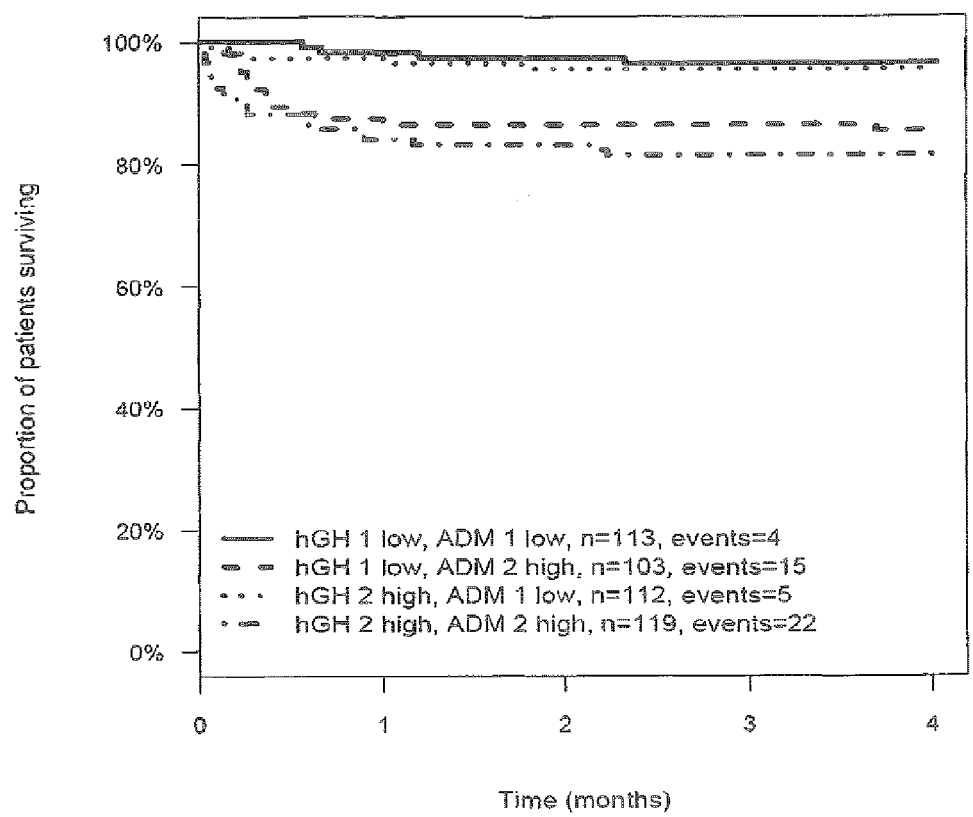

FIG. 18: Kaplan-Meier plot for patients with high and low levels of pre-interventionally measured hGH and MR-proADM (pairwise combination of both markers). Solid line: both markers low (below defined threshold); dashed/dotted line: both markers high (above defined threshold); dashed line: first marker low, second marker high; dotted line: first marker high, second marker low.

Figure 19:
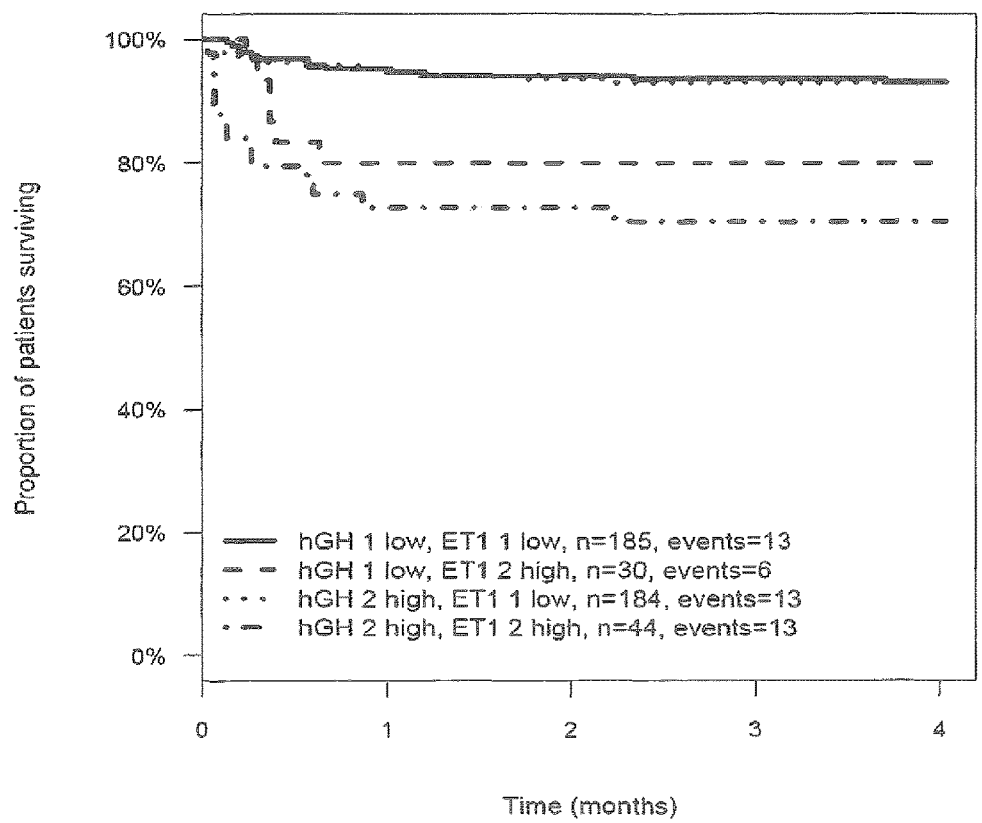

FIG. 19: Kaplan-Meier plot for patients with high and low levels of pre-interventionally measured hGH and CT-proET-1 (pairwise combination of both markers). Solid line: both markers low (below defined threshold); dashed/dotted line: both markers high (above defined threshold); dashed line: first marker low, second marker high; dotted line: first marker high, second marker low.

Figure 20:
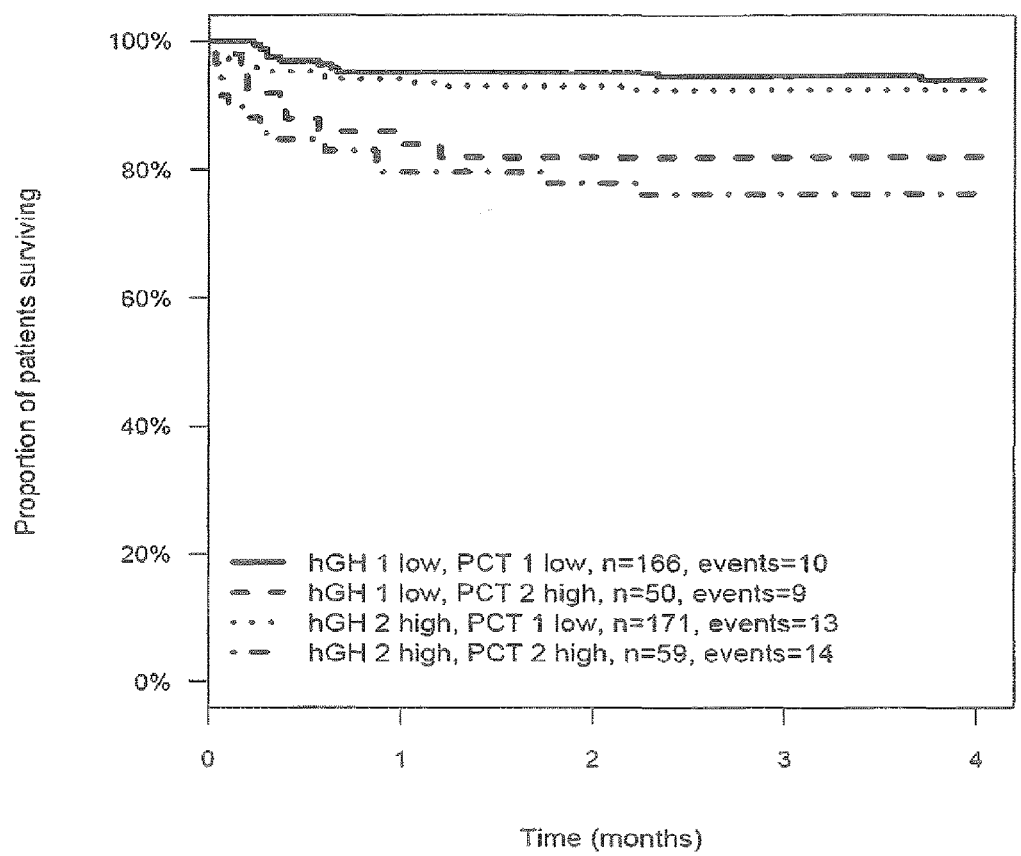

FIG. 20: Kaplan-Meier plot for patients with high and low levels of pre-interventionally measured hGH and PCT (pairwise combination of both markers). Solid line: both markers low (below defined threshold); dashed/dotted line: both markers high (above defined threshold); dashed line: first marker low, second marker high; dotted line: first marker high, second marker low.

Figure 21:
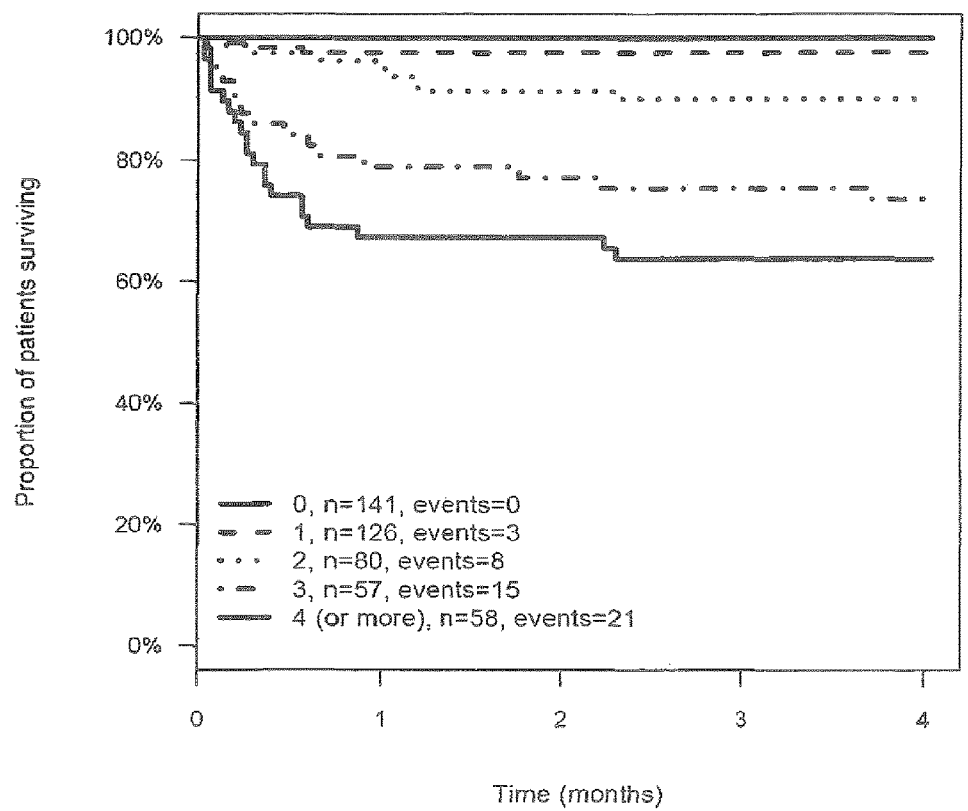

FIG. 21: Kaplan-Meier plot for patients with high levels of MR-proANP, MR-proADM, CT-proAVP, CT-proET-1 and/or PCT. Upper to lower curve: 0, 1, 2, 3 and 4 or more of the markers above defined threshold.

Figure 22:
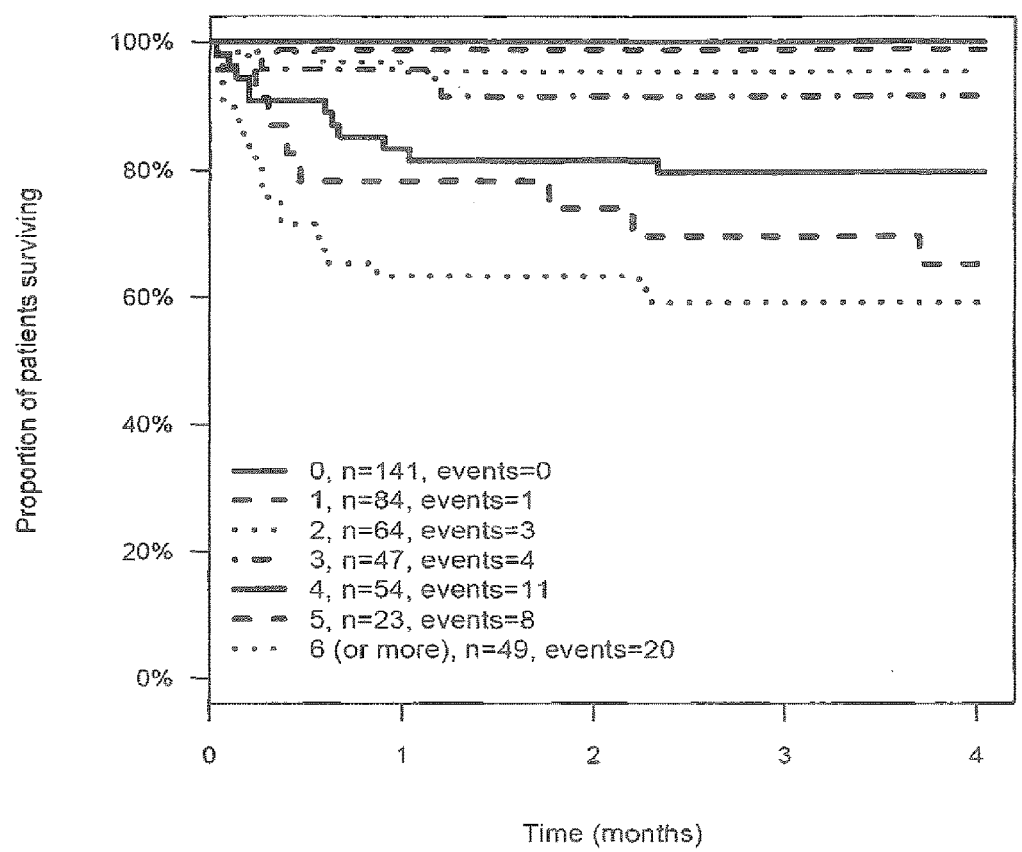

FIG. 22: Kaplan-Meier plot for patients with high levels of pre-interventionally measured MR-proANP, MR-proADM, CT-proAVP, CT-proET-1 and/or PCT. MR-proANP and CT-proAVP have been counted twice. Upper to lower curve: 0, 1, 2, 3, 4, 5 and 6 or more of the markers above defined threshold.

Figure 23:
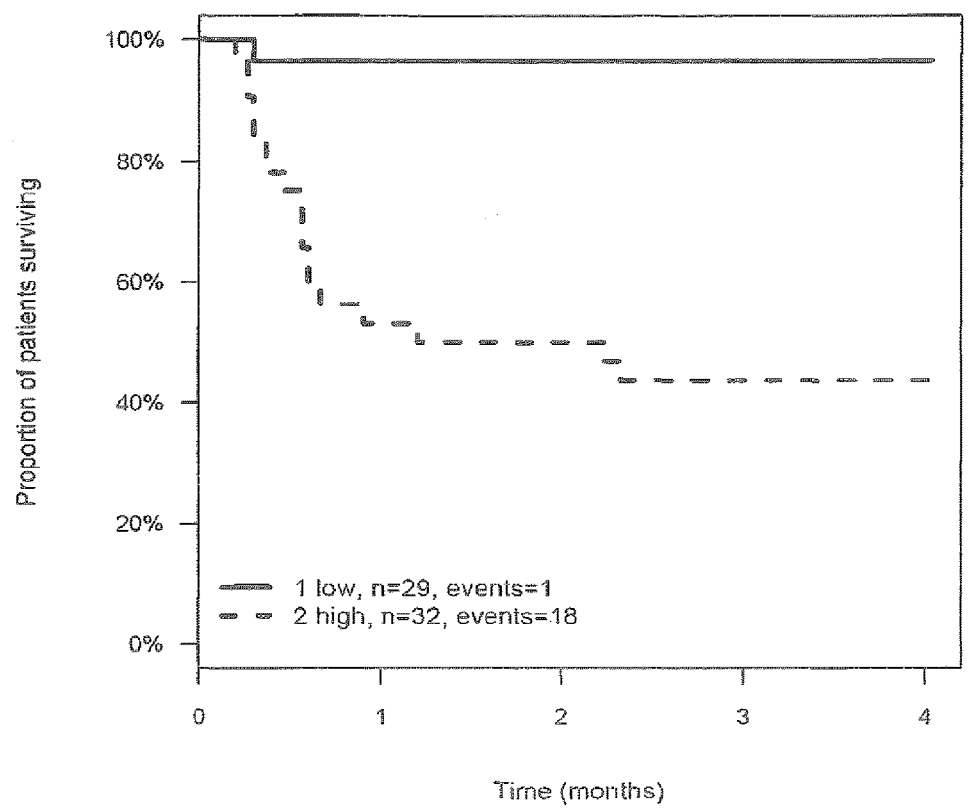

FIG. 23: Kaplan-Meier plot for patients with high and low levels of pre-interventionally measured MR-proANP and a modified Rankin Scale of 5 on day 5.

Figure 24:
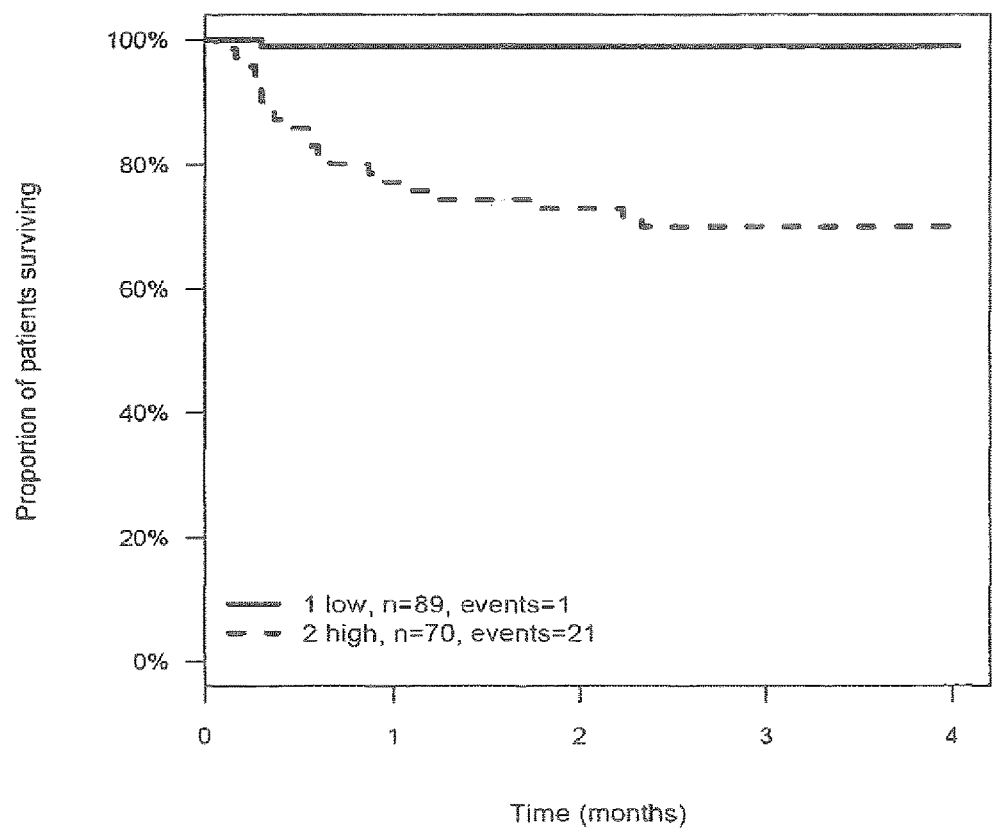

FIG. 24: Kaplan-Meier plot for patients with high and low levels of pre-interventionally measured MR-proANP and a Barthel Index <85% on day 5.

Figure 25:
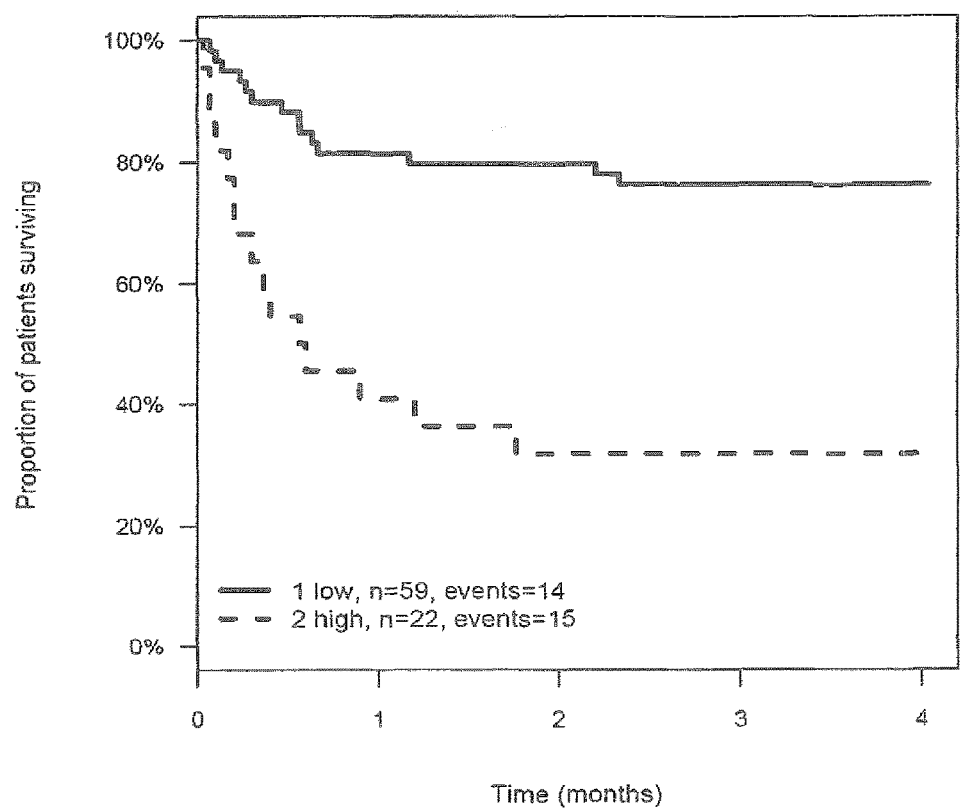

FIG. 25: Kaplan-Meier plot for patients with high and low levels of pre-interventionally measured PCT and a NIHSS Index <10 on day 1.

Figure 26:
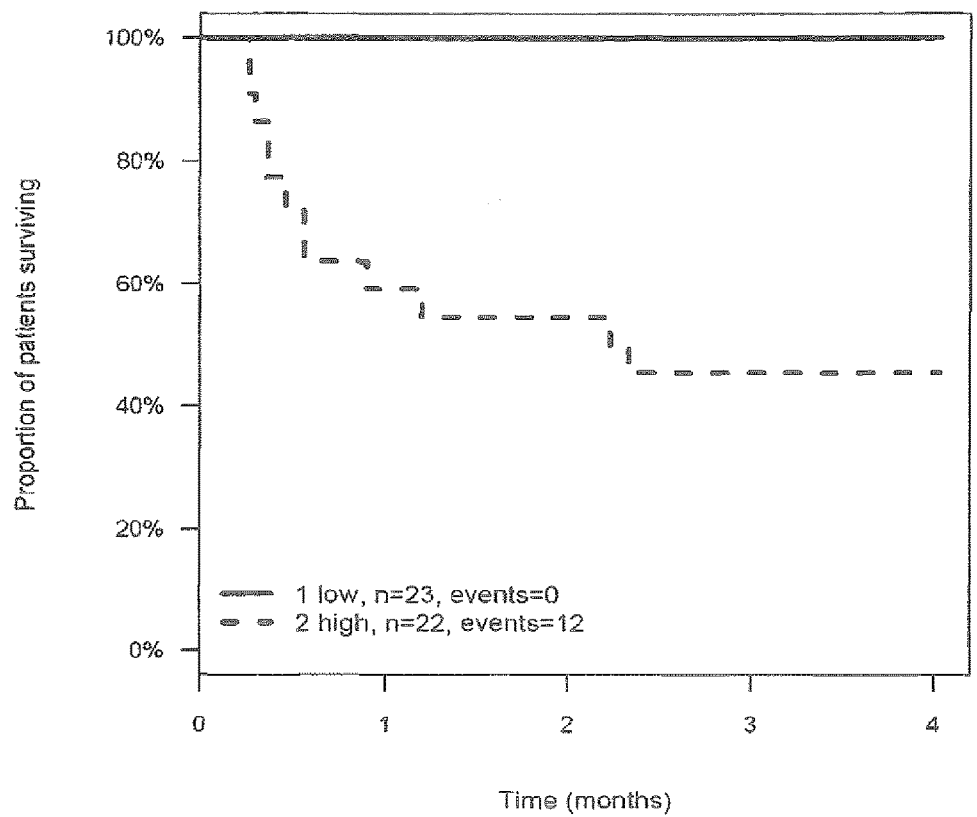

FIG. 26: Kaplan-Meier plot for patients with high and low levels of pre-interventionally measured MR-proANP and a NIHSS Index <10 on day 5.

Figure 27:
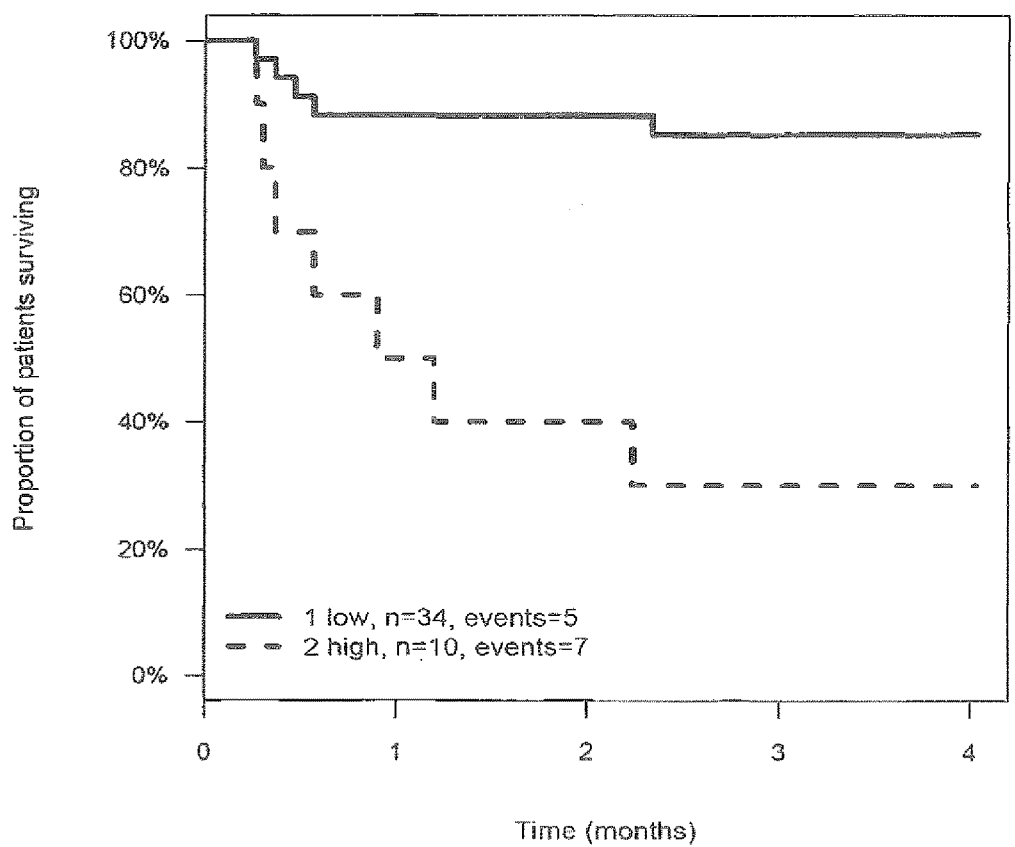

FIG. 27: Kaplan-Meier plot for patients with high and low levels of pre-interventionally measured PCT and a NIHSS Index <10 on day 1.

Figure 28:
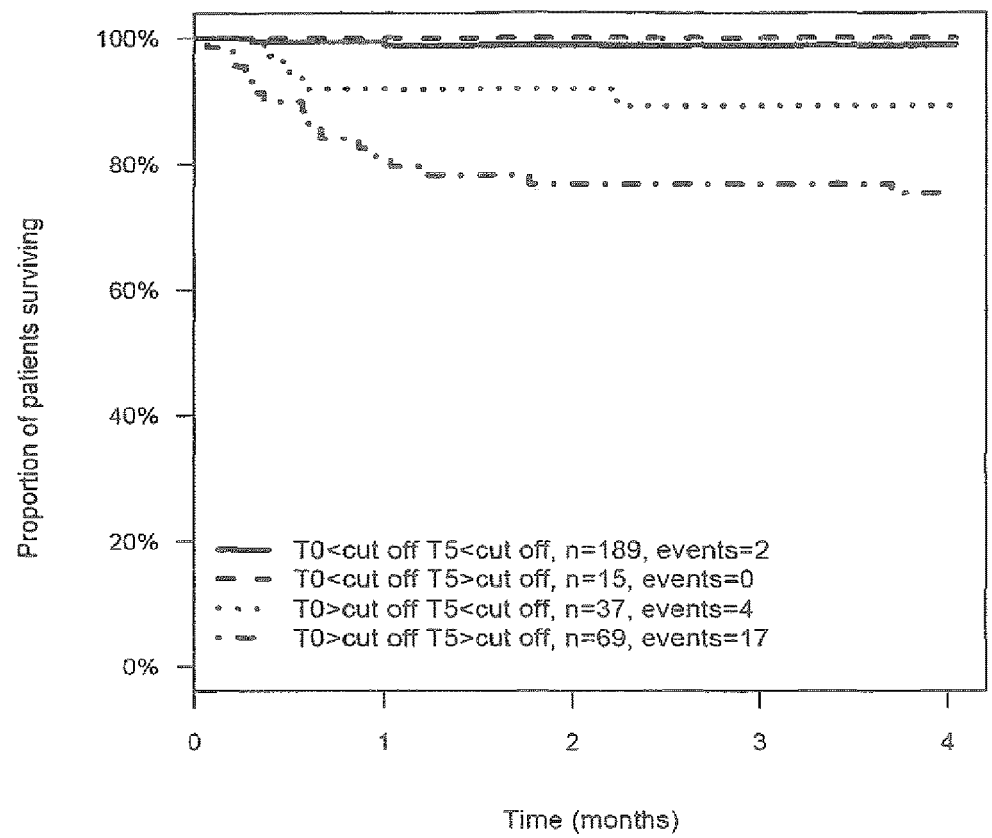

FIG. 28: Kaplan-Meier plot for patients with high and low levels of MR-proANP measured pre-interventionally (day 0) and/or day 5. Solid line: level below threshold on day 0 and day 5; dashed line: level below threshold on day 0 and above threshold on day 5; dotted lined: level above threshold on day 0 and below threshold on day 5; dashed/dotted line: level above threshold on day 0 and day 5.

Figure 29:
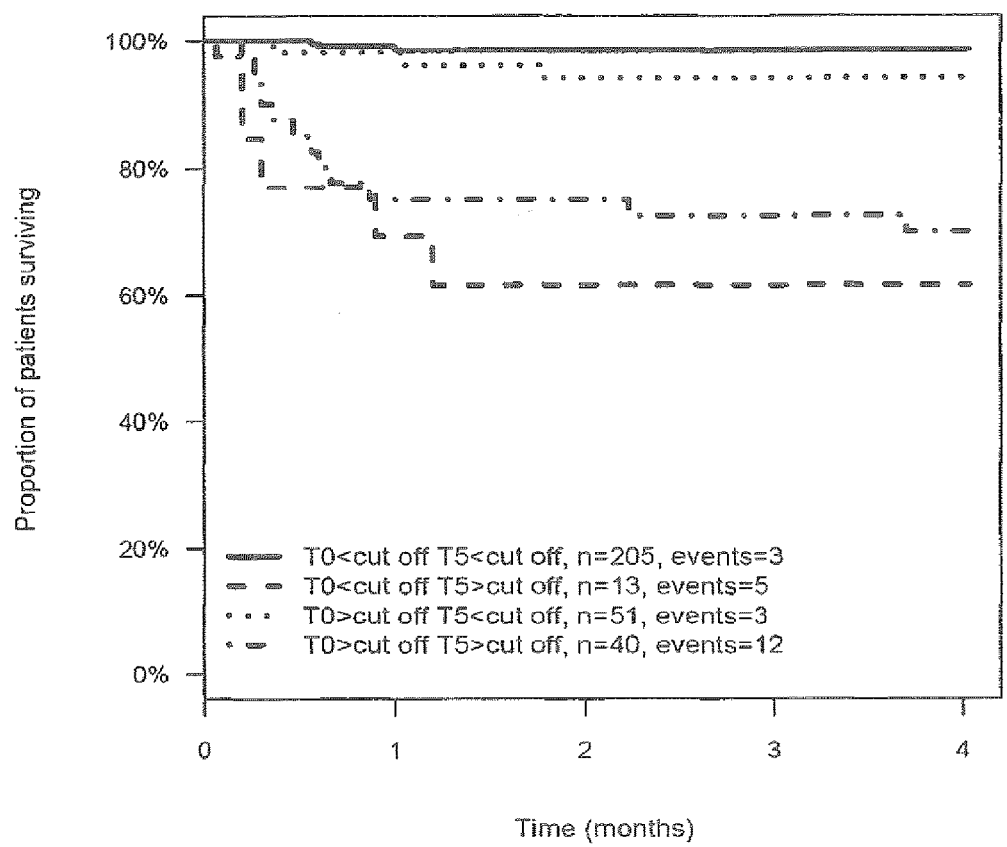

FIG. 29: Kaplan-Meier plot for patients with high and low levels of CT-proAVP measured pre-interventionally (day 0) and/or day 5. Solid line: level below threshold on day 0 and day 5; dashed line: level below threshold on day 0 and above threshold on day 5; dotted lined: level above threshold on day 0 and below threshold on day 5; dashed/dotted line: level above threshold on day 0 and day 5.

Figure 30:
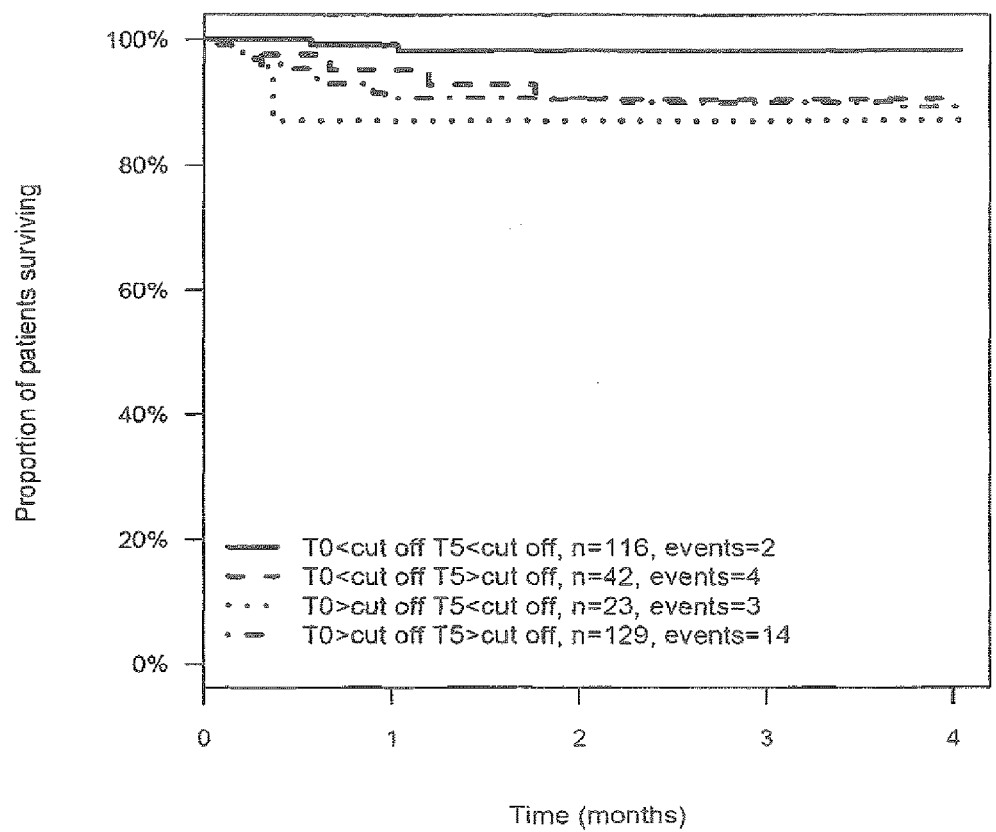

FIG. 30: Kaplan-Meier plot for patients with high and low levels of MR-proADM measured pre-interventionally (day 0) and/or day 5. Solid line: level below threshold on day 0 and day 5; dashed line: level below threshold on day 0 and above threshold on day 5; dotted lined: level above threshold on day 0 and below threshold on day 5; dashed/dotted line: level above threshold on day 0 and day 5.

Figure 31:
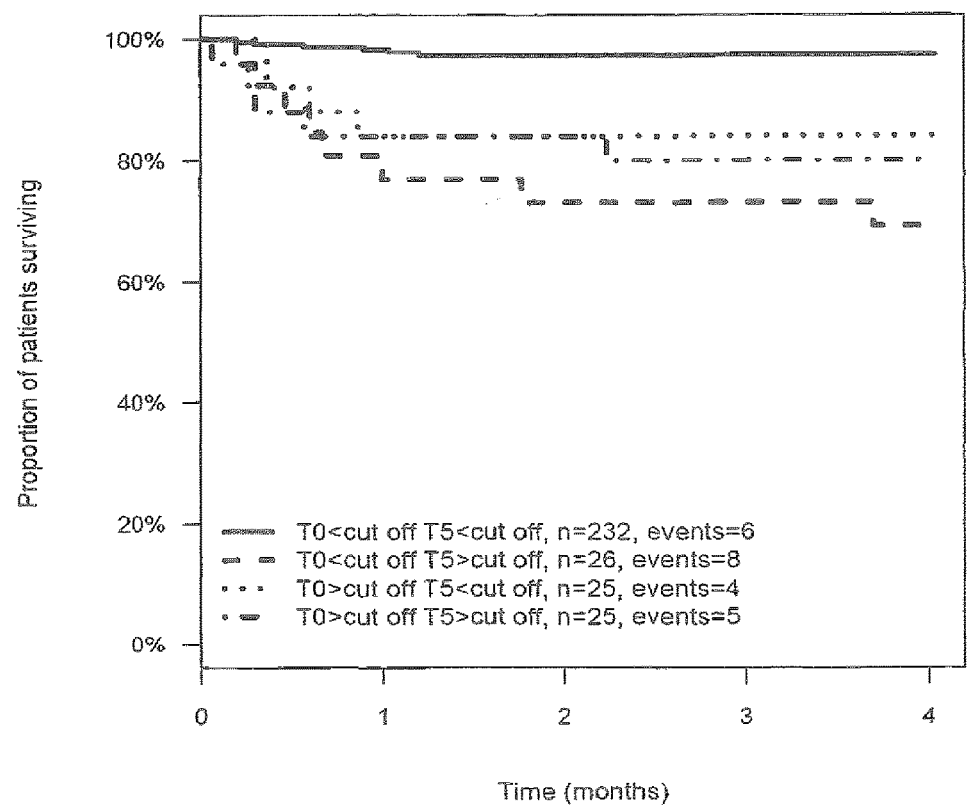

FIG. 31: Kaplan-Meier plot for patients with high and low levels of CT-proET-1 measured pre-interventionally (day 0) and/or day 5. Solid line: level below threshold on day 0 and day 5; dashed line: level below threshold on day 0 and above threshold on day 5; dotted lined: level above threshold on day 0 and below threshold on day 5; dashed/dotted line: level above threshold on day 0 and day 5.

Figure 32:
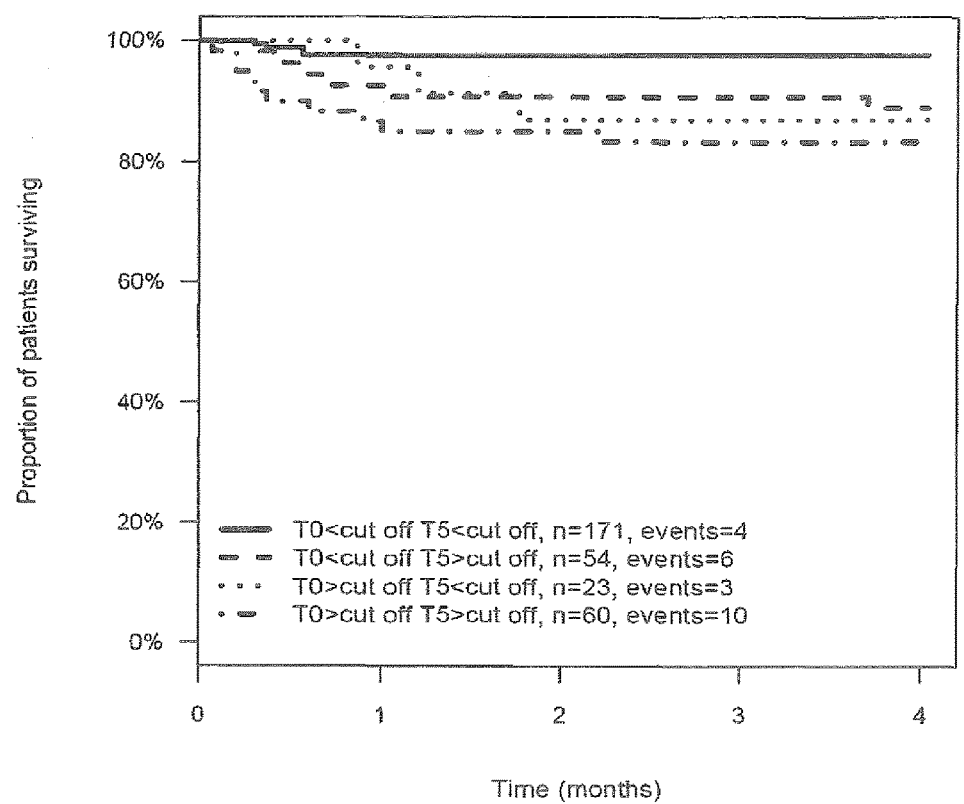

FIG. 32: Kaplan-Meier plot for patients with high and low levels of PCT measured pre-interventionally (day 0) and/or day 5. Solid line: level below threshold on day 0 and day 5; dashed line: level below threshold on day 0 and above threshold on day 5; dotted lined: level above threshold on day 0 and below threshold on day 5; dashed/dotted line: level above threshold on day 0 and day 5.

Figure 33:
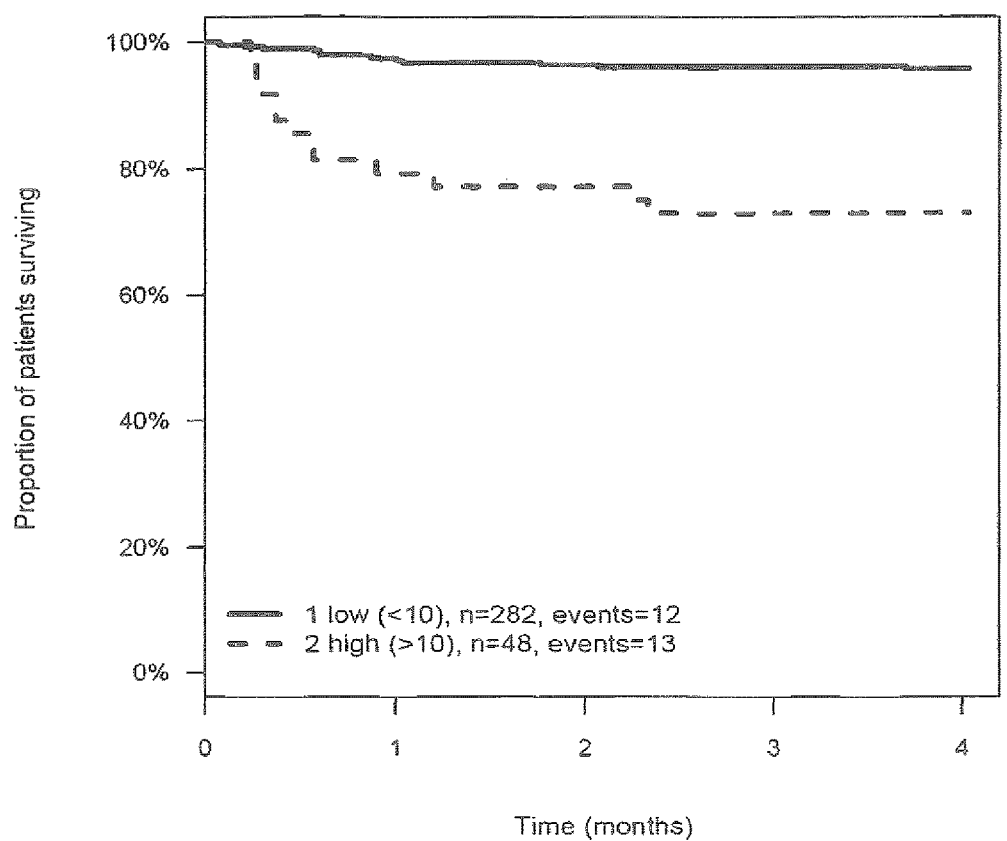

FIG. 33: Kaplan-Meier plot for patients with high NIHSS (>10) and low NIHSS (<10) on day 5.

Figure 34:
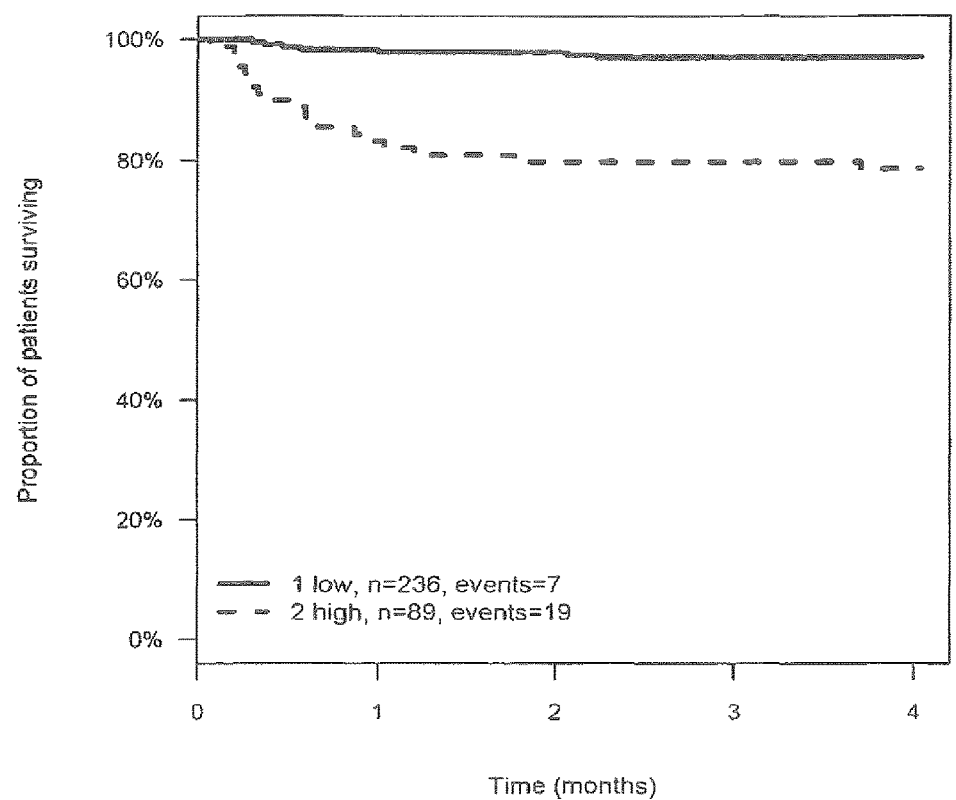

FIG. 34: Kaplan-Meier plot for patients with high/low levels of MR-proANP measured on day 5.

Figure 35:
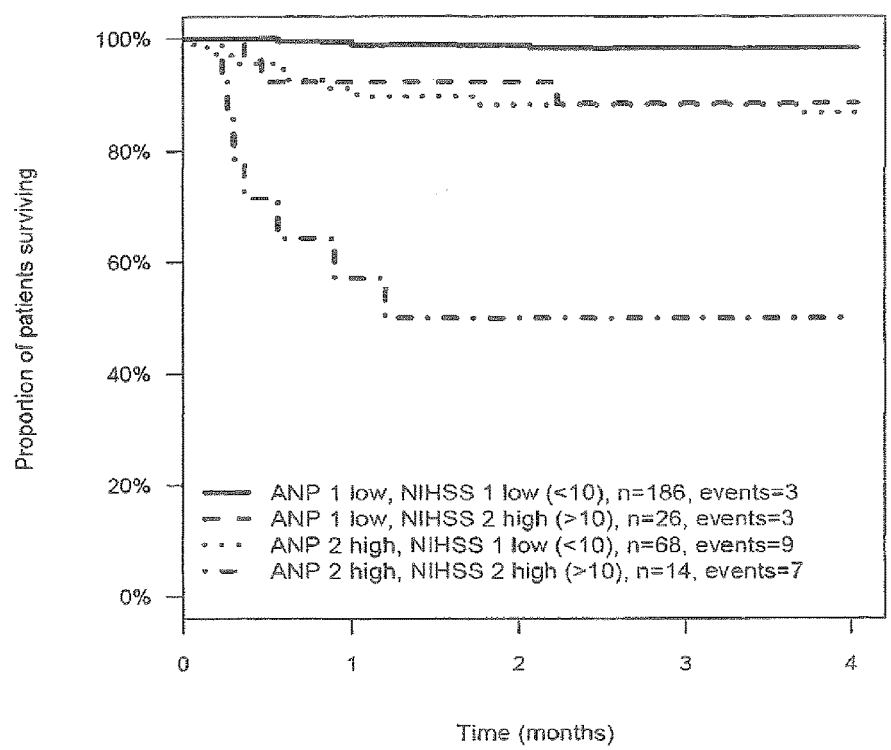

FIG. 35: Kaplan-Meier plot for patients with high/low levels of MR-proANP and high/low NIHSS on day 5. Solid line: marker level low, NIHSS low; dashed line: marker level low, NIHSS high; dotted line: marker level high, NIHSS low, dashed/dotted line: marker level high, and NIHSS high.

Figure 36:
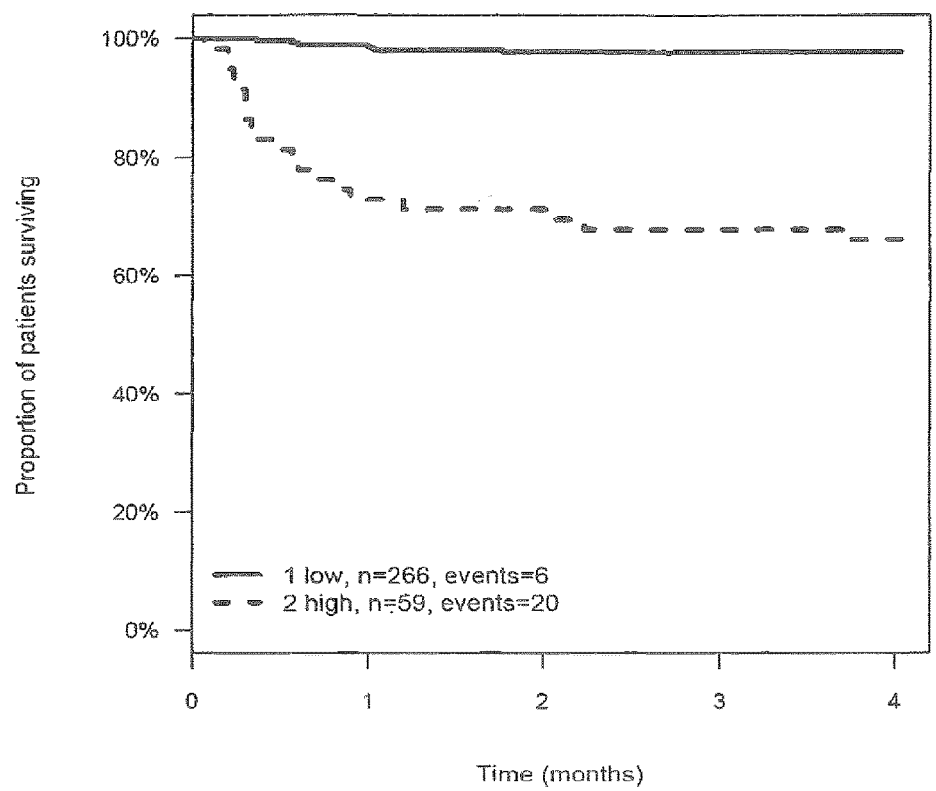

FIG. 36: Kaplan-Meier plot for patients with high/low levels of CT-proAVP on day 5.

Figure 37:
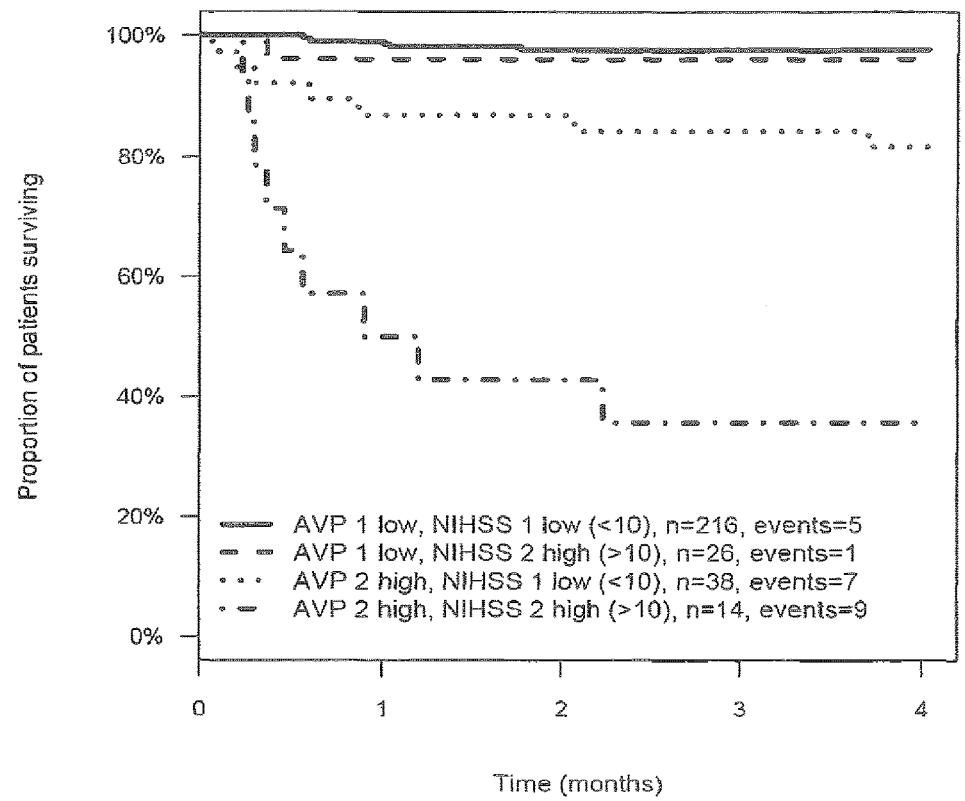

FIG. 37: Kaplan-Meier plot for patients with high/low levels of CT-proAVP and high/low NIHSS on day 5. Solid line: marker level low, NIHSS low; dashed line: marker level low, NIHSS high; dotted line: marker level high, NIHSS low, dashed/dotted line: marker level high, and NIHSS high.

Figure 38:
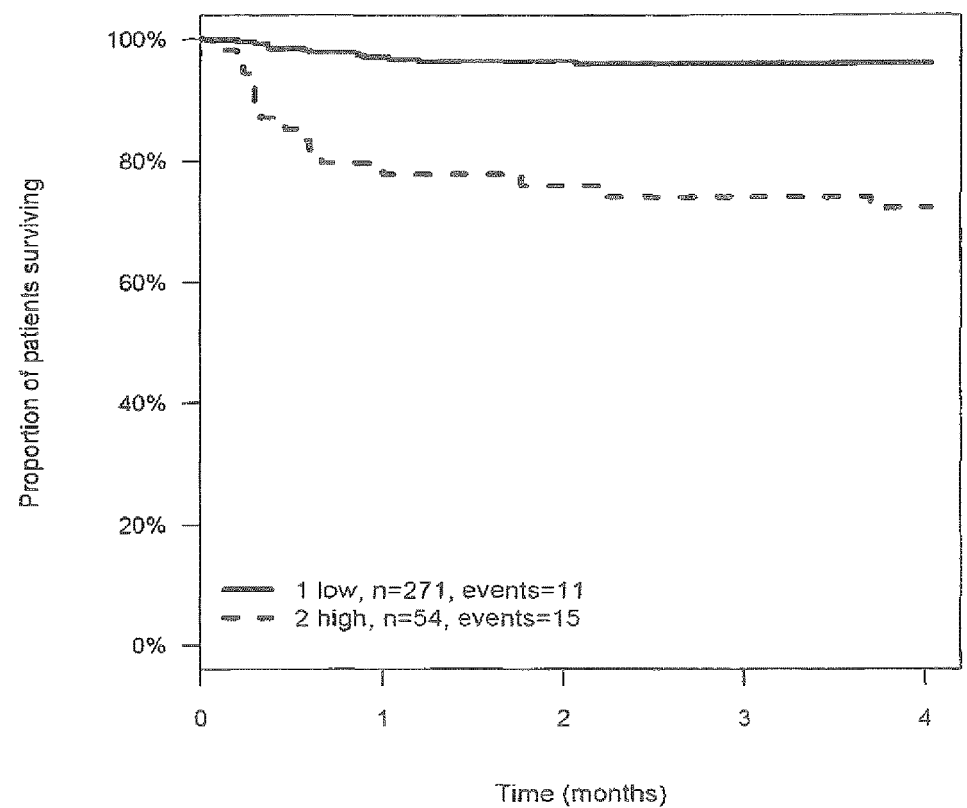

FIG. 38: Kaplan-Meier plot for patients with high/low levels of CT-proET-1 on day 5.

Figure 39:
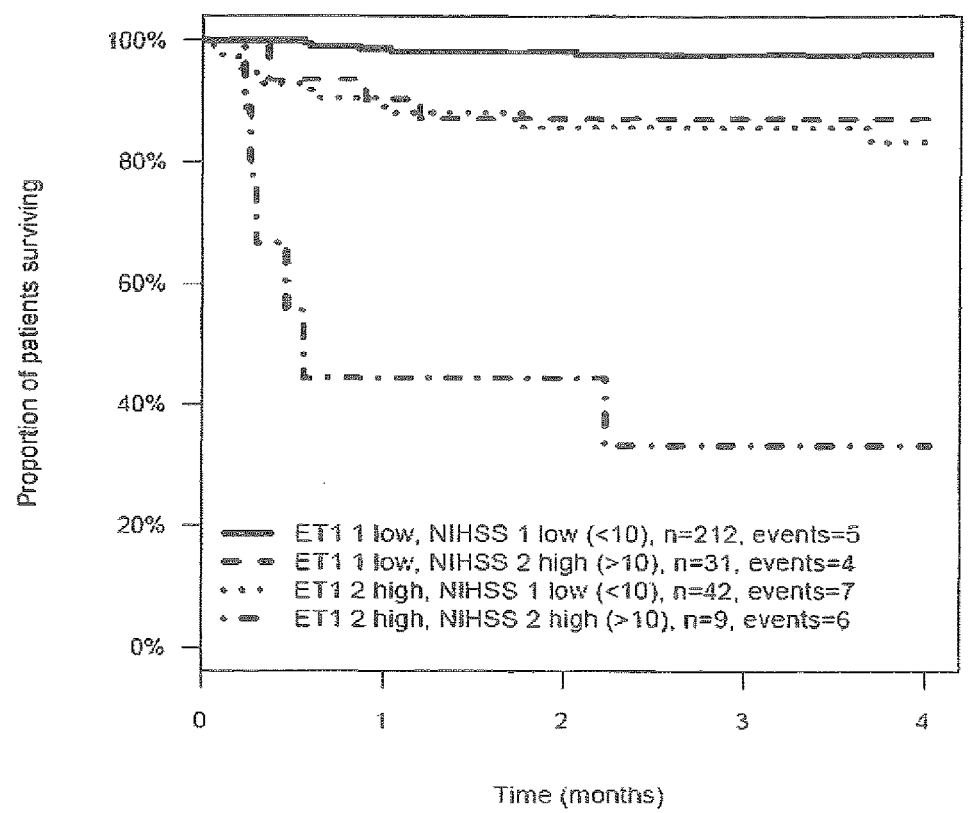

FIG. 39: Kaplan-Meier plot for patients with high/low levels of CT-proET-1 and high/low NIHSS on day 5. Solid line: marker level low, NIHSS low; dashed line: marker level low, NIHSS high; dotted line: marker level high, NIHSS low, dashed/dotted line: marker level high, and NIHSS high.

Figure 40:
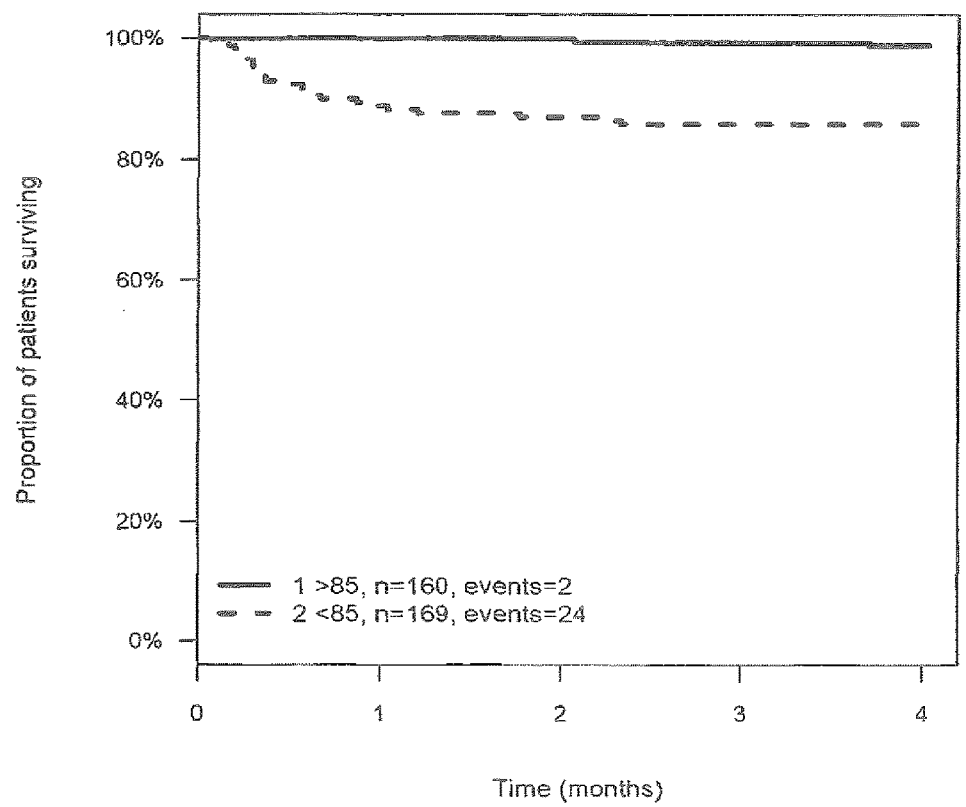

FIG. 40: Kaplan-Meier plot for patients with Barthel Index <85% (dashed line) and >85% (solid line) on day 5.

Figure 41:
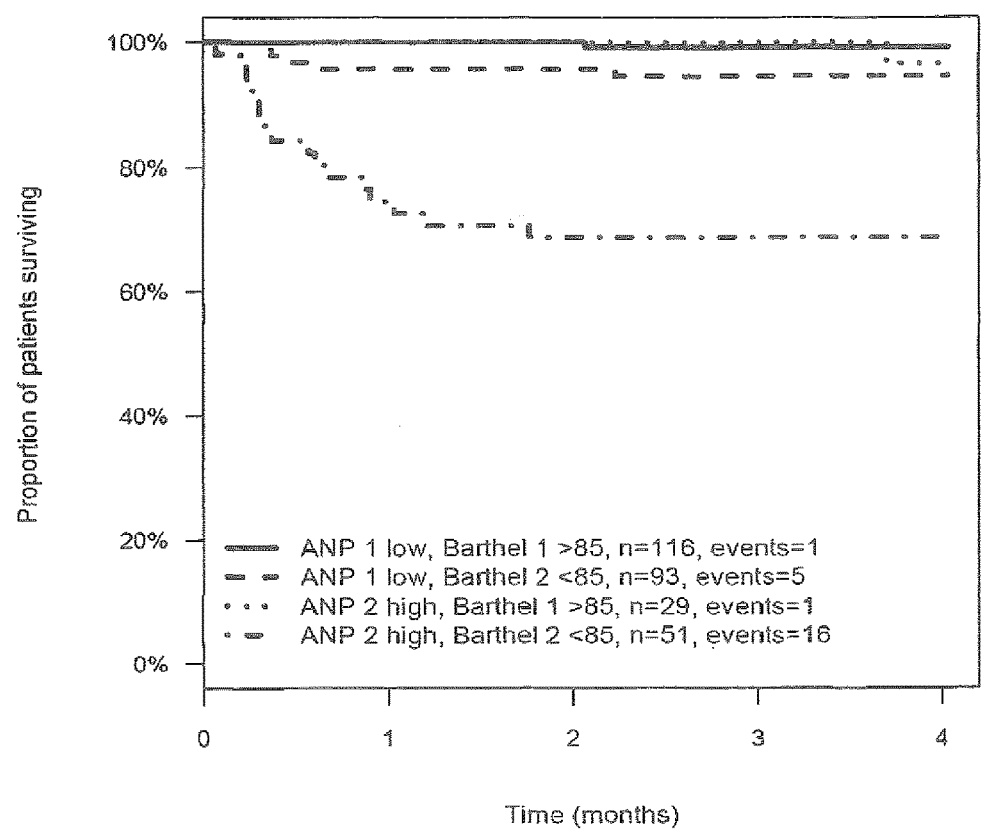

FIG. 41: Kaplan-Meier plot for patients with high/low levels of MR-proANP and Barthel Index </>85% on day 5. Solid line: marker level low, Barthel Index >85%; dashed line: marker level low, Barthel Index <85%; dotted line: marker level high, Barthel Index >85%, dashed/dotted line: marker level high, and Barthel Index <85%.

Figure 42:
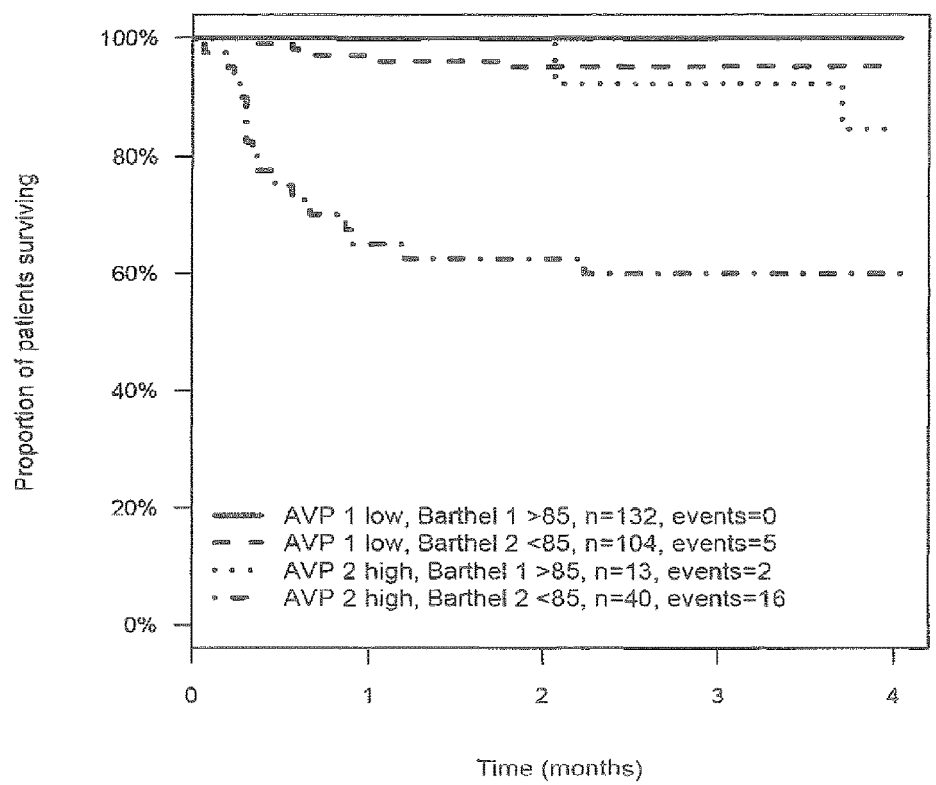

FIG. 42: Kaplan-Meier plot for patients with high/low levels of CT-proAVP and Barthel Index </>85% on day 5. Solid line: marker level low, Barthel Index >85%; dashed line: marker level low, Barthel Index <85%; dotted line: marker level high, Barthel Index >85%, dashed/dotted line: marker level high, and Barthel Index <85%.

Figure 43:
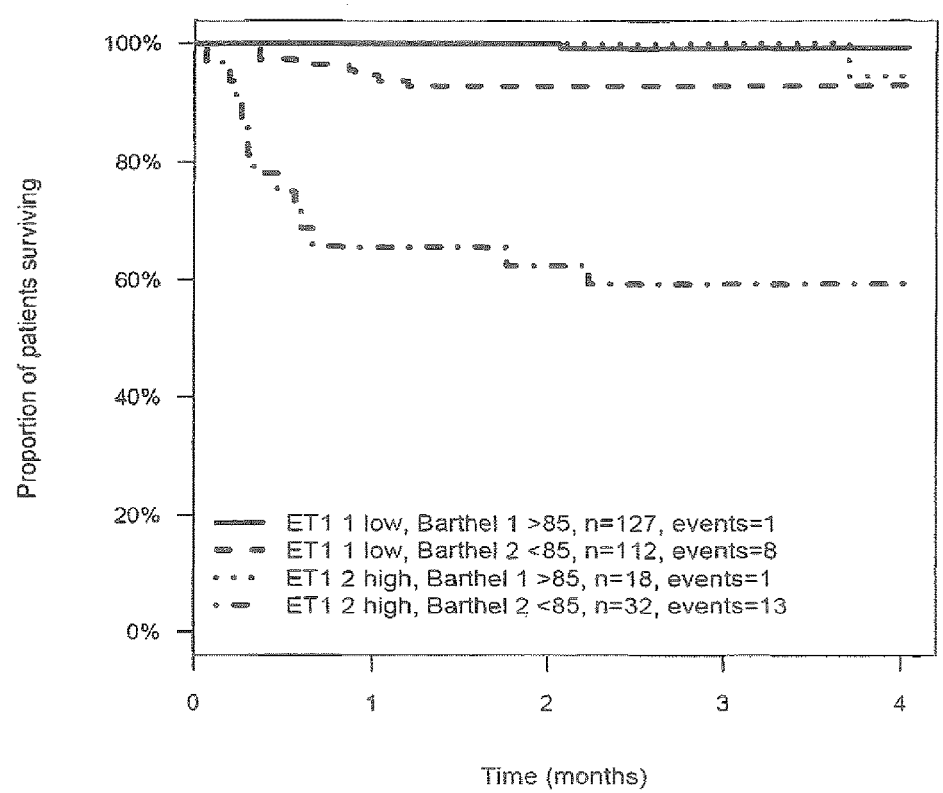

FIG. 43: Kaplan-Meier plot for patients with high/low levels of CT-proET-1 and Barthel Index </>85% on day 5. Solid line: marker level low, Barthel Index >85%; dashed line: marker level low, Barthel Index <85%; dotted line: marker level high, Barthel Index >85%, dashed/dotted line: marker level high, and Barthel Index <85%.

Figure 44:
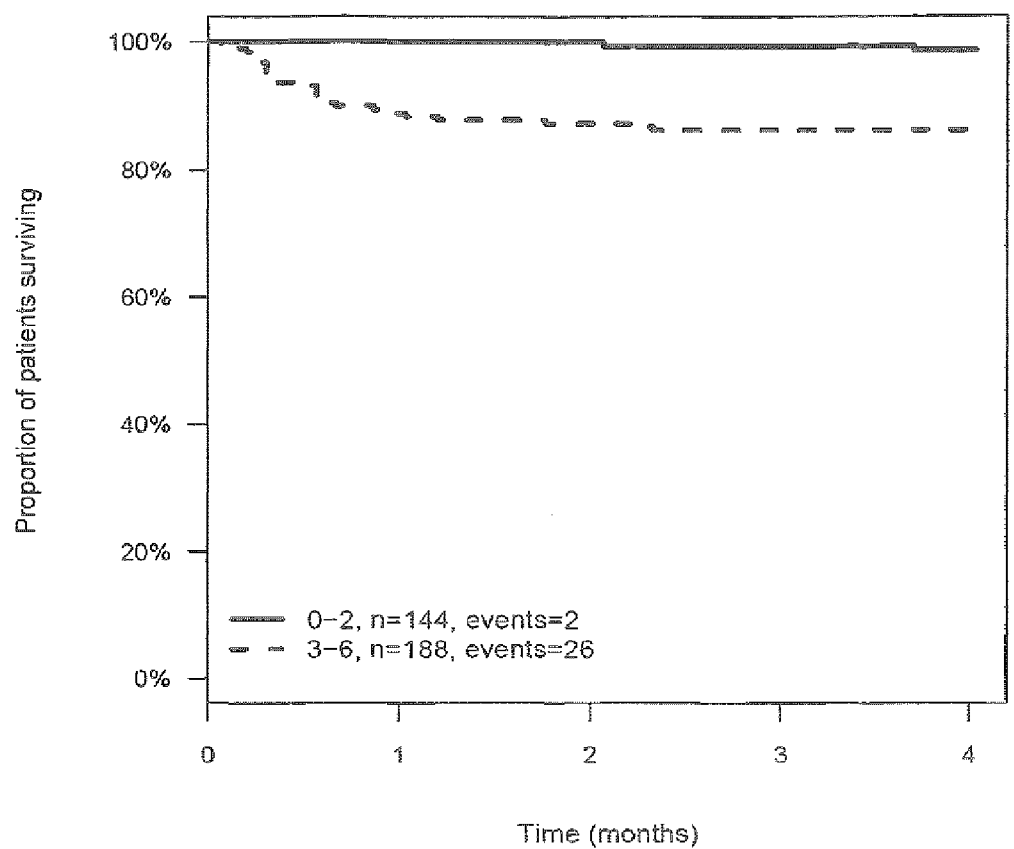

FIG. 44: Kaplan-Meier plot for patients with a modified Rankin Scale Score of 0-2 (solid line) and 3-6 (dashed line) on day 5.

Figure 45:
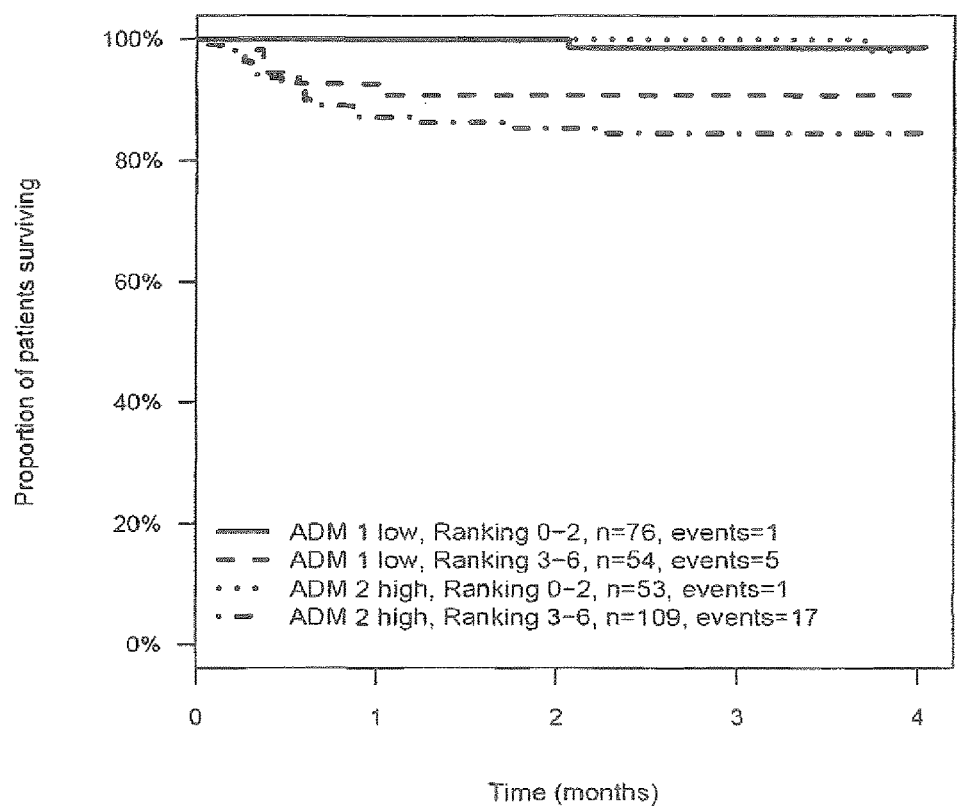

FIG. 45: Kaplan-Meier plot for patients with high/low levels of MR-proANP and a modified Rankin Scale Score between 0-2 or 3-6 on day 5. Solid line: marker level low, Rankin 0-2; dashed line: marker level low, Rankin 3-6; dotted line: marker level high, Rankin 0-2, dashed/dotted line: marker level high, and Rankin 3-6.

Figure 46:
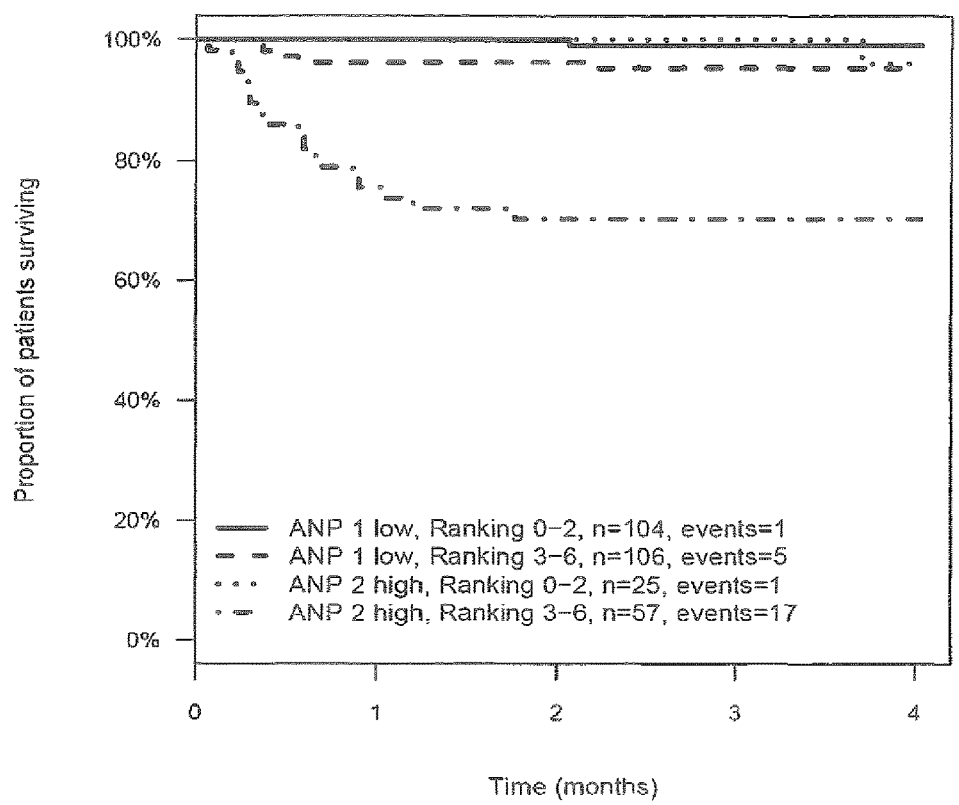

FIG. 46: Kaplan-Meier plot for patients with high/low levels of MR-proADM and a modified Rankin Scale Score between 0-2 or 3-6 on day 5. Solid line: marker level low, Rankin 0-2; dashed line: marker level low, Rankin 3-6; dotted line: marker level high, Rankin 0-2, dashed/dotted line: marker level high, and Rankin 3-6.

Figure 47:
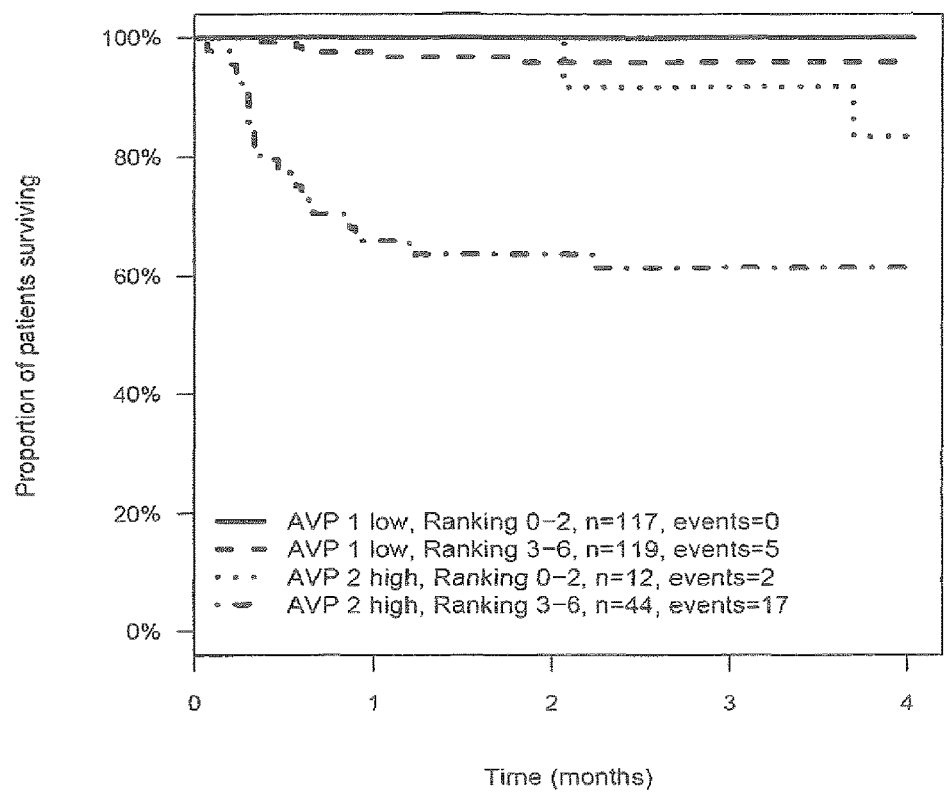

FIG. 47: Kaplan-Meier plot for patients with high/low levels of CT-proAVP and a modified Rankin Scale Score between 0-2 or 3-6 on day 5. Solid line: marker level low, Rankin 0-2; dashed line: marker level low, Rankin 3-6; dotted line: marker level high, Rankin 0-2, dashed/dotted line: marker level high, and Rankin 3-6.

Figure 48:
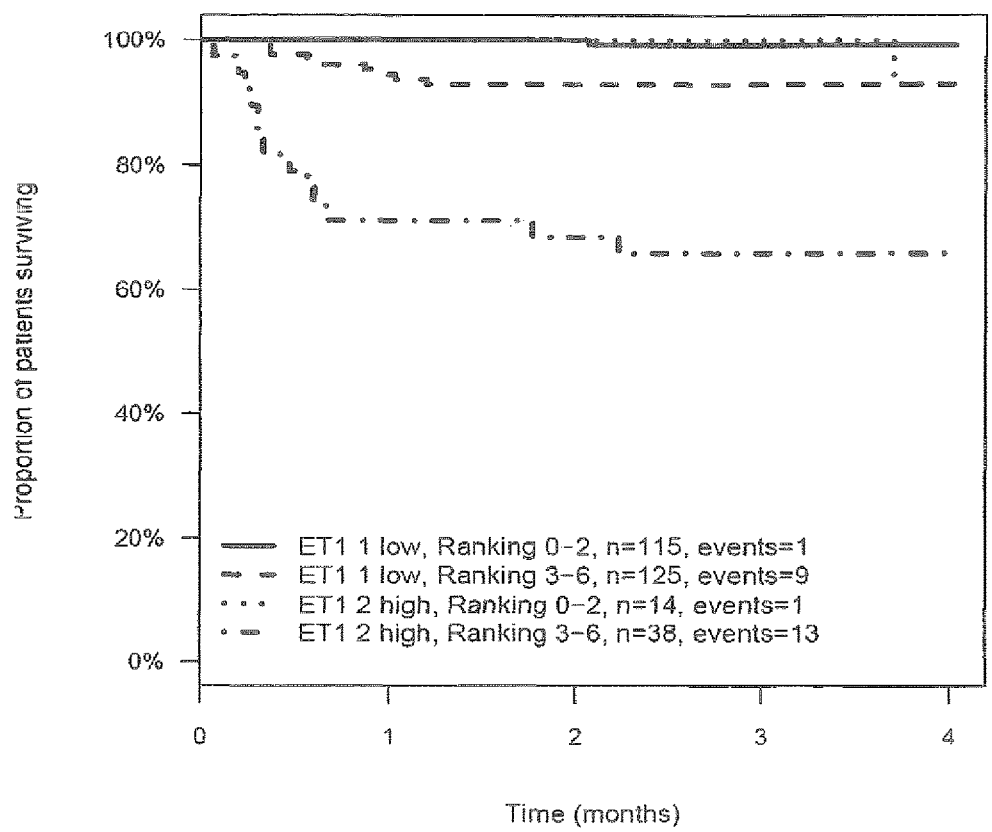

FIG. 48: Kaplan-Meier plot for patients with high/low levels of CT-proET-1 and a modified Rankin Scale Score between 0-2 or 3-6 on day 5. Solid line: marker level low, Rankin 0-2; dashed line: marker level low, Rankin 3-6; dotted line: marker level high, Rankin 0-2, dashed/dotted line: marker level high, and Rankin 3-6.

Figure 49:
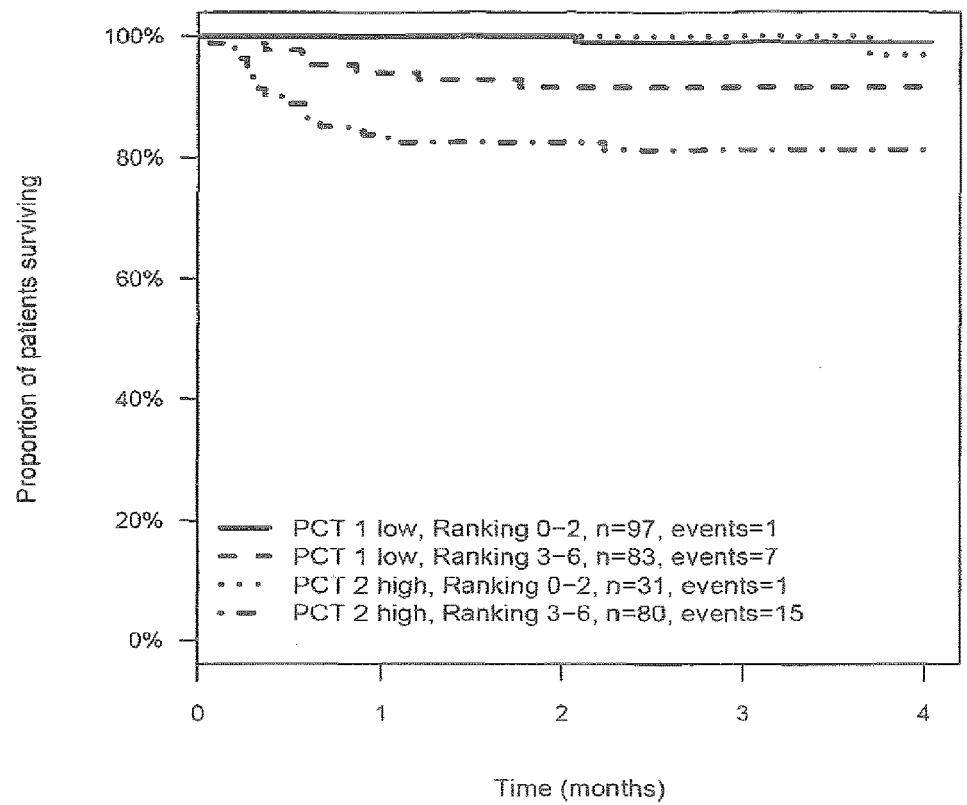

FIG. 49: Kaplan-Meier plot for patients with high/low levels of PCT and a modified Rankin Scale Score between 0-2 or 3-6 on day 5. Solid line: marker level low, Rankin 0-2; dashed line: marker level low, Rankin 3-6; dotted line: marker level high, Rankin 0-2, dashed/dotted line: marker level high, and Rankin 3-6.

Figure 50:
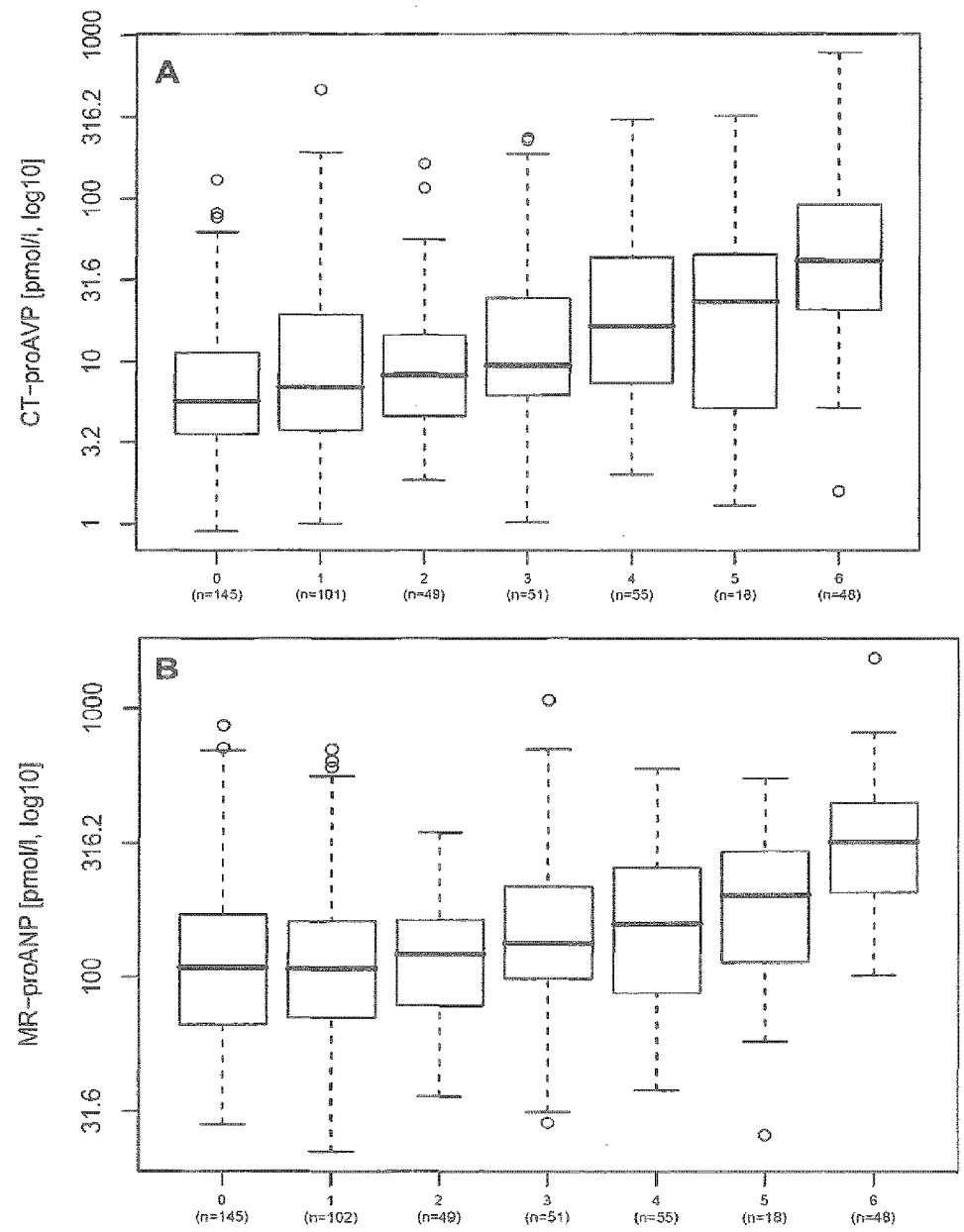

FIG. 50: Box plot of correlation between the modified Rankin Scale determined after 3 months and the level of pre-interventionally measured CT-proAVP (A) and MR-proANP (B), respectively. Rankin 0 to 6 on x-axis from left to right.

Figure 51:
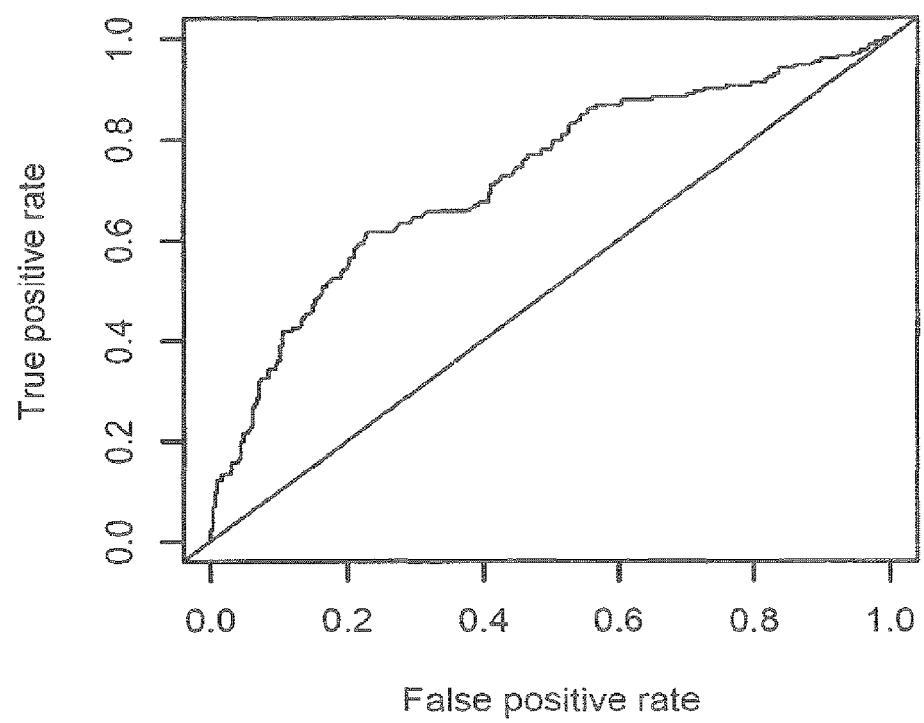

FIG. 51: Receiver Operating characteristics (ROC) plot for pre-interventionally measured CT-pro A VP and dichotomized modified Rankin Scale after 3 months (good outcome=mRS 0-2; bad outcome=mRS 3-6). Area under the curve (AUC)=0.723.

Figure 52:
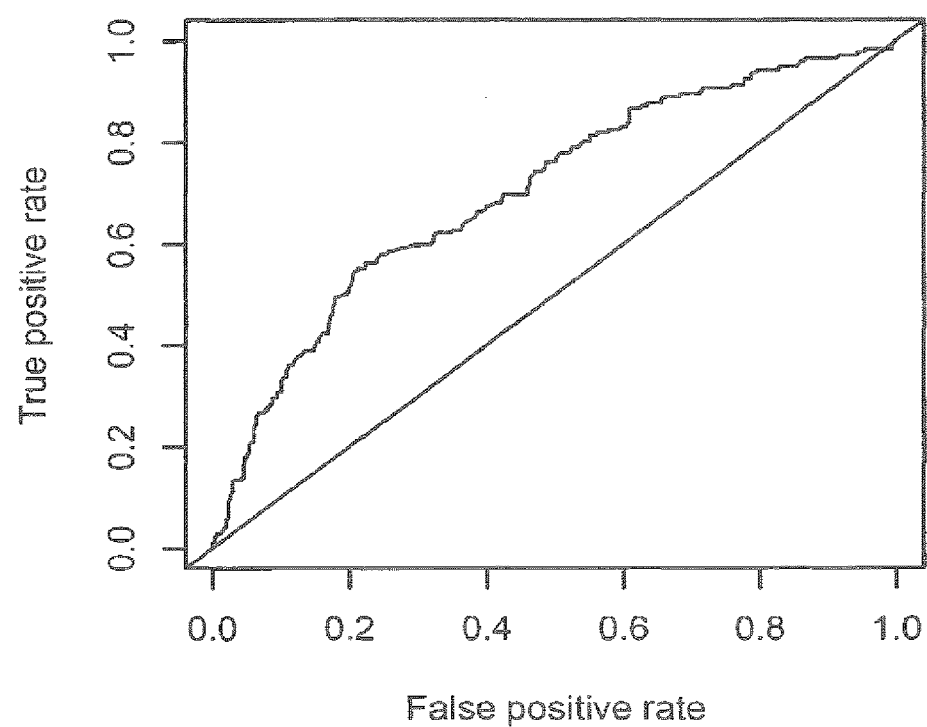

FIG. 52: ROC plot for pre-interventionally measured MR-proANP and dichotomized modified Rankin Scale after 3 months (good outcome=mRS 0-2; bad outcome=mRS 3-6). AUC=0.703.

Figure 53:
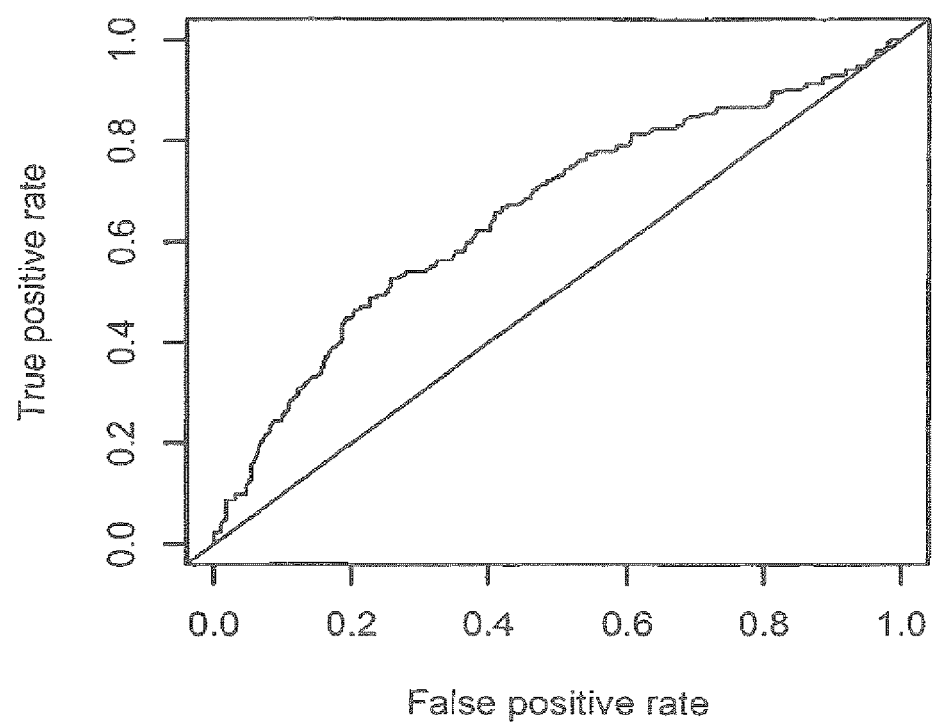

FIG. 53: ROC plot for pre-interventionally measured MR-proADM and dichotomized modified Rankin Scale after 3 months (good outcome=mRS 0-2; bad outcome=mRS 3-6). AUC=0.658.

Figure 54:
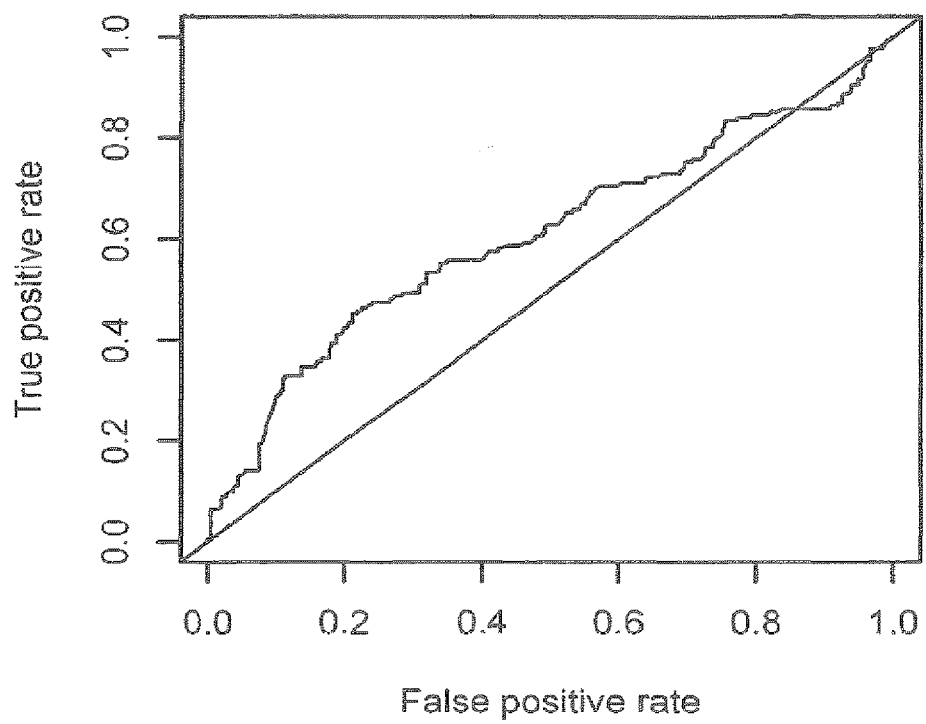

FIG. 54: ROC plot for pre-interventionally measured CT-proET-1 and dichotomized modified Rankin Scale after 3 months (good outcome=mRS 0-2; bad outcome=mRS 3-6). AUC=0.608.

Figure 55:
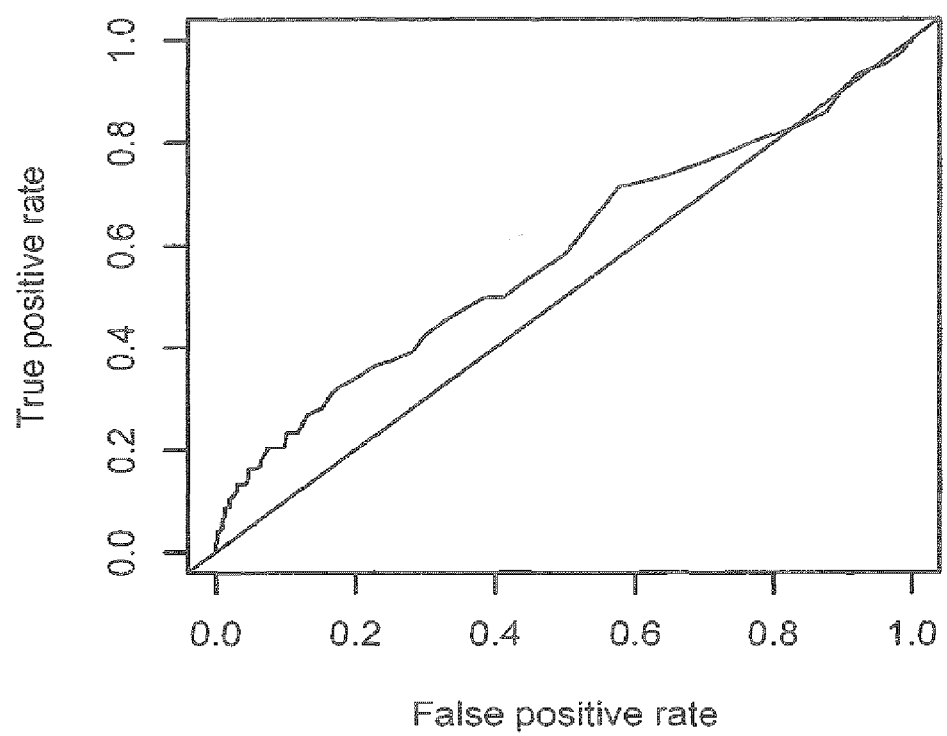

FIG. 55: ROC plot for pre-interventionally measured PCT and dichotomized modified Rankin Scale after 3 months (good outcome=mRS 0-2; bad outcome=mRS 3-6). AUC=0.580.

Figure 56:
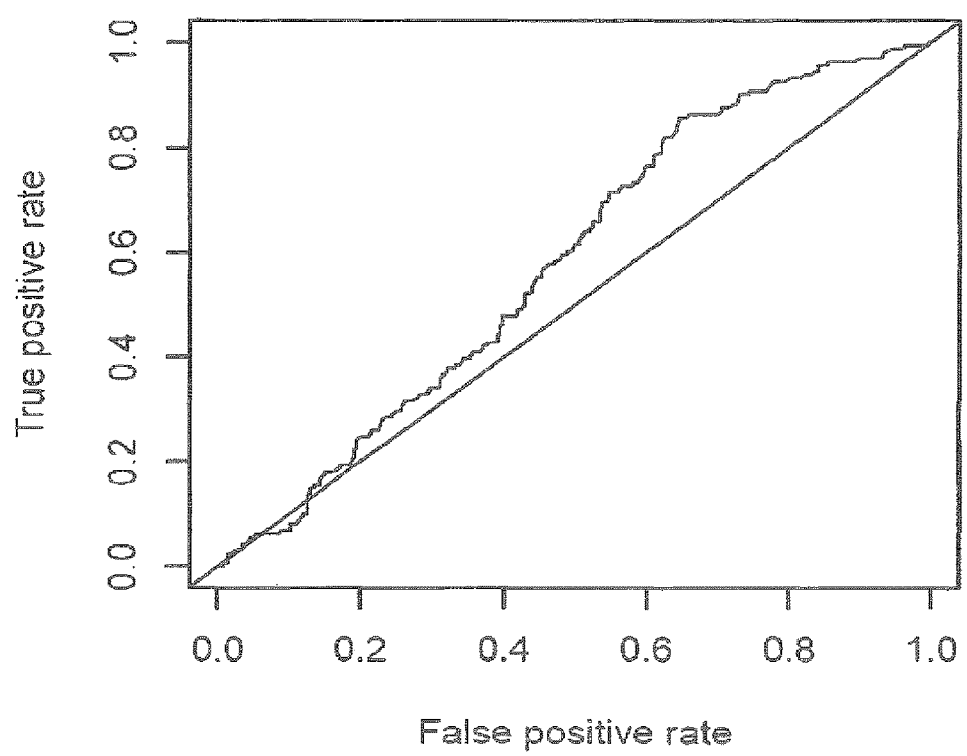

FIG. 56: ROC plot for pre-interventionally measured hGH and dichotomized modified Rankin Scale after 3 months (good outcome=mRS 0-2; bad outcome=mRS 3-6). AUC=0.581.

Figure 57:
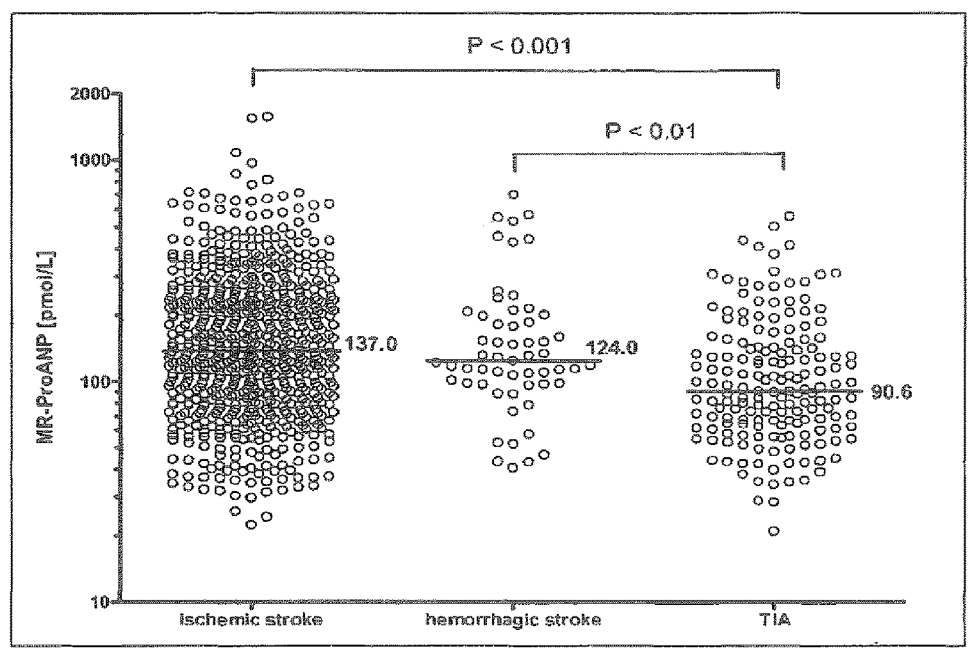

FIG. 57: Distribution of MR-proANP levels in patients with ischemic stroke, hemorrhagic stroke and TIA. Median values are 137.0 pmol/L, 124.0 pmol/L and 90.6 pmol/L, respectively.

Figure 58:
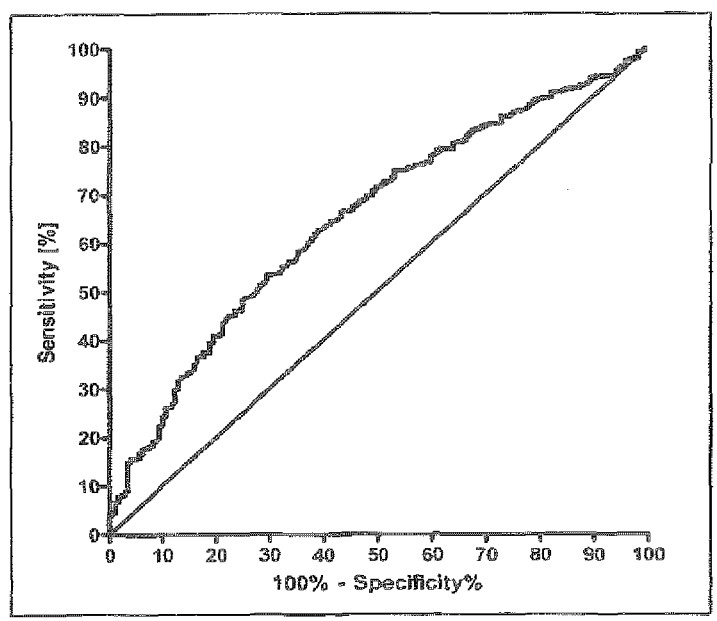

FIG. 58: ROC plot for differential diagnosis of ischemic stroke and TIA using MR-proANP as single marker. AUC=0.65 (P<0.0001).

Figure 59:
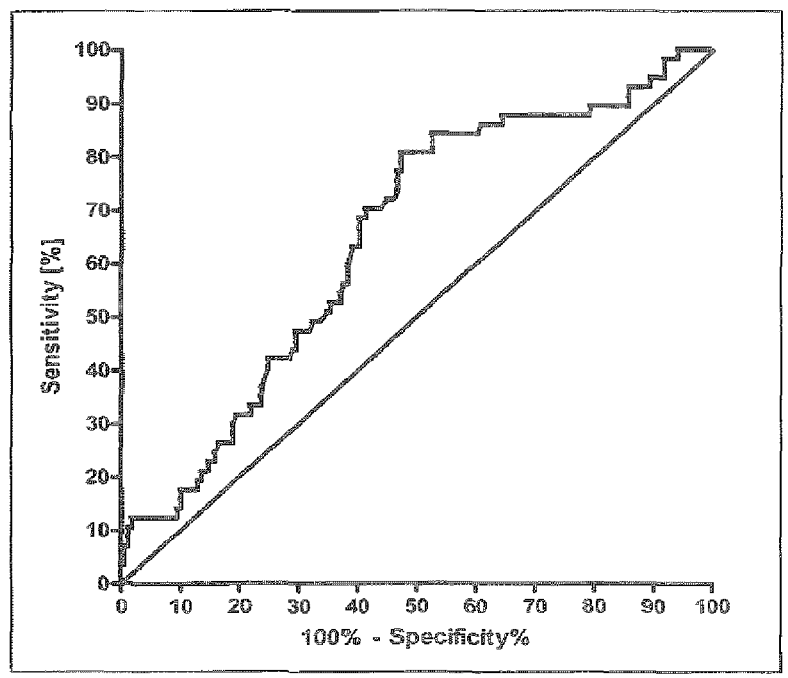

FIG. 59: ROC plot for differential diagnosis of hemorrhagic stroke and TIA using MR-proANP as single marker. AUC=0.65 (P<0.001)

Figure 60:
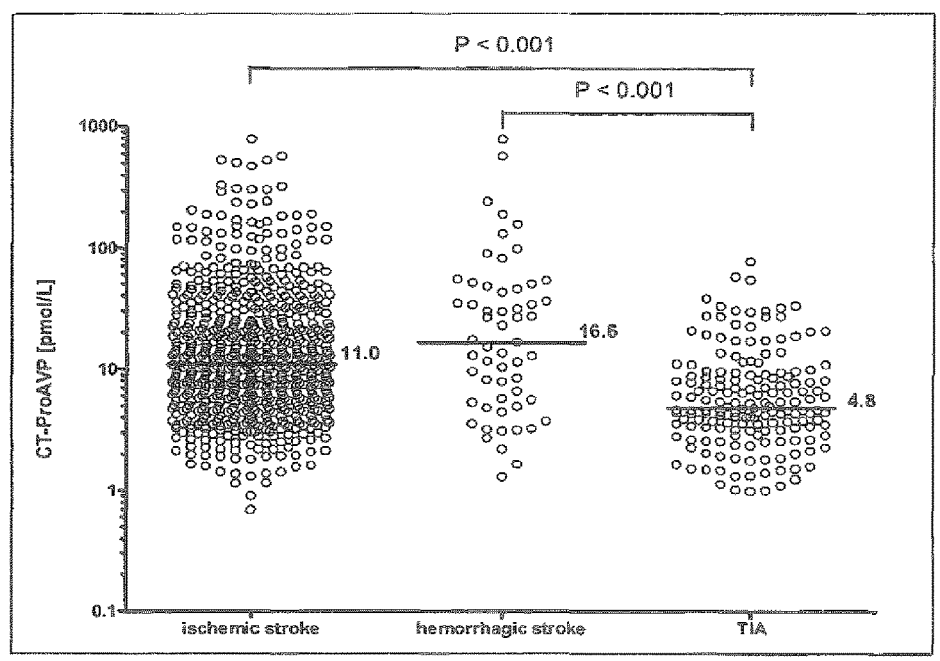

FIG. 60: Distribution of CT-proAVP (copeptin) levels in patients with ischemic stroke, hemorrhagic stroke and TIA. Median values are 11.0 pmol/L, 16.6 pmol/L and 4.8 pmol/L, respectively.

Figure 61:
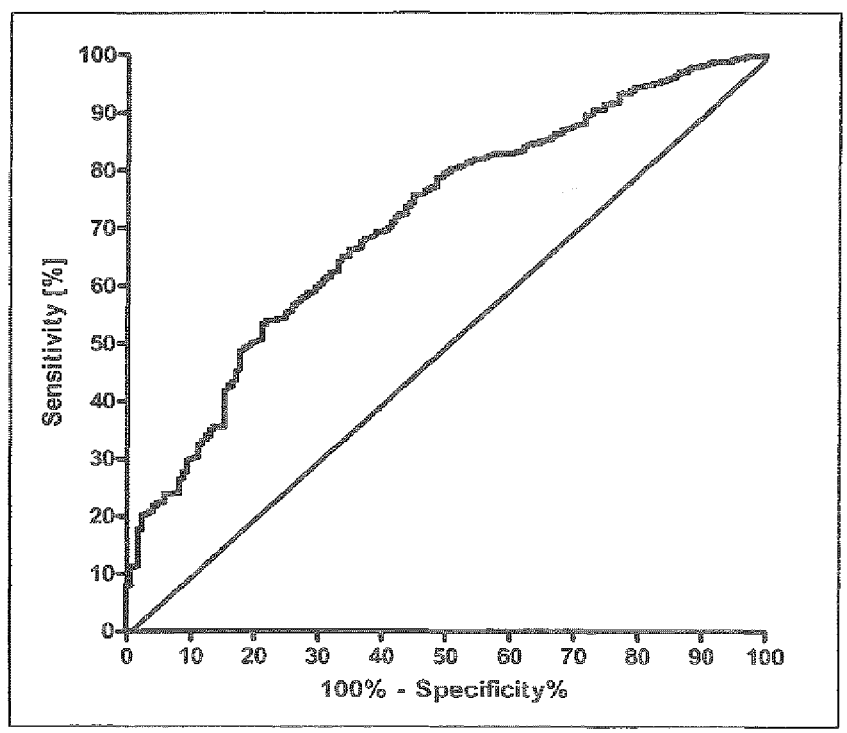

FIG. 61: ROC plot for differential diagnosis of ischemic stroke and TIA using copeptin as single marker. AUC=0.71 (P<0.0001).

Figure 62:
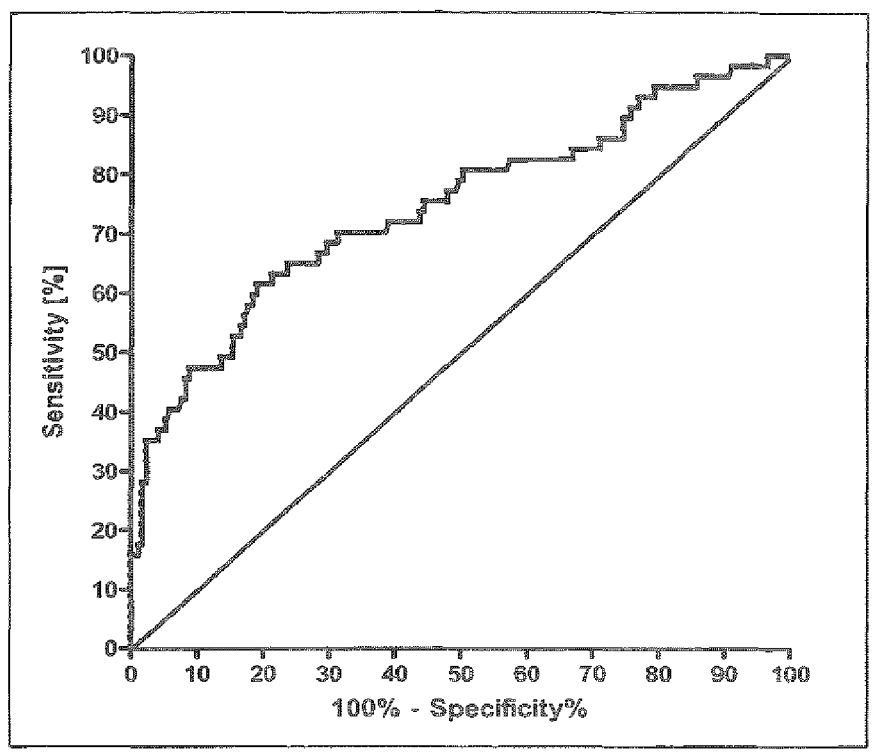

FIG. 62: ROC plot for differential diagnosis of hemorrhagic stroke and TIA using copeptin as single marker. AUC=0.74 (P<0.0001)

Figure 63:
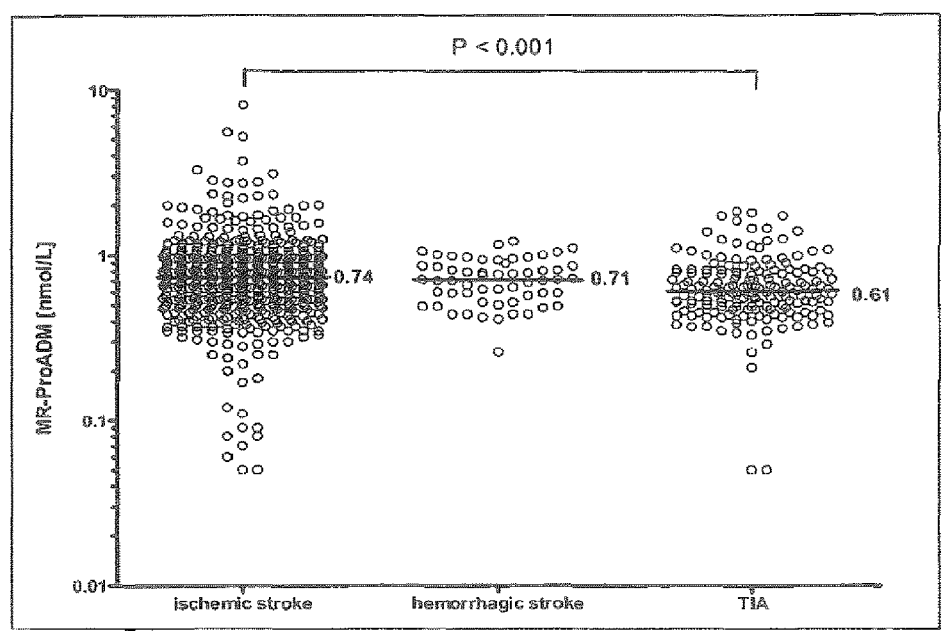

FIG. 63: Distribution of MR-proADM levels in patients with ischemic stroke, hemorrhagic stroke and TIA. Median values are 0.74 nmol/L, 0.71 nmol/L and 0.61 nmol/L, respectively.

Figure 64:
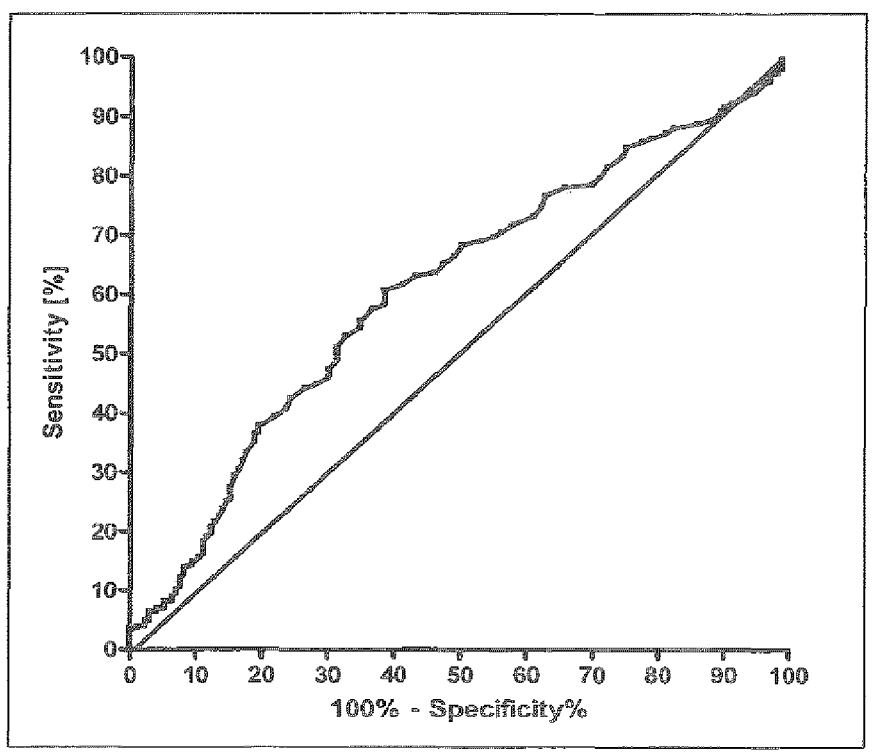

FIG. 64: ROC plot for differential diagnosis of ischemic stroke and TIA using MR-proADM as single marker. AUC=0.61 (P<0.0001).

Figure 65:
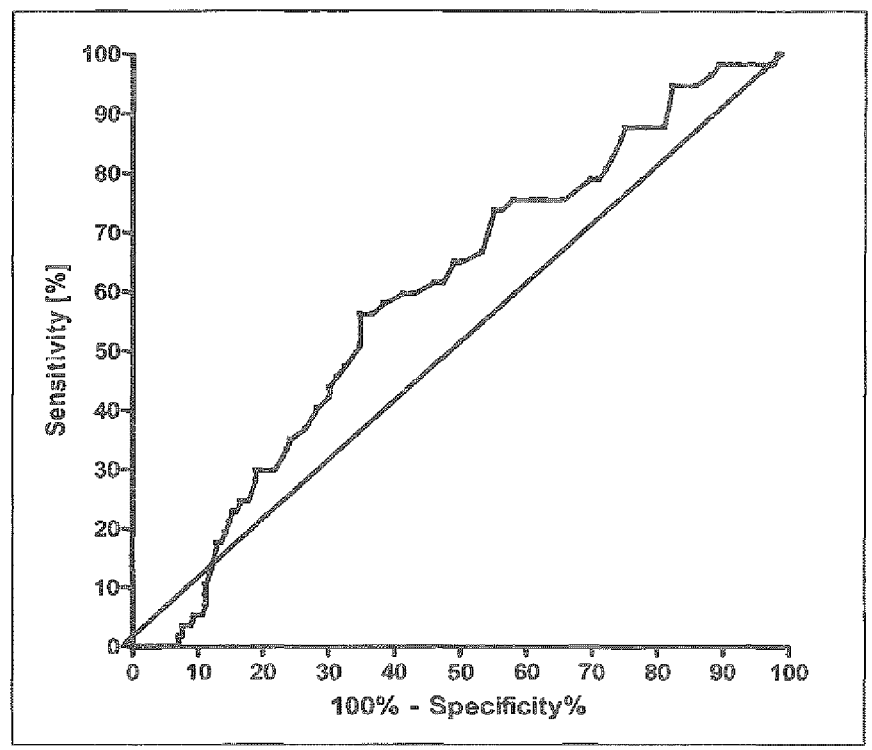

FIG. 65: ROC plot for differential diagnosis of hemorrhagic stroke and TIA using MR-proADM as single marker. AUC=0.59 (P=0.033)

Figure 66:
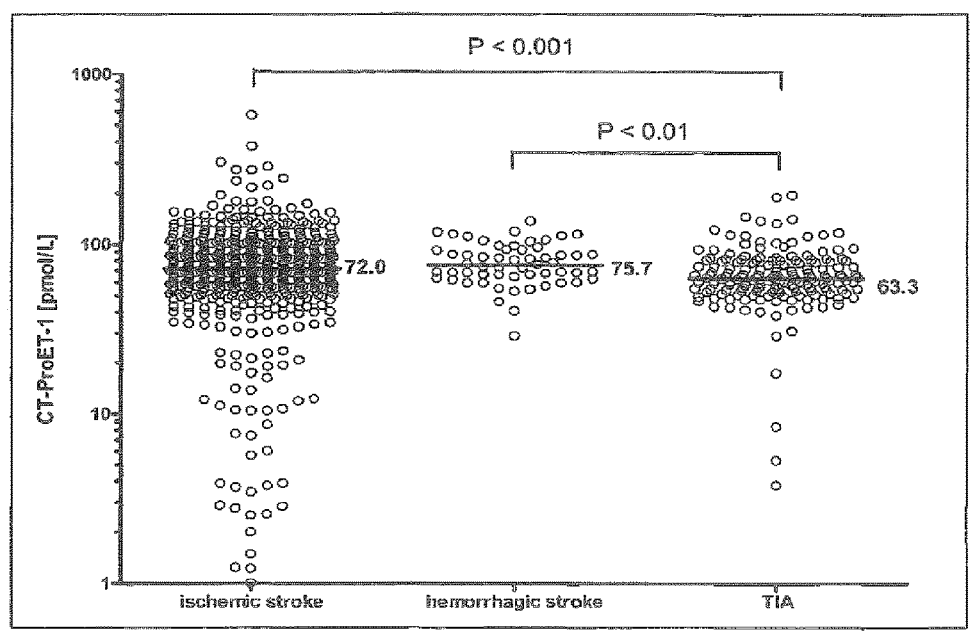

FIG. 66: Distribution of CT-proET-1 levels in patients with ischemic stroke, hemorrhagic stroke and TIA. Median values are 72.0 pmol/L, 75.7 pmol/L and 63.3 pmol/L, respectively.

Figure 67:
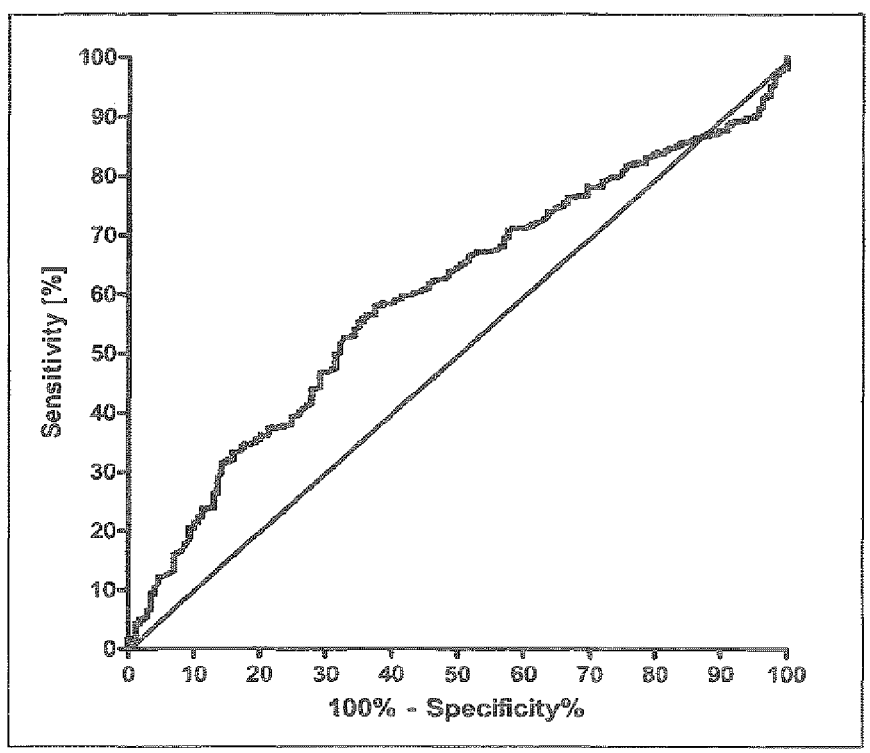

FIG. 67: ROC plot for differential diagnosis of ischemic stroke and TIA using CT-proET-1 as single marker. AUC=0.59 (P<0.001).

Figure 68:
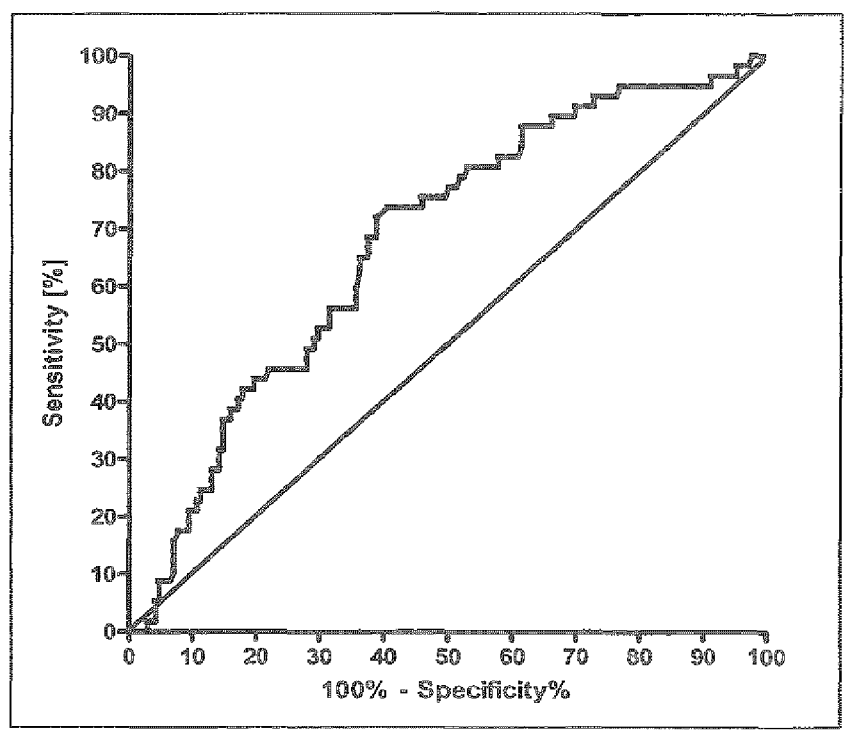

FIG. 68: ROC plot for differential diagnosis of hemorrhagic stroke and TIA using CT-proET-1 as single marker. AUC=0.68 (P<0.0001)

Figure 69:
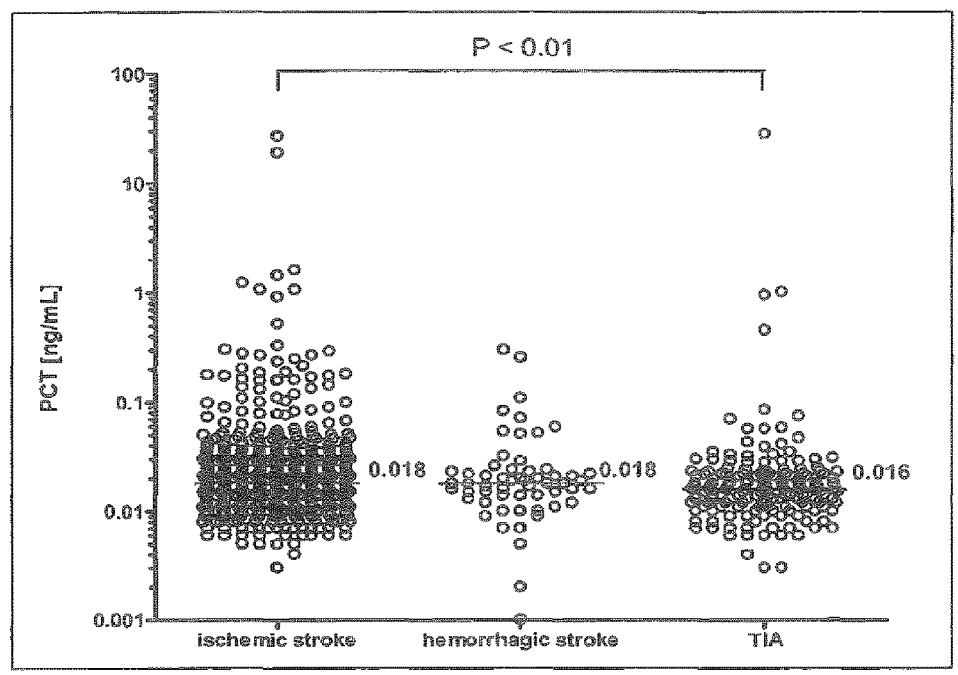

FIG. 69: Distribution of PCT levels in patients with ischemic stroke, hemorrhagic stroke and TIA. Median values are 0.018 ng/mL, 0.018 ng/mL and 0.016 ng/mL, respectively.

Figure 70:
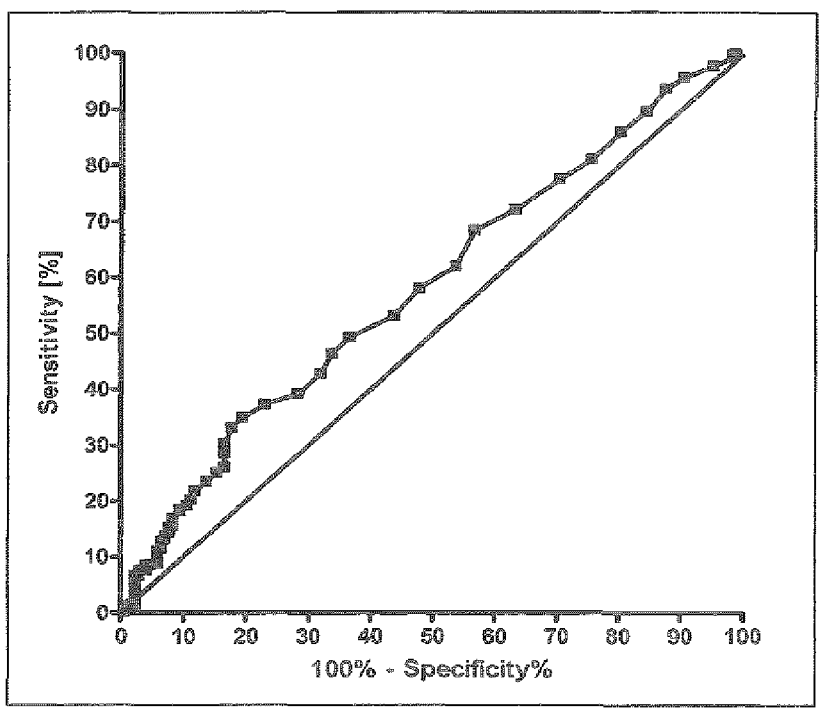

FIG. 70: ROC plot for differential diagnosis of ischemic stroke and TIA using PCT as single marker. AUC=0.58 (P<0.001).

Figure 71:
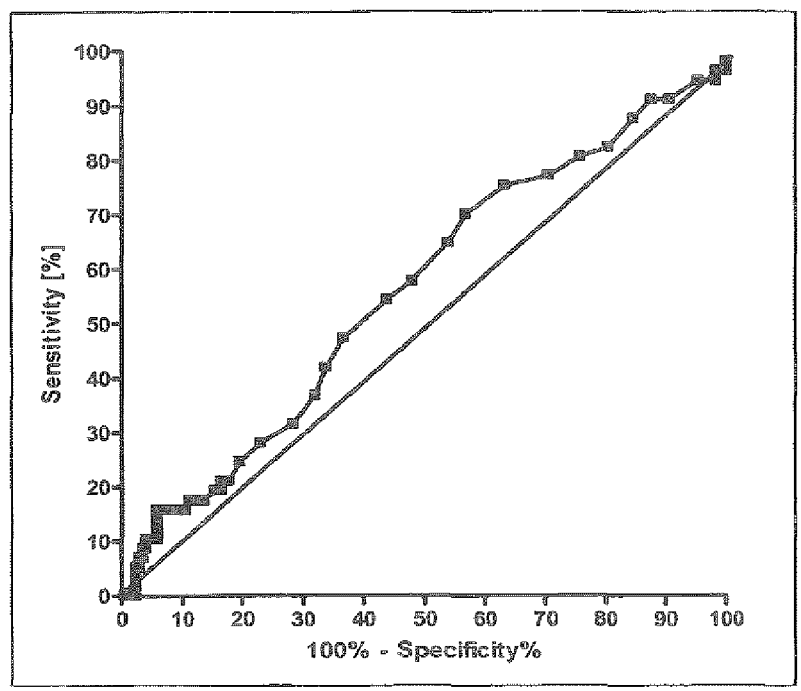

FIG. 71: ROC plot for differential diagnosis of hemorrhagic stroke and TIA using PCT as single marker. AUC=0.56 (P=0.17)

Figure 72:
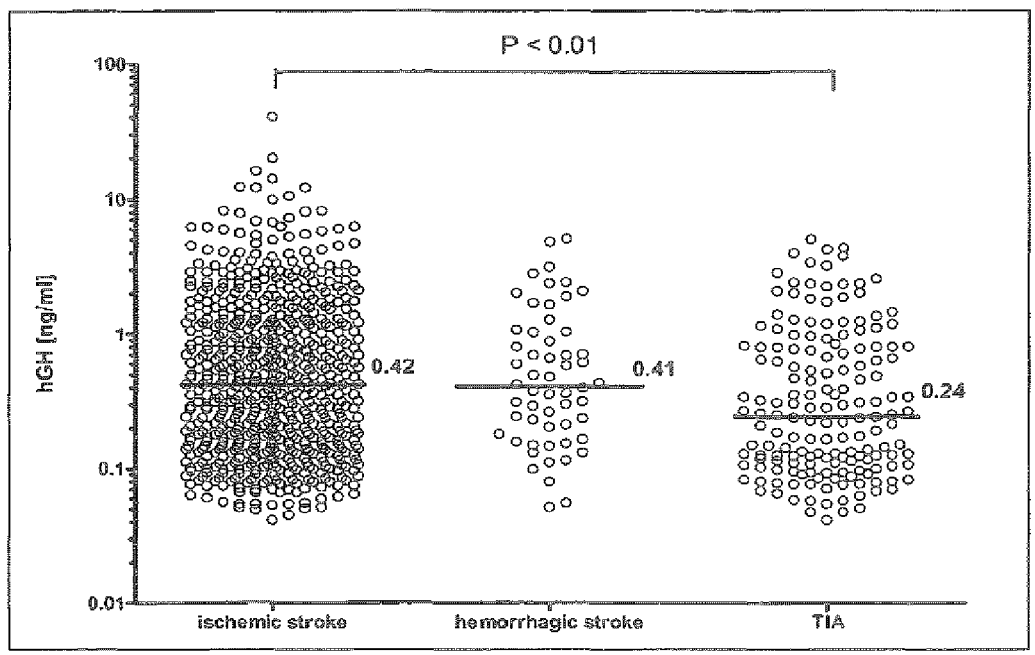

FIG. 72: Distribution of hGH levels in patients with ischemic stroke, hemorrhagic stroke and TIA. Median values are 0.42 ng/mL, 0.41 ng/mL and 0.24 ng/mL, respectively.

Figure 73:
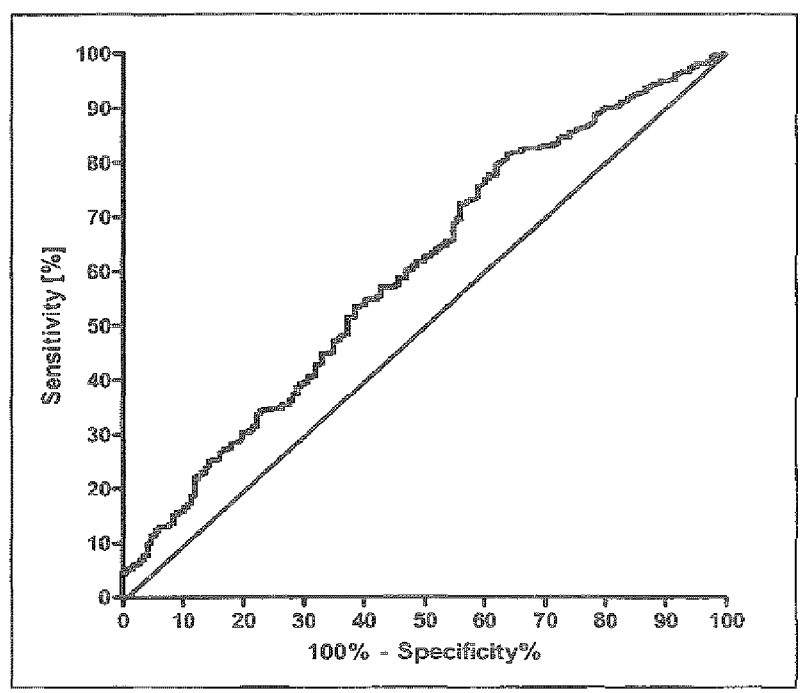

FIG. 73: ROC plot for differential diagnosis of ischemic stroke and TIA using hGH as single marker. AUC=0.60 (P<0.001).

Figure 74:
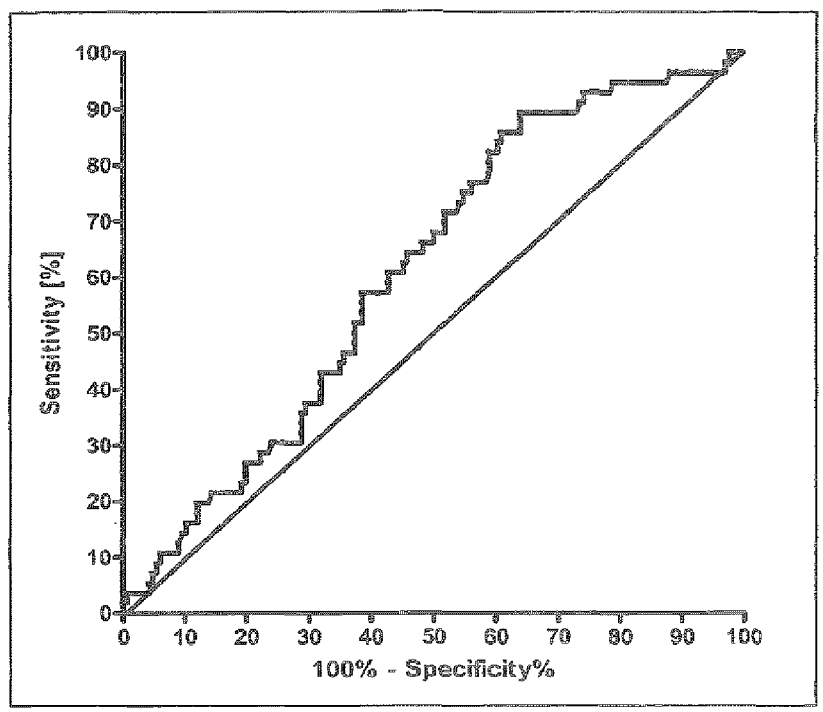

FIG. 74: ROC plot for differential diagnosis of hemorrhagic stroke and TIA using hGH as single marker. AUC=0.61 (P=0.013)

FIG. 75: SEQ ID NO:1 (amino acid sequence of pre-proADM)

FIG. 76: SEQ ID NO:2 (amino acid sequence of proADM)

FIG. 77: SEQ ID NO:3 (amino acid sequence of proADM N20)

FIG. 78: SEQ ID NO:4 (amino acid sequence of MR-proADM)

FIG. 79: SEQ ID NO:5 (amino acid sequence of ADM)

FIG. 80: SEQ ID NO:6 (amino acid sequence of pre-proANP)

FIG. 81: SEQ ID NO:7 (amino acid sequence of proANP)

FIG. 82: SEQ ID NO:8 (amino acid sequence of ANP)

FIG. 83: SEQ ID NO:9 (amino acid sequence of NT-proANP)

FIG. 84: SEQ ID NO:10 (amino acid sequence of amino acids 53-90 of proANP)

FIG. 85: SEQ ID NO:11 (amino acid sequence of pre-pro-AVP)

FIG. 86: SEQ ID NO:12 (amino acid sequence of pro-AVP)

FIG. 87: SEQ ID NO:13 (amino acid sequence of AVP)

FIG. 88: SEQ ID NO:14 (amino acid sequence of CT-pre-proAVP or Copeptin)

FIG. 89: SEQ ID NO:15 (amino acid sequence of Neurophysin II)

FIG. 90: SEQ ID NO:16 (amino acid sequence of pre-pro-ET-1)

FIG. 91: SEQ ID NO:17 (amino acid sequence of pro-ET-1)

FIG. 92: SEQ ID NO:18 (amino acid sequence of ET-1)

FIG. 93: SEQ ID NO:19 (amino acid sequence of CT-pro-ET-1)

FIG. 94: SEQ ID NO:20 (amino acid sequence of Big-ET-1)

FIG. 95: SEQ ID NO:21 (amino acid sequence of pre-pro-Calcitonin)

FIG. 96: SEQ ID NO:22 (amino acid sequence of PCT)

FIG. 97: SEQ ID NO:23 (amino acid sequence of N-terminal PCT)

FIG. 98: SEQ ID NO:24 (amino acid sequence of Calcitonin)

FIG. 99: SEQ ID NO:25 (amino acid sequence of Katacalcin)

FIG. 100: SEQ ID NO:26 (amino acid sequence of pre-pro-BNP)

FIG. 101: SEQ ID NO:27 (amino acid sequence of pro-BNP)

FIG. 102: SEQ ID NO:28 (amino acid sequence of NT-pro-BNP)

FIG. 103: SEQ ID NO:29 (amino acid sequence of BNP

EXAMPLES

Example 1: Clinical Study

Study Setting, Inclusion/Exclusion Criteria

The study was set at the emergency and neurological and neurosurgical clinic of the University Hospital of Basel. All consecutive patients who are admitted to the emergency department with an ischemic or hemorrhagic stroke or transient ischemic attack (TIA) according to the World Health Organization criteria with symptom onset within the last 3 days were included into the study. Patients without an informed consent were excluded.

Baseline Data Collection

Access to data of all eligible patients that are not included into this study is important to avoid a selection bias. Thus, baseline data and information on inclusion and exclusion criteria in all eligible patients were collected irrespective whether they are or are not included into the study. This allows the comparison of baseline data of eligible patients who consented to participate with those who did not. Baseline data collection in patients were collected by the investigators and comprised:

a) age
b) gender
c) BMI
d) Medical history items: actual history that preceded the hospitalization; ABCD score (Rothwell et al., 2005. *A simple score (ABCD) to identify individuals at high early risk of stroke after transient ischaemic attack. Lancet* 366: 29-36) in patients with transient ischemic attack; family history; relevant co-morbidities also assessed by the charlson index (Goldstein et al., 2004. *Charlson Index comorbidity adjustment for ischemic stroke outcome studies. Stroke* 35: 1941-5) (i.e. hypertension, previous stroke, previous TIA, ischemic heart disease, atrial fibrillation, diabetes mellitus, renal and liver dysfunction, congestive heart failure, dyslipidemia; comorbidities with the risk of hyponatremia (severe hypothyroidism, glucocorticoid insufficiency, neoplasm, HIV infection); smoking history (pack-years) and status (pack per day); current medication; alcohol consumption (glass and grams per day); time from onset of symptoms to admission.

e) Place of residence: i.e. independent living, defined as living at home or in an old people's home with or without support of the family circle and/or professional care (the family circle consists of the spouse and/or other important persons who live together with the patient; dependent living, defined as nursing home long-stay department, other hospital.

f) Clinical items: physical examination including neurological status, NIHSS (to assess the severity of stroke) and Glasgow Coma scale (GCS; Adams et al., 1999. *Baseline NIH Stroke Scale score strongly predicts outcome after stroke: A report of the Trial of Org* 10172 *in Acute Stroke Treatment (TOAST). Neurology* 53: 126-31), blood pressure, pulse rate, weight, volume status (including skin turgor, jugular venous distension, auscultation, if available flow sheet of fluid intake and loss), body temperature; in neurosurgical patients intracerebral pressure if performed within the routine clinical management.

g) Clinical symptoms of hyponatraemia were evaluated on admission and in case of sodium imbalance in neurological patients. In patients undergoing intracranial surgery evaluate clinical symptoms were evaluated daily. Specifically the presence of headache, anorexia, nausea, vomiting, muscle cramps and aches, seizures, confusion, apathetic or lethargic development was monitored.

h) Routine/Standard laboratory tests: routine blood sampling including: hematocrit, blood urea nitrogen, bicarbonate, total protein, albumin, uric acid serum and urine electrolytes, urine and serum osmolality, creatinine, lipids, TSH, fT4, T3, and basal cortisol. All blood sampling was done before any food intake, or smoking, if feasible. Alternatively, influencing factors were monitored.

i) Imaging: Computer tomography or MRI of the neurocranium (T1, T2, diffusion-weighted image sequence, with or without contrast), if indicated magnetic resonance angiography or conventional cerebral angiography. The time-points of contrast agent application were recorded.

Stroke patients were also classified on the basis of the vascular territory of the ischemic lesion as follows: total anterior circulation syndrome (TACS), partial anterior circulation syndrome (PACS), lacunar circulation syndrome (LACS), posterior circulation syndrome (POCS).

j) Further investigations: Stroke patients had neurosonography, echocardiography, standard 12-leaf electrocardiography and 24-hour electrocardiography and then were classified by etiology of strokes according to Trial of Org 10172 in acute Treatment (TOAST) stroke subtype classification, which differs between large artery atherosclerosis, cardio-embolism, small-artery occlusion, other etiology, and undetermined etiology.

Informed Consent Statement

The study was approved by the ethics committee of Basel (Ethikkommission beider Basel). It is important to note that this is an exploratory and observational study; the only study related intervention will be the asseveration of 7.5 ml of plasma obtained during the routinely performed blood sampling. Therefore, patients were required to provide written informed consent that they agree for the use of their data for scientific purposes. In patients, in which "informed consent" was not feasible due to sequela of the acute CNS lesion (the latter a prerequisite for inclusion), patients' next to kin could sign an assent form to state the presumptive will of the patient. In case, next of kin were not readily available, a treating physician—who must not be involved in the study—had to certify that there are no objections for inclusion in the study from his point of view. Only after these informed consent procedures the patient could be included in the study.

Management of Participants Throughout the Trial

Step 1.

All eligible patients in the emergency department or the neurological ward were included into the study.

Step 2.

All baseline data were collected.

Step 3.

During hospitalization clinical items including weight, blood pressure, pulse rate, volume status and body temperature were assessed by chart review until discharge.

Fluid treatment and drugs
Potential symptoms of hyponatremia, i.e. headache, nausea, vomiting, muscle cramps and aches, anorexia, impaired consciousness, seizure.
Routinely performed laboratory tests (chemogram, plasma glucose, serum osmolality, urine osmolality, sodium in urine, hematocrit) were sampled at the time-points upon routine blood sampling.

Step 4.

In all patients, on day 5 of the hospitalization, a clinical examination with NIHSS, Barthel Index and Rankin Scale were performed (Collin et al., 1988. *The Barthel ADL Index: a reliability study, International Disability Study* 10: 61-3; Bonita and Beaglehole, 1988. *Modification of Rankin Scale: Recovery of motor function after stroke. Stroke* 19:1497-1500).

The future place of residence (i.e. dependent vs. independent living) was assessed.

Step 6.

In patients with ischemic stroke a telephone follow-up regarding morbidity and mortality (as assessed by the Barthel Index and Rankin Scale) was obtained after 3 months. An unfavorable outcome was defined as a Barthel index <85 or modified Rankin scale of 3 to 6.

Measurement of Marker Peptide Concentrations

MR-proANP levels were measured with a chemiluminescence sandwich immunoassay with a lower detection limit of 6 pmol/L. In 325 healthy individuals the range of MR-proANP concentrations was 9.6-313 pmol/L with a median of 45 pmol/L. Concentrations differed not significantly between males and females, but significantly correlated with the age of the subjects.

MR-proADM levels were measured with a chemiluminescence sandwich immunoassay with a lower detection limit of 0.08 nmol/L. In 264 healthy individuals (117 male and 147 female) MR-proADM values followed a Gaussian distribution with mean (SD) values of 0.33 (0.07) nmol/L and a range of 0.10-0.64 nmol/L. There was no significant difference between gender, but MR-proADM concentrations significantly correlated with age.

CT-proET-1 levels were measured with a chemiluminescence sandwich immunoassay with a lower detection limit of 0.4 pmol/L. In 326 healthy individuals (150 male and 176 female) CT-proET-1 values followed a Gaussian distribution with a mean (SD) of 44.3 (10.6) pmol/L and a range of 10.5-77.4 pmol/L. Mean CT-proET-1 concentrations in males and females were not significantly different but significantly correlated with age.

CT-proAVP (Copeptin) levels were measured with a chemiluminescence sandwich immunoassay with a lower detection limit of 1.7 pmol/L. In 359 healthy individuals (153 men and 206 women), median CT-proAVP levels were 4.2 pmol/L ranging from 1.0-13.8 pmol/L. Median concentrations of CT-proAVP differed significantly between male and female. There was no correlation between CT-proAVP levels and age.

PCT levels were measured with the chemiluminescence sandwich immunoassay "PCT sensitive" (B.R.A.H.M.S, Hennigsdorf, Germany) with a lower detection limit of 7 pg/ml. In 500 healthy individuals, the median was 13.5 pg/ml (range <7 to 63 pg/ml). There were no significant differences in the range and median PCT values between males and females or among age groups.

Human growth hormone was measured with a newly developed chemiluminescence sandwich immunoassay for the specific detection of the most abundant 22 kDa hGH isoform. The median concentration of the 22 kDa hGH isoform in a cohort of 50 blood donors was 0.19 ng/ml (range 0.05-8.82 ng/ml).

The plasma levels of the marker peptides MR-proANP, MR-proADM, CT-proET-1, CT-proAVP (Copeptin), PCT and hGH have been determined in 352 patients with ischemic stroke, in 32 patients with cerebral hemorrhage and in 102 patients with TIA. Blood samples were taken at the day of hospitalization (day 0) and 1, 3 and 5 days after hospitalization.

Examples 2 to 11

Examples 2 to 11 concern the same group of patients and are based on the study of example 1. Tables 1 and 2 summarize the patients of the study and their outcome. Blood samples (EDTA treated plasma samples) were taken from a group of 501 stroke or TIA patients. The group of patients is the same as in example 1, however, the number may slightly differ, since not for all days all patients were available and not on all days enough sample volume was available for every patient to determine all markers.

Example 2: Prognosis of Survival (Death within 3 Months) with Markers Measured on Day 0

The outcome for patients with stroke or TIA within 3 (4) months after the stroke or TIA is investigated and correlated to the level of the markers MR-proANP, MR-proADM, CT-proAVP, CT-proET1 and PCT in samples of said patients. Samples have been taken on day 0 (day of hospitalization). From this correlation hazard ratios (HR) have been calculated for the given cut-off values (threshold values). The cut-off values have been determined by maximizing the sum of sensitivity and specificity as determined from time-dependent ROC analysis.

Tables 3a to 4 summarize the HR values for the different markers and their combinations. FIGS. 1 to 27 show the Kaplan-Meier plots (proportion of patients surviving within four months) for the different markers/marker combinations and in combination with Rankin/Barthels Index/NIHSS.

TABLE 1

Summary of patients

| definite diagnosis | frequency | percentage |
|---|---|---|
| hemorrhagic stroke | 32 | 6.4 |
| ischemic stroke | 362 | 72.3 |
| TIA | 107 | 21.4 |
| sum | 501 | 100.0 |

TABLE 2

Survival of patients

| dead within 3 months | frequency | percentage |
|---|---|---|
| yes | 53 | 10.6 |
| no | 447 | 89.2 |
| unknown | 1 | 0.2 |
| sum | 501 | 100.0 |

TABLE 3a

Hazard ratios (HR) for different markers

| Marker | HR | cut off |
|---|---|---|
| MR-proANP | 10.8 | 188 |
| CT-proAVP | 9.4 | 20.257 |
| MR-proADM | 4.7 | 0.666 |
| CT-proET-1 | 4.1 | 98.3 |
| PCT sens | 3.4 | 0.026 |
| hGH | 1.4 | 0.34 |

TABLE 3b

Hazard ratios (HR) for different marker combinations

| Marker combination | HR (both high vs both low) |
|---|---|
| MR-proANP + CT-proAVP | 61.4 |
| MR-proANP + MR-proADM | 62.7 |
| MR-proANP + CT-proET-1 | 17.6 |
| MR-proANP + PCT sens | 25.2 |
| CT-proAVP + MR-proADM | 37.9 |
| CT-proAVP + CT-proET-1 | 13.2 |
| CT-proAVP + PCT sens | 25.3 |
| MR-proADM + CT-proET-1 | 8.7 |
| MR-proADM + PCT sens | 11.4 |
| CT-proET-1 + PCT sens | 6.8 |
| HGH + MR-proANP | 12.3 |
| HGH + MR-proADM | 5.8 |
| HGH + CT-proET-1 | 5.0 |
| HGH + PCT sens | 4.4 |

TABLE 3c

Hazard ratios (HR) for combination of all six markers

| Marker combinations | HR (>3 high vs all low) |
|---|---|
| Combination of 6, model 1 | >100 |
| Combination of 6, model 2 | >100 |

TABLE 4

Hazard ratios (HR) of different markers in combination with different scores

| Marker | HR complete | HR mRS, day 5 = 5 | HR Barthel, day 5 <85% | HR NIHSS, day 1 >10 | HR NIHSS, day 5 >10 |
|---|---|---|---|---|---|
| MR-proANP | 10.8 | 22.4 | 31.1 | 7.8 | >100 |
| CT-proAVP | 9.4 | 1.8 | 3.5 | 2.9 | 3.0 |
| MR-proADM | 4.7 | 2.3 | 1.4 | 3.0 | 3.2 |
| CT-proET-1 | 4.1 | 2.4 | 2.1 | 3.2 | 3.2 |
| PCT sens | 3.4 | 2.5 | 2.5 | 4.3 | 6.8 |

Example 3: Prognosis of Survival (Death within 3 Months) with Markers Measured on Day 0 and Day 5 (Days 0 and 5 in Combination)

TABLE 5

Hazard ratios (HR) for different markers

| Marker, day 0 and day 5 | HR (day 0 only) | HR (both high vs both low) | cut off |
|---|---|---|---|
| MR-proANP | 10.8 | 26.5 | 188 |
| CT-proAVP | 9.4 | 24.2 | 20.257 |
| MR-proADM | 4.7 | 6.6 | 0.666 |
| CT-proET-1 | 4.1 | 8.7 | 98.3 |
| PCT sens | 3.4 | 7.8 | 0.026 |
| hGH | 1.4 | 1.4 | 0.34 |

Table 5 summarizes the HR values for the different markers in samples taken on day 0 and 5. FIGS. 28 to 32 show the Kaplan-Meier plots (proportion of patients surviving within four months) for the different markers.

Example 4: Prognosis of Survival (Death within 3 Months) with Markers Measured on Day 5 and in Combination with the NIHSS

TABLE 6

Hazard ratios (HR) for different markers

| Marker, day 5 and NIHSS (>10) | HR (day 5 only) | HR (both high vs both low) | cut off |
|---|---|---|---|
| NIHSS | 7.3 | — | 10 |
| MR-proANP | 8.0 | 44.6 | 188 |
| CT-proAVP | 18.3 | 43.4 | 20.257 |
| MR-proADM | 2.8 | 14.6 | 0.666 |
| CT-proET-1 | 7.9 | 48.4 | 98.3 |
| PCT sens | 4.1 | 17.7 | 0.026 |
| hGH | 1.4 | 6.6 | 0.34 |

Table 6 summarizes the HR values for the different markers in samples taken on day 5 and in combination with the NIHSS values for said patients. FIGS. 33 to 39 show the Kaplan-Meier plots (proportion of patients surviving within four months) for NIHSS alone and for the different markers in combination with NIHSS based on samples taken on day 5.

Example 5: Prognosis of Survival (Death within 3 Months) with Markers Measured on Day 5 and in Combination with the Barthel Index

TABLE 7

Hazard ratios (HR) for different markers

| Marker, day 5 and Barthel Index (<85%) | HR (day 5 only) | HR (both high vs both low) | cut off |
|---|---|---|---|
| Barthel Index | 12.3 | — | 85% |
| MR-proANP | 8.0 | 44.0 | 188 |
| CT-proAVP | 18.3 | >100 | 20.257 |
| MR-proADM | 2.8 | 14.6 | 0.666 |
| CT-proET-1 | 7.9 | 68.5 | 98.3 |
| PCT sens | 4.1 | 24.4 | 0.026 |
| hGH | 1.4 | 7.2 | 0.34 |

Table 7 summarizes the HR values for the different markers in samples taken on day 5 and in combination with Barthel Index values for said patients. FIGS. 40 to 43 show the Kaplan-Meier plots (proportion of patients surviving within four months) for Barthel Index for the different markers in combination with Barthel Index based on samples taken on day 5.

Example 6: Prognosis of Survival with Markers Measured on Day 5 and in Combination with the Modified Rankin Scale, Outcome "Dead within 3 Months"

TABLE 8

Hazard ratios (HR) for different markers

| Marker, day 5 and Rankin (>2) | HR (day 5 only) | HR (both high vs both low) | cut off |
|---|---|---|---|
| Rankin | 10.7 | — | 0-2 vs. 3-6 |
| MR-proANP | 8.0 | 37.1 | 188 |
| CT-proAVP | 18.3 | >100 | 20.257 |
| MR-proADM | 2.8 | 12.9 | 0.666 |
| CT-proET-1 | 7.9 | 49.6 | 98.3 |
| PCT sens | 4.1 | 20.4 | 0.026 |
| hGH | 1.4 | 5.7 | 0.34 |

Table 8 summarizes the HR values for the different markers in samples taken on day 5 and in combination with the modified Rankin Scale values for said patients. FIGS. 44 to 49 show the Kaplan-Meier plots (proportion of patients surviving within four months) for the modified Rankin Scale alone and for the different markers in combination with the modified Rankin Scale based on samples taken on day 5.

Example 7: Prognosis of "Re-Stroke/Re-TIA" (within 3 Months) with Markers Measured on Day 0

Table 9 summarizes the re-occurrence of strokes (re-stroke) and TIAs (re-TIA) in the group of patients. Tables 10 to 14 summarize the calculated HR values for the different markers and marker combinations.

TABLE 9 re-stroke or re-TIA within 3 months

| re-event within 3 months | frequency | percentage |
|---|---|---|
| no | 419 | 83.6 |
| yes | 29 | 5.8 |
| unknown | 53 | 10.6 |
| sum | 501 | 100.0 |

TABLE 10

Odd ratios (OR) for different markers

| Marker | OR | OR (TIA only) | cut off |
|---|---|---|---|
| MR-proANP | 3.6 | 21.7 | 323.2 |
| CT-proAVP | 3.0 | >100 | 38.6 |
| MR-proADM | 3.7 | 4.2 | 1.18 |
| CT-proET-1 | — | 7.0 | 59.2 |
| PCT sens | 2.9 | 3.2 | 0.057 |
| hGH | — | 1.9 | 0.34 |

TABLE 11

Odd ratios for different marker combinations

| Marker (combination) | OR (both high vs both low) | OR (both high vs both low) TIA only |
|---|---|---|
| MR-proANP + CT-proAVP | 7.4 | >100 |
| MR-proANP + MR-proADM | 8.1 | >100 |
| MR-proANP + CT-proET-1 | — | 76.0 |
| MR-proANP + PCT sens | 4.5* | 24.0* |
| CT-proAVP + MR-proADM | 10.5 | >100 |
| CT-proAVP + CT-proET-1 | — | >100 |
| CT-proAVP + PCT sens | 3.5* | >100* |
| MR-proADM + CT-proET-1 | — | 15.2 |
| MR-proADM + PCT sens | 5.1* | — |
| CT-proET-1 + PCT sens | — | 18.5 |
| hGH + MR-proADM | — | 4.9 |

*not enough patients in the group "both high" to allow for calculation of OR; however, an OR is given for "both low" vs. "high in first marker".

Table 13a to 13e: Calculation of Odd Ratios for all Patients (Re-Stroke and Re-TIA)

TABLE 13a

Calculation of OR for MR-proANP

| Marker | | Re-Stroke or Re-TIA | | |
|---|---|---|---|---|
| | | no | yes | sum |
| MR-proANP | <cut off | 360 | 20 | 380 |
| | >cut off | 35 | 7 | 42 |
| | sum | 395 | 27 | 422 |
| Odds Ratio | 3.6 | | | |

TABLE 13b

Calculation of OR for CT-proAVP

| Marker | | Re-Stroke or Re-TIA | | |
|---|---|---|---|---|
| | | no | yes | sum |
| CT-proAVP | <cut off | 346 | 19 | 365 |
| | >cut off | 48 | 8 | 56 |
| | sum | 394 | 27 | 421 |
| Odds Ratio | 3.0 | | | |

TABLE 13c

Calculation of OR for MR-proADM

| Marker | | Re-Stroke or Re-TIA | | |
|---|---|---|---|---|
| | | no | yes | sum |
| MR-proADM | <cut off | 372 | 22 | 394 |
| | >cut off | 23 | 5 | 28 |
| | sum | 395 | 27 | 422 |
| Odds Ratio | 3.7 | | | |

TABLE 13d

Calculation of OR for combination of MR-proANP and CT-proAVP

| Marker model | | Re-Stroke or Re-TIA | | |
|---|---|---|---|---|
| | | no | yes | sum |
| MR-proANP + CT-proAVP | both low | 325 | 17 | 342 |
| | both high | 13 | 5 | 18 |
| | sum | 338 | 22 | 360 |
| Odds Ratio | 7.4 | | | |
| MR-proANP + MR-proADM | both low | 346 | 19 | 365 |
| | both high | 9 | 4 | 13 |
| | sum | 355 | 23 | 378 |
| Odds Ratio | 8.1 | | | |

TABLE 13e

Calculation of OR for combination of CT-proAVP and MR-proADM

| Marker model | | Re-Stroke or Re-TIA | | |
|---|---|---|---|---|
| | | no | yes | sum |
| CT-proAVP + MR-proADM | both low | 331 | 18 | 349 |
| | both high | 7 | 4 | 11 |
| | sum | 338 | 22 | 360 |
| Odds Ratio | 10.5 | | | |

Table 14a to 14d: Calculation of Odd Ratios for TIA Patients (Re-Stroke and Re-TIA)

TABLE 14a

Calculation of OR for MR-proANP

| Marker | | Re-Stroke or Re-TIA | | |
|---|---|---|---|---|
| | | no | yes | sum |
| MR-proANP | <cut off | 87 | 8 | 95 |
| | >cut off | 1 | 2 | 3 |
| | sum | 88 | 10 | 98 |
| Odds Ratio | 21.8 | | | |

TABLE 14b

Calculation of OR for CT-proAVP

| Marker | | Re-Stroke or Re-TIA | | |
|---|---|---|---|---|
| | | no | yes | sum |
| CT-proAVP | <cut off | 88 | 8 | 96 |
| | >cut off | 0 | 2 | 2 |
| | sum | 88 | 10 | 98 |
| Odds Ratio | >100 | | | |

TABLE 14c

Calculation of OR for MR-proADM

| Marker | | Re-Stroke or Re-TIA | | |
|---|---|---|---|---|
| | | no | yes | sum |
| MR-proADM | <cut off | 83 | 8 | 91 |
| | >cut off | 5 | 2 | 7 |
| | sum | 88 | 10 | 98 |
| Odds Ratio | 4.2 | | | |

TABLE 14d

Calculation of OR for CT-proET1

| Marker | | Re-Stroke or Re-TIA | | |
|---|---|---|---|---|
| | | no | yes | sum |
| CT-proET1 | <cut off | 38 | 1 | 39 |
| | >cut off | 49 | 9 | 58 |
| | sum | 87 | 10 | 97 |
| Odds Ratio | 7.0 | | | |

TABLE 14e

Calculation of OR for combination of MR-proANP and CT-proAVP

| Marker model | | Re-Stroke or Re-TIA | | |
|---|---|---|---|---|
| | | no | yes | sum |
| MR-proANP + CT-proAVP | both low | 87 | 7 | 94 |
| | both high | 0 | 1 | 1 |
| | sum | 87 | 8 | 95 |
| Odds Ratio | >100 | | | |

TABLE 14f

Calculation of OR for combination of CT-proET1 and CT-proAVP

| Marker model | | Re-Stroke or Re-TIA | | |
|---|---|---|---|---|
| | | no | yes | sum |
| CT-proET1 | both low | 38 | 1 | 39 |
| CT-proAVP | both high | 0 | 2 | 2 |
| | sum | 38 | 3 | 41 |

TABLE 14g

Calculation of OR for combination of MR-proANP and MR-proADM

| Marker model | | Re-Stroke or Re-TIA | | |
|---|---|---|---|---|
| | | no | yes | sum |
| MR-proANP | both low | 82 | 8 | 90 |
| MR-proADM | both high | 0 | 2 | 2 |
| Odds Ratio | sum | 82 | 10 | 92 |
| >100 | | | | |

Example 8: Prognosis of "Re-Stroke/Re-TIA (within 3 Months) with Markers Measured on Day 0 and in Combination with Day 5

Tables 15 to 16d summarize the results of a ROC analysis (monitoring), particularly the odds ratios, for different markers/Marker combinations.

TABLE 15

Calculation of OR for different markers

| Marker, day 0 and day 5 | OR (only day 0) | OR (both high vs both low) | cut off |
|---|---|---|---|
| MR-proANP | 3.6 | 5.1 | 323.2 |
| CT-proAVP | 3.0 | 8.5 | 38.6 |
| MR-proADM | 3.7 | 4.8 | 1.18 |
| CT-proET-1 | — | — | 59.2 |
| PCT sens | 2.9 | 4.2 | 0.057 |
| hGH | — | 4.2 | 0.34 |

Table 16a to d: Calculation of OR for single markers, day 0 and day 5:

TABLE 16a

Calculation of OR for MR-proANP

| MR-proANP | | Re-Stroke or Re-TIA | | |
|---|---|---|---|---|
| | | no | yes | sum |
| day 0, day 5 | both low | 241 | 14 | 255 |
| | both high | 17 | 5 | 22 |
| Odds Ratio | sum | 258 | 19 | 277 |
| 5.1 | | | | |

TABLE 16b

Calculation of OR for CT-proAVP

| CT-proAVP | | Re-Stroke or Re-TIA | | |
|---|---|---|---|---|
| | | no | yes | sum |
| day 0, day 5 | both low | 220 | 13 | 233 |
| | both high | 4 | 2 | 6 |
| Odds Ratio | sum | 224 | 15 | 239 |
| 8.5 | | | | |

TABLE 16c

Calculation of OR for MR-proADM

| MR-proADM | | Re-Stroke or Re-TIA | | |
|---|---|---|---|---|
| | | no | yes | sum |
| day 0, day 5 | both low | 241 | 15 | 256 |
| | both high | 10 | 3 | 13 |
| Odds Ratio | sum | 251 | 18 | 269 |
| 4.8 | | | | |

TABLE 16d

Calculation of OR for PCT

| PCT | | Re-Stroke or Re-TIA | | |
|---|---|---|---|---|
| | | no | yes | sum |
| day 0, day 5 | both low | 235 | 16 | 251 |
| | both high | 7 | 2 | 9 |
| Odds Ratio | sum | 242 | 18 | 260 |
| 4.2 | | | | |

Example 9: Prognosis of Functional Outcome (mRS, after 3 Months) with Markers Measured on Day 0

Table 17 summarizes the outcome for the group of patients in terms of the modified Rankin Scale (0 to 6). Table 18 lists the Kruskal-Wallis Chi$^2$ statistic and p value for the correlation of the different markers with the modified Rankin Scale. Table 19 summarizes the outcome in two classes: Patients with a good outcome (Rankin 0-2) and patients with a bad outcome (Rankin 3-6). Tables 20a to 20dc summarize the OR on day 0 of the markers/marker combinations for patients with good or bad outcome after 3 months]. Tables 21a to 21h summarize the calculated odds ratios (OR) for the different markers/marker combinations. FIG. 50 illustrates the correlation between Rankin and level of CT-proAVP (A) and MRproANP (B), respectively, in a box plot. FIGS. 51 to 56 illustrates the ROC plots for the different markers.

TABLE 17

Frequency distribution for the outcome (measured with the modified Rankin Scale) of Stroke/TIA patients after 3 months

| Rankin after 3 months | frequency | percentage |
| --- | --- | --- |
| 0 | 155 | 30.9 |
| 1 | 106 | 21.2 |
| 2 | 53 | 10.6 |
| 3 | 55 | 11.0 |
| 4 | 56 | 11.2 |
| 5 | 20 | 4.0 |
| 6 | 53 | 10.6 |
| unknown | 3 | 0.6 |
| sum | 501 | 100.0 |

TABLE 18

Results for different markers

| | Ranking 3 months (0-6) | |
| --- | --- | --- |
| | Chi$^2$ | p-value |
| MR-proANP | 80.4 | <0.0001 |
| CT-proAVP | 87.2 | <0.0001 |
| MR-proADM | 40.5 | <0.0001 |
| CT-proET-1 | 26.0 | 0.0005 |
| PCT sens | 22.2 | 0.0024 |

TABLE 19

Rankin after 3 months

| Rankin after 3 months | frequency | percentage |
| --- | --- | --- |
| Rankin 0-2 ("good") | 314 | 62.7 |
| Rankin 3-6 ("bad") | 184 | 36.7 |
| unknown | 3 | 0.6 |
| sum | 501 | 100.0 |

TABLE 20a

OR for different markers

| Marker | OR | cut off |
| --- | --- | --- |
| MR-proANP | 4.5 | 188 |
| CT-proAVP | 5.1 | 20.257 |
| MR-proADM | 2.8 | 0.666 |
| CT-proET-1 | 3.6 | 98.3 |
| PCT sens | 2.1 | 0.026 |
| hGH | 1.5 | 0.34 |

TABLE 20b

OR for different marker combinations

| Marker (combinations) | OR (both high vs both low) |
| --- | --- |
| MR-proANP + CT-proAVP | 15.6 |
| MR-proANP + MR-proADM | 7.3 |
| MR-proANP + CT-proET-1 | 7.6 |
| MR-proANP + PCT sens | 8.2 |
| CT-proAVP + MR-proADM | 9.8 |
| CT-proAVP + CT-proET-1 | 8.5 |
| CT-proAVP + PCT sens | 7.1 |
| MR-proADM + CT-proET-1 | 5.4 |
| MR-proADM + PCT sens | 4.4 |
| CT-proET-1 + PCT sens | 4.6 |
| HGH + CT-proAVP | 5.6 |
| HGH + MR-proADM | 4.3 |
| hGH + CT-proET-1 | 4.4 |
| hGH + PCT sens | 2.7 |
| hGH + MR-proANP | 6.2 |

TABLE 20c

OR for combination of all 6 markers

| Marker (combinations) | OR (all high vs all low) |
| --- | --- |
| combination of 6 | 22.0 |

TABLE 21a

Calculation of OR for CT-proAVP

| | | Rankin | | |
| --- | --- | --- | --- | --- |
| Marker | | 0-2 | 3-6 | sum |
| CT-proAVP | <cut off | 246 | 85 | 331 |
| | >cut off | 49 | 87 | 136 |
| | sum | 295 | 172 | 467 |
| Odds Ratio | 5.1 | | | |

TABLE 21b

Calculation of OR for MR-proANP

| | | Rankin | | |
| --- | --- | --- | --- | --- |
| Marker | | 0-2 | 3-6 | sum |
| MR-proANP | <cut off | 232 | 77 | 309 |
| | >cut off | 64 | 95 | 159 |
| | sum | 296 | 172 | 468 |
| Odds Ratio | 4.5 | | | |

TABLE 21c

Calculation of OR for MR-proADM

| | | Rankin | | |
| --- | --- | --- | --- | --- |
| Marker | | 0-2 | 3-6 | sum |
| MR-proADM | <cut off | 175 | 59 | 234 |
| | >cut off | 121 | 113 | 234 |
| | sum | 296 | 172 | 468 |
| Odds Ratio | 2.8 | | | |

TABLE 21d

Calculation of OR for CT-proET-1

| Marker | | Rankin | | |
|---|---|---|---|---|
| | | 0-2 | 3-6 | sum |
| CT-proET-1 | <cut off | 263 | 121 | 384 |
| | >cut off | 30 | 49 | 79 |
| | sum | 293 | 170 | 463 |
| Odds Ratio | 3.6 | | | |

TABLE 21e

Calculation of OR for PCT

| Marker | | Rankin | | |
|---|---|---|---|---|
| | | 0-2 | 3-6 | sum |
| PCT | <cut off | 238 | 114 | 352 |
| | >cut off | 57 | 57 | 114 |
| | sum | 295 | 171 | 466 |
| Odds Ratio | 2.1 | | | |

TABLE 21f

Calculation of OR for combination of MR-proANP and CT-proAVP

| Marker Model | | Rankin | | |
|---|---|---|---|---|
| | | no | yes | sum |
| MR-proANP + | both low | 198 | 54 | 252 |
| CT-proAVP | both high | 15 | 64 | 79 |
| | sum | 213 | 118 | 331 |
| Odds Ratio | 15.6 | | | |

TABLE 21g

Calculation of OR for combination of MR-proANP and MR-proADM

| Marker Model | | Rankin | | |
|---|---|---|---|---|
| | | no | yes | sum |
| MR-proANP + | both low | 151 | 39 | 190 |
| MR-proADM | both high | 40 | 75 | 115 |
| | sum | 191 | 114 | 305 |
| Odds Ratio | 7.3 | | | |

TABLE 21h

Calculation of OR for combination of MR-proADM and CT-proAVP

| Marker Model | | Rankin | | |
|---|---|---|---|---|
| | | no | yes | sum |
| MR-proADM + | both low | 154 | 36 | 190 |
| CT-proAVP | both high | 28 | 64 | 92 |
| | sum | 182 | 100 | 282 |
| Odds Ratio | 9.8 | | | |

Example 10: Prognosis of Functional Outcome (mRS, after 3 Months) with Markers Measured on Day 0 and in Combination with Day 5

Table 22 summarizes the OR for the single markers on day 0 and in combination with day 5. Tables 23 and 24 summarize the calculated odds ratios (OR) for two different markers in correlation with Rankin values.

TABLE 22

Odd ratios for different markers

| Marker, day 0 and day 5 | OR (only day 0) | OR (both high vs both low) | cut off |
|---|---|---|---|
| MR-proANP | 4.5 | — | 188 |
| CT-proAVP | 5.1 | 6.5 | 20.257 |
| MR-proADM | 2.8 | — | 0.666 |
| CT-proET-1 | 3.6 | — | 98.3 |
| PCT sens | 2.1 | 3.3 | 0.026 |

TABLE 23

Calculation of OR for CT-proAVP, day 0 and day 5

| CT-proAVP | | Ranking | | |
|---|---|---|---|---|
| | | 0-2 | 3-6 | sum |
| day 0, day 5 | both low | 151 | 54 | 205 |
| | both high | 12 | 28 | 40 |
| | sum | 163 | 82 | 245 |
| Odds Ratio | 6.5 | | | |

TABLE 24

Calculation of OR for PCT, day 0 and day 5

| PCT | | Ranking | | |
|---|---|---|---|---|
| | | 0-2 | 3-6 | sum |
| day 0, day 5 | both low | 129 | 42 | 171 |
| | both high | 29 | 31 | 60 |
| | sum | 158 | 73 | 231 |
| Odds Ratio | 3.3 | | | |

Example 11: Differential Diagnosis of TIA, Ischemic Stroke and Hemorrhagic Stroke FIGS. 57 to 74 summarize the results for the use of MR-proANP, copeptin, MR-proADM, CT-proET-1, PCT and hGH as single markers for the differential diagnosis of TIA, ischemic stroke and hemorrhagic stroke. Marker levels have been determined as described above for day 0 and day 1. Median values have been determined for each marker and patient group (hemorrhagic stroke, ischemic stroke, TIA) and ROC curves for the differential diagnosis of hemorrhagic stroke from TIA and ischemic stroke from TIA have been created.

TABLE 25

Optimal cut-off values for the differential diagnosis of TIA from stroke (ischemic and hemorrhagic stroke, respectively) using single markers.

| Marker | Cut off TIA vs. Ischemic stroke | Cut off TIA vs. hemorrhagic stroke |
|---|---|---|
| CT-proAVP | 9.65 pmol/L | 11.35 pmol/L |
| CT-proET | 67.15 pmol/L | 66.35 pmol/L |
| hGH | 0.13 ng/ml | 0.13 ng/ml |
| MR-proADM | 0.67 nmol/L | 0.36 nmol/L |
| MR-proANP | 130.5 pmol/L | 96.1 pmol/L |
| PCT | 0.0235 ng/mL | 0.0235 ng/mL |

The invention claimed is:

1. A method for diagnosing and treating a stroke or a transient ischemic attack in a patient suspected of having a stroke or a transient ischemic attack within 5 days to a year after said patient has previously suffered a stroke or transient ischemic attack, said method comprising:
   a. obtaining a sample of bodily fluid from said patient,
   b. detecting and quantitating in said sample from said patient the level of at least one cardiovascular peptide, wherein said cardiovascular peptide is selected from the group consisting of MR-proANP (mid-regional fragment of proANP), CT-proAVP (C-terminal fragment of arginine vasopressin precursor proAVP), MR-proADM (mid-regional fragment of adrenomedullin), CT-proET-1 (C-terminal fragment of endothelin-1 precursor pro-ET-1), PCT (calcitonin precursor procalcitonin), and hGH (human growth hormone),
   wherein said detection and quantitation comprises contacting the sample with a diagnostic assay reagent comprising a capture probe that specifically binds to said cardiovascular peptide, and detecting and quantitating the thus-formed complexes of said capture probe and cardiovascular peptide, and c. diagnosing said patient as having had a stroke or a transient ischemic attack by comparing the level of the cardiovascular peptide in the patient to a threshold level, wherein a level value of the cardiovascular peptide below the threshold is indicative for transient ischemic attack and a level value of the cardiovascular peptide above the threshold is indicative for stroke, and wherein the threshold level for MR-proANP is from about 90 to about 140 pmol/l, the threshold level for CT-proAVP is from about 9.5 to about 11.5 pmol/l, the threshold level for MR-proADM is from about 0.5 to about 0.8 nmol/l, the threshold level for CT-pro-ET-1 is from about 65 to about 90 pmol/l, the threshold level for PCT is from about 0.0230 to about 0.0260 ng/ml, and the threshold level for hGH is from about 0.10 to about 0.3 ng/ml, and d. treating said patient for a stroke or transient ischemic attack.

2. The method of claim 1, wherein said cardiovascular peptide is CT-proAVP, MR-proADM, or CT-proET-1, and CT-proAVP is amino acids 107-145 of SEQ ID NO:12, MR-proADM is amino acids 45-92 of SEQ ID NO:1, and CT-proET-1 is amino acids 151-195 of SEQ ID NO:17.

3. The method of claim 1, wherein the levels of at least two of said cardiovascular peptides are detected and quantitated.

4. The method of claim 3, wherein the levels of a set of at least two cardiovascular peptides are detected and quantitated and the set of said at least two cardiovascular peptides is selected from the following combinations of cardiovascular peptides: MR-proANP and CT-proAVP, MR-proANP and MR-proADM, MR-proANP and CT-proET-1, MR-proANP and PCT, MR-proANP and hGH, MR-proADM and CT-proET-1, MR-proADM and PCT, MR-proADM and hGH, CT-proET-1 and PCT, CT-proET-1 and hGH, and PCT and hGH.

5. The method of claim 3, wherein the levels of a set of at least two cardiovascular peptides are detected and quantitated and the set of said at least two cardiovascular peptides is selected from the group comprising the following combinations of cardiovascular peptides:
MR-proANP and CT-proAVP,
MR-proANP and MR-proADM,
MR-proANP and CT-proET-1,
MR-proANP and PCT, and
MR-proANP and hGH.

6. The method of claim 5, wherein the set of said at least two cardiovascular peptides is MR-proANP and MR-proADM.

7. A method for detecting and quantitating the level of at least one cardiovascular peptide in a patient who has suffered a stroke or a transient ischemic attack, comprising:
a. obtaining a sample of bodily fluid from said patient,
b. detecting and quantitating in said sample from said patient the levels of a set of at least two cardiovascular peptides and the set of said at least two cardiovascular peptides is selected from following combinations of cardiovascular peptides: MR-proANP and CT-proAVP, MR-proANP and MR-proADM, MR-proANP and CT-proET-1, MR-proANP and PCT, MR-proANP and hGH, MR-proADM and CT-proET-1, MR-proADM and PCT, MR-proADM and hGH or CT-proET-1 and PCT, CT-proET-1 and hGH, and PCT and hGH,
wherein said detection and quantitation comprises contacting the sample with a diagnostic assay reagent comprising a capture probe that specifically binds to said cardiovascular peptide, and detecting and quantitating the thus-formed complexes of said capture probe and cardiovascular peptide,
wherein said detecting and quantitating is conducted on the first day of hospitalization (day 0) of said patient or on day 1 after hospitalization of said patient.

8. The method of claim 7, wherein the levels of a set of at least two cardiovascular peptides are detected and quantitated and the set of said at least two cardiovascular peptides is selected from the group comprising the following combinations of cardiovascular peptides:
MR-proANP and CT-proAVP,
MR-proANP and MR-proADM,
MR-proANP and CT-proET-1,
MR-proANP and PCT, and
MR-proANP and hGH.

9. The method of claim 8, wherein the set of said at least two cardiovascular peptides is MR-proANP and MR-proADM.

* * * * *